US012715871B2

(12) United States Patent
Wan et al.

(10) Patent No.: US 12,715,871 B2
(45) Date of Patent: Aug. 25, 2026

(54) AROMATIC RING-LACTAM COMPOUND, PREPARATION METHOD THEREFOR AND USE THEREOF

(71) Applicant: SHANGHAI RINGENE BIOPHARMA CO., LTD., Shanghai (CN)

(72) Inventors: Huixin Wan, Shanghai (CN); Chuantao Zha, Shanghai (CN); Jingui Ma, Shanghai (CN); Jingkang Shen, Shanghai (CN)

(73) Assignee: SHANGHAI RINGENE BIOPHARMA CO., LTD., Shanghai (CN)

( * ) Notice: Subject to any disclaimer, the term of this patent is extended or adjusted under 35 U.S.C. 154(b) by 629 days.

(21) Appl. No.: 18/041,075

(22) PCT Filed: Aug. 20, 2021

(86) PCT No.: PCT/CN2021/113864
§ 371 (c)(1),
(2) Date: Feb. 8, 2023

(87) PCT Pub. No.: WO2022/037691
PCT Pub. Date: Feb. 24, 2022

(65) Prior Publication Data

US 2023/0312564 A1 Oct. 5, 2023

(30) Foreign Application Priority Data

Aug. 21, 2020 (CN) ......................... 202010854400.4
Oct. 26, 2020 (CN) ......................... 202011161006.9
Dec. 18, 2020 (CN) ......................... 202011514897.1

(51) Int. Cl.

| | |
|---|---|
| ***C07D 471/04*** | (2006.01) |
| ***A61P 35/00*** | (2006.01) |
| ***C07D 401/14*** | (2006.01) |
| ***C07D 403/04*** | (2006.01) |
| ***C07D 403/14*** | (2006.01) |
| ***C07D 405/14*** | (2006.01) |

(52) U.S. Cl.
CPC ............ *C07D 471/04* (2013.01); *A61P 35/00* (2018.01); *C07D 401/14* (2013.01); *C07D 403/04* (2013.01); *C07D 403/14* (2013.01); *C07D 405/14* (2013.01)

(58) Field of Classification Search
CPC .. C07D 471/04; C07D 401/14; C07D 403/04; C07D 403/14; C07D 405/14; A61P 35/00
See application file for complete search history.

(56) References Cited

U.S. PATENT DOCUMENTS 11,001,575 B1 5/2021 Berdini et al.

FOREIGN PATENT DOCUMENTS

| | | | |
|---|---|---|---|
| CN | 108617166 A | | 10/2018 |
| WO | WO2017068412 A1 | * | 4/2017 |
| WO | 2018193410 A1 | | 10/2018 |

OTHER PUBLICATIONS

Lazzara et al.; Scaffold-hopping as a strategy to address metabolic liabilities of aromatic compounds; RSC Med. Chem., 2020, 11, 18-29. (Year: 2020).*
Heightman et al.; Fragment-Based Discovery of a Potent, Orally Bioavailable Inhibitor That Modulates the Phosphorylation and Catalytic Activity of ERK1/2; J. Med. Chem., 2018, 61, 4978-4992. (Year: 2018).*
Morita et al.; Application of Bioisosteres in Drug Design; Obtained From gousei.f.u-tokyo.ac.jp [Retrieved on Sep. 11, 2025] <URL: https://gousei.f.u-tokyo.ac.jp/seminar/index.html#2012>—Published May 2012. (Year: 2012).*
Cleveland Clinic; obtained from clevelandclinic.org [retrieved on Jan. 202, 2026]<URL: https://my.clevelandclinic.org/health/diseases/21624-autoimmune-diseases>—Pub. Date: Oct. 22, 2024.*
CDC; Obtained from cdc.gov [retrieved on Jan. 20, 2026]<URL: https://www.cdc.gov/diabetes/about/about-type-1-diabetes.html>—Pub. Date: May 15, 2024.*
Nov. 19, 2021 International Search Report issued in International Patent Application No. PCT/CN2021/113864.
Nov. 19, 2021 Written Opinion of the International Searching Authority issued in International Patent Application No. PCT/CN2021/113864.

(Continued)

*Primary Examiner* — Sarah Pihonak
*Assistant Examiner* — Jackson J Hernandez
(74) *Attorney, Agent, or Firm* — Houston Beshining Law Office PLLC; Liangang Ye

(57) ABSTRACT

Provided are an aromatic ring-lactam compound as shown in formula (I), and a preparation method therefor and the use thereof. The aromatic ring-lactam compound has a novel structure, has good inhibitory activity on ERK1/2 kinases, can inhibit the proliferation of tumor cells, and has anti-tumor activity.

(I)

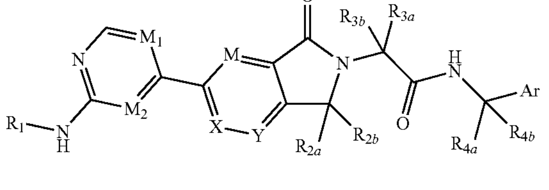

17 Claims, No Drawings

(56) References Cited

OTHER PUBLICATIONS

Tom D. Heightman, et al. Fragment-Based Discovery of a Potent, Orally Bioavailable Inhibitor That Modulates the Phosphorylation and Catalytic Activity of ERK1/2, J Med Chem. Jun. 14, 2018, 61(11):4978-4992.
Apr. 3, 2023 Chinese Second Office Action issued in Chinese Patent Application No. 2021109607607.
Sep. 22, 2022 Chinese First Office Action issued in Chinese Patent Application No. 2021109607607.
Jul. 31, 2024 extended European Search Report issued in EP21857779.9.

* cited by examiner

AROMATIC RING-LACTAM COMPOUND, PREPARATION METHOD THEREFOR AND USE THEREOF

The present application is a National Stage of International Application No. PCT/CN2021/113864, filed on Aug. 20, 2021, which claims the priorities of Chinese patent application 202010854400.4 filed on Aug. 21, 2020, Chinese patent application 202011161006.9 filed on Oct. 26, 2020, and Chinese patent application 202011514897.1 filed on Dec. 18, 2020. The contents of the Chinese patent applications are incorporated herein by reference in their entireties.

TECHNICAL FIELD

The present disclosure relates to an aromatic ring-fused lactam compound, a preparation method therefor and a use thereof.

BACKGROUND

Extracellular signal-regulated kinase 1/2 (ERK1/2) is a class of serine/threonine protein kinases discovered in 1990s, and it is one of the important subfamilies of mitogen-activated protein kinase MAPK family. Activated ERK1/2 can transmit extracellular signals to the nucleus, promote the phosphorylation of cytoplasmic target proteins or regulate the activity of other protein kinases, thus regulating gene expression. Ras-Raf-MEK-ERK signal transduction is the center of the signaling network involved in regulating cell growth, development and differentiation, so ERK1/2 has various biological effects such as regulating cell proliferation, differentiation, migration, invasion and apoptosis.

The Ras/Raf/MEK/ERK pathway is the main signaling pathway related to the function of ERK1/2, and it is a hot spot in the development of cancer-targeted drugs. In recent years, a number of drugs developed for node proteins on this signaling pathway had been successfully marketed. For example, the specific B-Raf inhibitors Vemurafenib and dabrafenib were marketed in 2011 and 2013 respectively for the treatment of melanoma, wherein dabrafenib was used for the treatment of B-RafV600E mutant non-small cell lung cancer and obtained the breakthrough drug qualification of FDA. Trametinib, a MEK1/2 inhibitor, was also marketed in 2013 for the treatment of melanoma. However, inhibiting these upstream pathway nodes has its limitations. Tumors can quickly develop resistance to B-Raf and MEK inhibitors, and Ras protein mutations are also found in many tumors, such as colorectal cancer, pancreatic cancer, lung cancer, etc. The mechanism of drug resistance of the above drugs includes point mutation, change of protein polymerization form, change of protein peptide chain length and other ways, which is a great challenge for the development of the next generation Ras-Raf-MEK drug resistance treatment drugs. However, ERK1/2, as a downstream key node of this pathway, has not been found to have drug resistance mutation. The targeted drug of ERK1/2 can greatly improve the treatment of patients who are resistant to upstream target inhibitors, and is a very promising field for the development of anti-cancer drugs. Although a number of ERK1/2 inhibitors had entered clinical research in the early stage, such as GDC0994, SCH772984, the clinical research of these compounds was terminated because of too much toxicity, poor druggability, or negative feedback drug resistance seriously affecting the efficacy. Therefore, discovering and searching for new ERK1/2 inhibitor compounds with high selectivity, high activity and high druggability has become a hot spot at present.

CONTENT OF THE PRESENT INVENTION

The technical problem to be solved by the present disclosure is that the existing ERK1/2 inhibitor has a single structure, therefore, the present disclosure provides a class of aromatic ring-fused lactam compounds, a preparation method therefor and a use thereof. The aromatic ring-fused lactam compound of the present disclosure has a novel structure, has a good inhibitory activity on ERK1/2 kinase, can inhibit the proliferation of tumor cells and has an anti-tumor activity.

The present disclosure solves the above technical problem through the following technical solutions.

In the first aspect of the present disclosure, the present disclosure provides a compound represented by formula (I), a pharmaceutically acceptable salt thereof, an enantiomer thereof, a diastereomer thereof, a tautomer thereof, a solvate thereof or a polymorph thereof;

(I)

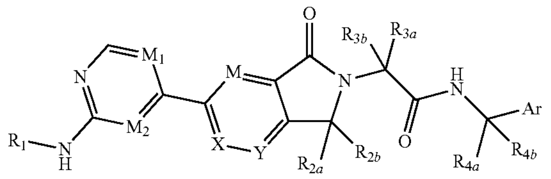

in the formula, $R_1$ is independently selected from any one of the following substituted or unsubstituted groups: $C_1$-$C_5$ alkyl, 3- to 8-membered cycloalkyl, 3- to 8-membered heterocycloalkyl, 5- to 10-membered aryl or 5- to 10-membered heteroaryl; the substituent comprises deuterium, halogen, hydroxyl, amino, $C_1$-$C_8$ alkyl, $C_1$-$C_8$ alkoxy, cyano, $C_1$-$C_8$ alkylamino, 3- to 8-membered cycloalkyl, 3- to 8-membered heterocycloalkyl, 5- to 10-membered aryl or 5- to 10-membered heteroaryl;

$R_{2a}$ and $R_{2b}$ are independently selected from hydrogen, deuterium, halogen, or any one of the following substituted or unsubstituted groups: $C_1$-$C_6$ alkyl, $C_1$-$C_6$ alkoxy, 3- to 8-membered cycloalkyl or 3- to 8-membered heterocycloalkyl; the substituent comprises deuterium, halogen, hydroxyl, amino, $C_1$-$C_8$ alkyl, $C_1$-$C_5$ alkoxy, cyano, $C_1$-$C_5$ alkylamino, 3- to 8-membered cycloalkyl, 3- to 8-membered heterocycloalkyl, 5- to 10-membered aryl or 5- to 10-membered heteroaryl;

$R_{3a}$ and $R_{3b}$ are independently selected from hydrogen, deuterium, halogen, or any one of the following substituted or unsubstituted groups: $C_1$-$C_6$ alkyl, $C_1$-$C_6$ alkoxy; the substituent comprises deuterium, halogen, hydroxyl, amino, $C_1$-$C_5$ alkyl, $C_1$-$C_8$ alkoxy, cyano, $C_1$-$C_8$ alkylamino, 3- to 8-membered cycloalkyl, 3- to 8-membered heterocycloalkyl, 5- to 10-membered aryl or 5- to 10-membered heteroaryl;

$R_{4a}$ and $R_{4b}$ are independently selected from hydrogen, deuterium, halogen, or the following substituted or unsubstituted groups: $C_1$-$C_6$ alkyl, $C_1$-$C_6$ alkoxy, 3- to 8-membered cycloalkyl or 3- to 8-membered heterocycloalkyl; the substituent comprises deuterium, halogen, hydroxyl, amino, $C_1$-$C_8$ alkyl, $C_1$-$C_8$ alkoxy, cyano, $C_1$-$C_8$ alkylamino, 3- to 8-membered cycloalkyl, 3- to 8-membered heterocycloalkyl;

or, any two groups of $R_{2a}$ and $R_{2b}$, $R_{3a}$ and $R_{3b}$, $R_{4a}$ and $R_{4b}$ can form a 3- to 8-membered saturated or partially unsaturated carbocyclic ring or heterocyclic ring;

Ar is selected from any one of the following substituted or unsubstituted groups: 3- to 8-membered cycloalkyl, 3- to 8-membered heterocycloalkyl, 5- to 10-membered aryl or 5- to 10-membered heteroaryl;

M is selected from N or $CR_5$; $R_5$ is independently selected from halogen, cyano, nitro, $C_1$-$C_6$ alkyl, or 3- to 8-membered cycloalkyl;

$M_1$, $M_2$, X and Y are each independently selected from N or $CR_6$; $R_6$ is independently selected from hydrogen, halogen, cyano, nitro, $C_1$-$C_6$ alkyl, or 3- to 8-membered cycloalkyl;

wherein, the heteroaryl contains 1 to 3 heteroatoms selected from the following group: N, O, P and S, and the heterocycloalkyl contains 1 to 3 heteroatoms selected from following group: N, O, P and S; each ring system is independently saturated, partially unsaturated or unsaturated monocyclic, fused, bridged or spiro ring.

In some preferred embodiments of the present disclosure, some groups of the compound represented by formula (I) are defined as follows, and the rest groups are defined as described in the previous embodiments (hereinafter referred to as "in some preferred embodiments of the present disclosure"):

In $R_1$, the substituent is deuterium, halogen, hydroxyl, amino, $C_1$-$C_8$ alkyl, $C_1$-$C_8$ alkoxy, cyano, $C_1$-$C_8$ alkylamino, 3- to 8-membered cycloalkyl, 3- to 8-membered heterocycloalkyl, 5- to 10-membered aryl or 5- to 10-membered heteroaryl.

In some preferred embodiments of the present disclosure, in $R_{2a}$ and $R_{2b}$, the substituent is deuterium, halogen, hydroxyl, amino, $C_1$-$C_8$ alkyl, $C_1$-$C_8$ alkoxy, cyano, $C_1$-$C_8$ alkylamino, 3- to 8-membered cycloalkyl, 3- to 8-membered heterocycloalkyl, 5- to 10-membered aryl or 5- to 10-membered heteroaryl.

In some preferred embodiments of the present disclosure, in $R_{3a}$ and $R_{3b}$, the substituent is deuterium, halogen, hydroxyl, amino, $C_1$-$C_8$ alkyl, $C_1$-$C_8$ alkoxy, cyano, $C_1$-$C_8$ alkylamino, 3- to 8-membered cycloalkyl, 3- to 8-membered heterocycloalkyl, 5- to 10-membered aryl or 5- to 10-membered heteroaryl.

In some preferred embodiments of the present disclosure, in $R_{4a}$ and $R_{4b}$, the substituent is deuterium, halogen, hydroxyl, amino, $C_1$-$C_8$ alkyl, $C_1$-$C_8$ alkoxy, cyano, $C_1$-$C_8$ alkylamino, 3- to 8-membered cycloalkyl, 3- to 8-membered heterocycloalkyl.

In some preferred embodiments of the present disclosure, when any two groups of $R_{2a}$ and $R_{2b}$, $R_{3a}$ and $R_{3b}$, $R_{4a}$ and $R_{4b}$ form the 3- to 8-membered saturated or partially unsaturated carbocyclic ring or heterocyclic ring, the heteroatom in the heterocyclic ring is 1 to 3 heteroatoms selected from the following group: N, O, P and S.

In some preferred embodiments of the present disclosure, in Ar, the number of the substituent is 1 or more, and the substituent is independently selected from halogen, $C_1$-$C_6$ alkyl, $C_1$-$C_6$ alkoxy, deuterated $C_1$-$C_6$ alkoxy or $C_1$-$C_6$ alkylamino.

In some preferred embodiments of the present disclosure, $R_1$ is $C_1$-$C_8$ alkyl, 3- to 8-membered heterocycloalkyl, 3- to 8-membered cycloalkyl, 5- to 10-membered aryl, 5- to 10-membered heteroaryl, substituted $C_1$-$C_8$ alkyl, substituted 3- to 8-membered cycloalkyl, substituted 5- to 10-membered aryl or substituted 5- to 10-membered heteroaryl; the substituent is halogen, hydroxyl, $C_1$-$C_8$ alkyl or 3- to 8-membered heterocycloalkyl.

In some preferred embodiments of the present disclosure, $R_1$ is $C_1$-$C_8$ alkyl, 3- to 8-membered heterocycloalkyl, 3- to 8-membered cycloalkyl, 5- to 10-membered aryl, 5- to 10-membered heteroaryl, substituted 3- to 8-membered cycloalkyl, substituted 5- to 10-membered aryl or substituted 5- to 10-membered heteroaryl; the substituent is halogen, hydroxyl, $C_1$-$C_8$ alkyl or 3- to 8-membered heterocycloalkyl.

In some preferred embodiments of the present disclosure, $R_1$ is 3- to 8-membered heterocycloalkyl.

In some preferred embodiments of the present disclosure, $R_{2a}$ and $R_{2b}$ are hydrogen.

In some preferred embodiments of the present disclosure, $R_{3a}$ is hydrogen; $R_{3b}$ is $C_1$-$C_6$ alkyl.

In some preferred embodiments of the present disclosure, $R_{4a}$ is hydrogen; $R_{4b}$ is hydrogen or substituted $C_1$-$C_6$ alkyl; the substituent is hydroxyl or amino.

In some preferred embodiments of the present disclosure, $R_{4a}$ is hydrogen; $R_{4b}$ is substituted $C_1$-$C_6$ alkyl; the substituent is hydroxyl.

In some preferred embodiments of the present disclosure, Ar is 5- to 10-membered aryl, 5- to 10-membered heteroaryl, substituted 5- to 10-membered aryl or substituted 5- to 10-membered heteroaryl; the substituent is halogen, $C_1$-$C_6$ alkyl, $C_1$-$C_6$ alkoxy, $C_1$-$C_6$ alkylamino or deuterated $C_1$-$C_6$ alkoxy.

In some preferred embodiments of the present disclosure, Ar is substituted 5- to 10-membered aryl; the substituent is halogen, $C_1$-$C_6$ alkyl, $C_1$-$C_6$ alkoxy, $C_1$-$C_6$ alkylamino or deuterated $C_1$-$C_6$ alkoxy.

In some preferred embodiments of the present disclosure, M is selected from Nor $CR_5$; $R_5$ is halogen.

In some preferred embodiments of the present disclosure, $M_1$ and $M_2$ are independently N or $CR_6$; $R_6$ is independently selected from hydrogen, halogen or $C_1$-$C_6$ alkyl.

In some preferred embodiments of the present disclosure, $M_1$ is $CR_5$ and $R_6$ is halogen; $M_2$ is N.

In some preferred embodiments of the present disclosure, X and Y are $CR_6$; $R_6$ is hydrogen.

In some preferred embodiments of the present disclosure, (I)

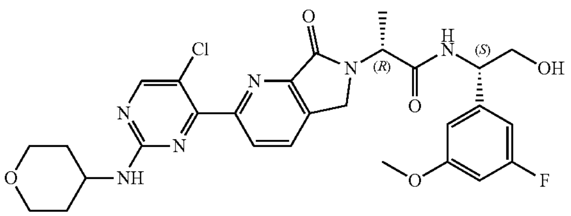

in the formula, $R_1$ is $C_1$-$C_8$ alkyl, 3- to 8-membered heterocycloalkyl, 3- to 8-membered cycloalkyl, 5- to 10-membered aryl, 5- to 10-membered heteroaryl, substituted 3- to 8-membered cycloalkyl, substituted 5- to 10-membered aryl or substituted 5- to 10-membered heteroaryl; the substituent is halogen, hydroxyl, $C_1$-$C_8$ alkyl or 3- to 8-membered heterocycloalkyl;

$R_{2a}$ and $R_{2b}$ are hydrogen;

$R_{3a}$ is hydrogen; $R_{3b}$ is $C_1$-$C_6$ alkyl;

$R_{4a}$ is hydrogen; $R_{4b}$ is hydrogen or substituted $C_1$-$C_6$ alkyl; the substituent is hydroxyl or amino;

Ar is 5- to 10-membered aryl, 5- to 10-membered heteroaryl, substituted 5- to 10-membered aryl or substituted 5- to 10-membered heteroaryl; the substituent is halogen, $C_1$-$C_6$ alkyl, $C_1$-$C_6$ alkoxy, $C_1$-$C_6$ alkylamino or deuterated $C_1$-$C_6$ alkoxy;

M is selected from N or $CR_5$; $R_5$ is halogen;

$M_1$ and $M_2$ are independently N or $CR_6$; $R_6$ is independently selected from hydrogen, halogen or $C_1$-$C_6$ alkyl;

X and Y are $CR_6$; $R_6$ is hydrogen.

In some preferred embodiments of the present disclosure, (I)

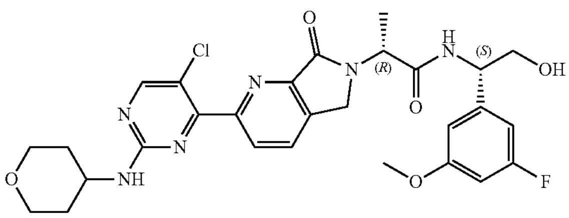

in the formula, $R_1$ is 3- to 8-membered heterocycloalkyl;

$R_{2a}$ and $R_{2b}$ are hydrogen;

$R_{3a}$ is hydrogen; $R_{3b}$ is $C_1$-$C_6$ alkyl;

$R_{4a}$ is hydrogen; $R_{4b}$ is substituted $C_1$-$C_6$ alkyl; the substituent is hydroxyl;

Ar is substituted 5- to 10-membered aryl; the substituent is halogen, $C_1$-$C_6$ alkyl, $C_1$-$C_6$ alkoxy, $C_1$-$C_6$ alkylamino or deuterated $C_1$-$C_6$ alkoxy;

M is selected from N or $CR_5$; $R_5$ is halogen;

$M_1$ is $CR_6$, $R_6$ is halogen; $M_2$ is N;

X and Y are $CR_6$; $R_6$ is hydrogen.

In some preferred embodiments of the present disclosure, the compound represented by formula (I) is a compound represented by formula 1:

1

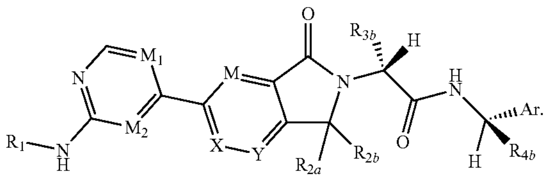

In some preferred embodiments of the present disclosure, in $R_1$, when the substituent is halogen, the halogen is fluorine, chlorine, bromine or iodine.

In some preferred embodiments of the present disclosure, in $R_1$, when the substituent is $C_1$-$C_8$ alkyl, the $C_1$-$C_8$ alkyl can be methyl, ethyl, n-propyl, isopropyl, n-butyl, isobutyl, sec-butyl or tert-butyl.

In some preferred embodiments of the present disclosure, in $R_1$, when the substituent is 3- to 8-membered heterocycloalkyl, the 3- to 8-membered heterocycloalkyl can be 5- to 6-membered heterocycloalkyl.

In some preferred embodiments of the present disclosure, in $R_1$, when the substituent is 3- to 8-membered heterocycloalkyl, the heteroatom of the 3- to 8-membered heterocycloalkyl is 1 to 2 heteroatoms selected from the following group: O and N.

In some preferred embodiments of the present disclosure, in $R_1$, when the substituent is 3- to 8-membered heterocycloalkyl, each ring system is a saturated monocyclic ring.

In some preferred embodiments of the present disclosure, in $R_1$, when the substituent is 3- to 8-membered heterocycloalkyl, the 3- to 8-membered heterocycloalkyl can be morpholinyl.

In some preferred embodiments of the present disclosure, in $R^1$, when the substituent is 3- to 8-membered heterocycloalkyl, the 3- to 8-membered heterocycloalkyl can be

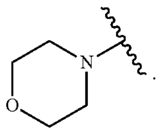 [SMILES: *N1CCOCC1]

In some preferred embodiments of the present disclosure, in $R_1$, the $C_1$-$C_8$ alkyl can be methyl, ethyl, n-propyl, isopropyl, n-butyl, isobutyl, sec-butyl or tert-butyl.

In some preferred embodiments of the present disclosure, in $R_1$, the 3- to 8-membered heterocycloalkyl can be 5- to 6-membered heterocycloalkyl.

In some preferred embodiments of the present disclosure, in $R_1$, the heteroatom of the 3- to 8-membered heterocycloalkyl is 1 to 2 of O atoms.

In some preferred embodiments of the present disclosure, in $R_1$, in the 3- to 8-membered heterocycloalkyl, each ring system is a saturated monocyclic ring.

In some preferred embodiments of the present disclosure, in $R_1$, the 3- to 8-membered heterocycloalkyl can be tetrahydropyranyl, tetrahydrofuranyl or oxetanyl.

In some preferred embodiments of the present disclosure, in $R_1$, the 3- to 8-membered heterocycloalkyl can be

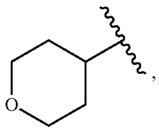,
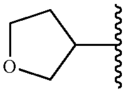
or
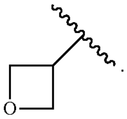.

In some preferred embodiments of the present disclosure, in $R_1$, the 3- to 8-membered cycloalkyl can be 4- to 6-membered cycloalkyl.

In some preferred embodiments of the present disclosure, in $R_1$, in the 3- to 8-membered cycloalkyl, each ring system is a saturated monocyclic ring.

In some preferred embodiments of the present disclosure, in $R_1$, in the 3- to 8-membered cycloalkyl, the 3- to 8-membered cycloalkyl is not oxidized.

In some preferred embodiments of the present disclosure, in $R_1$, in the 3- to 8-membered cycloalkyl, the 3- to 8-membered cycloalkyl can be cyclobutyl, cyclopentyl or cyclohexyl.

In some preferred embodiments of the present disclosure, in $R_1$, the substituted 3- to 8-membered cycloalkyl can be

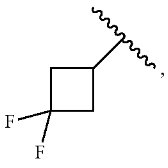,
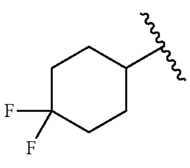
or

-continued

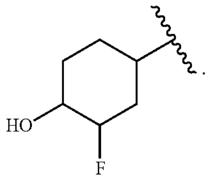

In some preferred embodiments of the present disclosure, in $R_1$, the 5- to 10-membered aryl can be 6- to 10-membered aryl, and can also be phenyl.

In some preferred embodiments of the present disclosure, in $R_1$, the substituted 5- to 10-membered aryl can be

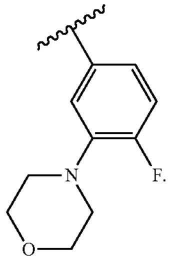 [SMILES: *c1ccc(F)c(N2CCOCC2)c1]

In some preferred embodiments of the present disclosure, in $R_1$, the 5- to 10-membered heteroaryl can be 5- to 6-membered heteroaryl.

In some preferred embodiments of the present disclosure, in $R_1$, the heteroatom of the 5- to 10-membered heteroaryl is 1 to 2 of N atoms.

In some preferred embodiments of the present disclosure, in $R_1$, in the 5- to 10-membered heteroaryl, each ring system is a monocyclic ring.

In some preferred embodiments of the present disclosure, in $R_1$, in the 5- to 10-membered heteroaryl, the nitrogen atom in the 5- to 10-membered heteroaryl is not oxidized.

In some preferred embodiments of the present disclosure, in $R_1$, the nitrogen atom in the 5- to 10-membered heteroaryl is not quaternized.

In some preferred embodiments of the present disclosure, in $R_1$, in the 5- to 10-membered heteroaryl, the 5- to 10-membered heteroaryl can be pyrazolyl.

In some preferred embodiments of the present disclosure, in $R_1$, the substituted 5- to 10-membered heteroaryl can be

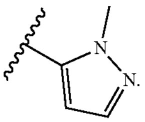 [SMILES: *c1ccnn1C]

In some preferred embodiments of the present disclosure, in $R_{3b}$, the $C_1$-$C_6$ alkyl can be methyl, ethyl, n-propyl, isopropyl, n-butyl, isobutyl, sec-butyl or tert-butyl.

In some preferred embodiments of the present disclosure, in $R_{4b}$, in the substituted $C_1$-$C_6$ alkyl, the $C_1$-$C_6$ alkyl can be methyl, ethyl, n-propyl, isopropyl, n-butyl, isobutyl, sec-butyl or tert-butyl.

In some preferred embodiments of the present disclosure, in $R_{4b}$, the substituted $C_1$-$C_6$ alkyl can be hydroxymethyl or aminomethyl.

In some preferred embodiments of the present disclosure, in $R_{4b}$, the substituted $C_1$-$C_6$ alkyl can be aminomethyl.

In some preferred embodiments of the present disclosure, in Ar, when the substituent is halogen, the halogen is fluorine, chlorine, bromine or iodine.

In some preferred embodiments of the disclosure, in Ar, when the substituent is $C_1$-$C_6$ alkyl, the $C_1$-$C_6$ alkyl can be methyl, ethyl, n-propyl, isopropyl, n-butyl, isobutyl, sec-butyl or tert-butyl.

In some preferred embodiments of the disclosure, in Ar, when the substituent is $C_1$-$C_6$ alkoxy, the $C_1$-$C_6$ alkoxy can be methoxy, ethoxy, n-propoxy, isopropoxy, n-butoxy, isobutoxy, sec-butoxy or tert-butoxy.

In some preferred embodiments of the present disclosure, in Ar, when the substituent is $C_1$-$C_6$ alkylamino, the $C_1$-$C_6$ alkylamino is dimethylamino.

In some preferred embodiments of the disclosure, in Ar, the deuterated $C_1$-$C_6$ alkoxy can be trideuterated methoxy.

In some preferred embodiments of the present disclosure, in Ar, in the 5- to 10-membered aryl, the 5- to 10-membered aryl can be 6- to 10-membered aryl, and can also be phenyl.

In some preferred embodiments of the present disclosure, in Ar, the substituted 5- to 10-membered aryl can be

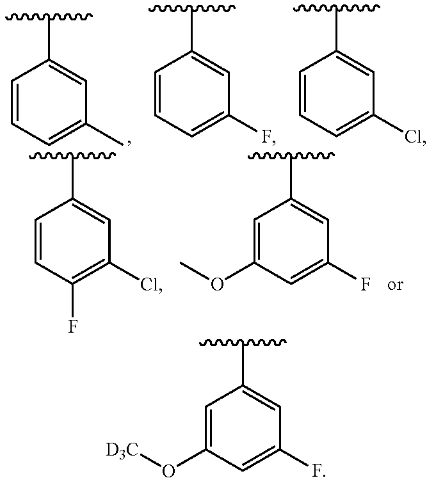

, , , , or

In some preferred embodiments of the present disclosure, in Ar, the 5- to 10-membered heteroaryl can be 5- to 6-membered heteroaryl.

In some preferred embodiments of the present disclosure, in Ar, the heteroatom of the 5- to 10-membered heteroaryl is 1 to 2 of N atoms.

In some preferred embodiments of the present disclosure, in Ar, in the 5- to 10-membered heteroaryl, each ring system is a monocyclic ring.

In some preferred embodiments of the present disclosure, in Ar, in the 5- to 10-membered heteroaryl, the nitrogen atom in the 5- to 10-membered heteroaryl is not oxidized.

In some preferred embodiments of the present disclosure, in Ar, in the 5- to 10-membered heteroaryl, the nitrogen atom in the 5- to 10-membered heteroaryl is not quaternized.

In some preferred embodiments of the present disclosure, in Ar, in the 5- to 10-membered heteroaryl, the 5- to 10-membered heteroaryl can be pyridyl.

In some preferred embodiments of the present disclosure, in Ar, the substituted 5- to 10-membered heteroaryl can be

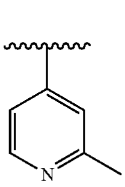 or 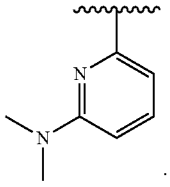 .

In some preferred embodiments of the present disclosure, in $R_5$, the halogen is fluorine, chlorine, bromine or iodine.

In some preferred embodiments of the present disclosure, in $R_6$, the halogen is fluorine, chlorine, bromine or iodine.

In some preferred embodiments of the present disclosure, in $R_6$, the $C_1$-$C_6$ alkyl can be methyl, ethyl, n-propyl, isopropyl, n-butyl, isobutyl, sec-butyl or tert-butyl.

In some preferred embodiments of the present disclosure, some groups of the compound represented by formula (I) are defined as follows (undefined groups are as described in any one of previous embodiments): $M_1$ is N, $M_2$ is N.

In some preferred embodiments of the present disclosure, some groups of the compound represented by formula (I) are defined as follows (undefined groups are as described in any one of previous embodiments): $M_1$ is N, $M_2$ is CH.

In some preferred embodiments of the present disclosure, some groups of the compound represented by formula (I) are defined as follows (undefined groups are as described in any one of previous embodiments): $M_1$ is $CR_6$, $M_2$ is CH.

In some preferred embodiments of the present disclosure, some groups of the compound represented by formula (I) are defined as follows (undefined groups are as described in any one of previous embodiments): $M_1$ is $CR_6$, $M_2$ is N.

In some preferred embodiments of the present disclosure, some groups of the compound represented by formula (I) are defined as follows (undefined groups are as described in any one of previous embodiments): M is N.

In some preferred embodiments of the present disclosure, some groups of the compound represented by formula (I) are defined as follows (undefined groups are as described in any one of previous embodiments): M is C—F.

In some preferred embodiments of the present disclosure, some groups of the compound represented by formula (I) are defined as follows (undefined groups are as described in any one of previous embodiments): $R_1$ is any one of the following substituted or unsubstituted groups: $C_1$-$C_8$ alkyl, 3- to 8-membered cycloalkyl, 3-to 8-membered heterocycloalkyl, 5-to 10- membered aryl or 5-to 10-membered heteroaryl; preferably any one of the following substituted or unsubstituted groups: $C_3$-$C_8$ alkyl, 4-to 6-membered cycloalkyl, 4-to 6-membered heterocycloalkyl, 5-to 6-membered aryl or 5-to 6-membered heteroaryl; more preferably any one of the following substituted or unsubstituted groups: isopropyl, cyclobutyl, cyclopentyl, cyclohexyl, oxetanyl, oxolanyl, tetrahydropyranyl, phenyl, pyridyl, pyrazolyl; the substituent comprises deuterium, halogen, C1-C8 alkyl, C1-C8alkoxy, 3-to 8-membered cycloalkyl, 3-to 8-membered heterocycloalkyl, 5-to 10-membered aryl, 5-to 10-membered heteroaryl;

$R_{2a}$ or $R_{2b}$ is respectively hydrogen, deuterium, fluorine, methyl, methoxy;

$R_{3a}$ or $R_{3b}$ is respectively hydrogen, deuterium, fluorine, methyl, methoxy, hydroxymethyl, aminomethyl, $C_1$-$C_8$ haloalkyl;

$R_{4a}$ is hydrogen, deuterium, fluorine, methyl;

$R_{4b}$ is hydrogen, deuterium, fluorine, methyl, $C_1$-$C_8$ haloalkyl, methoxymethylene, hydroxymethylene, aminomethylene;

Ar is any one of the following substituted or unsubstituted groups: 5-to 6-membered cycloalkyl, 5-to 6-membered heterocycloalkyl, 5-to 6-membered aryl or 5-to 6-membered heteroaryl; more preferably any one of the following substituted or unsubstituted groups: cyclopentyl, cyclohexyl, phenyl, pyridyl; the substituent comprises one or more than one deuterium, halogen, $C_1$-$C_8$ alkyl, $C_1$-$C_8$ alkoxy, $C_1$-$C_8$ haloalkyl, $C_1$-$C_8$ haloalkoxy, amino, cyano, $C_1$-$C_6$ monoalkylamino, $C_1$-$C_6$ dialkylamino, 3-to 8-membered heterocycloalkyl;

X or Y is N, CH or C—F.

In another preferred embodiment, the compound represented by formula (I) is preferably selected from the following general formula ((I)A):

((I)A)

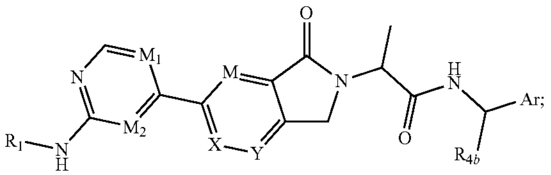

In another preferred embodiment, the compound represented by formula (I) is preferably selected from the following general formulas ((I)B) and ((I)C):

((I)B)

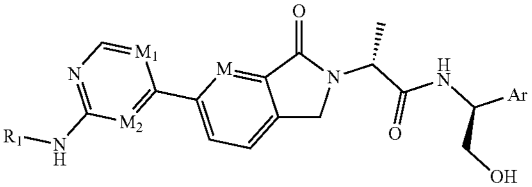 and ((I)C)

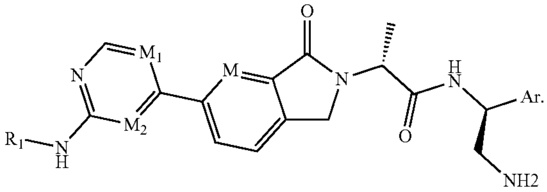

In some preferred embodiments of the present disclosure, the compound represented by formula (I) can be any one of the following compounds:

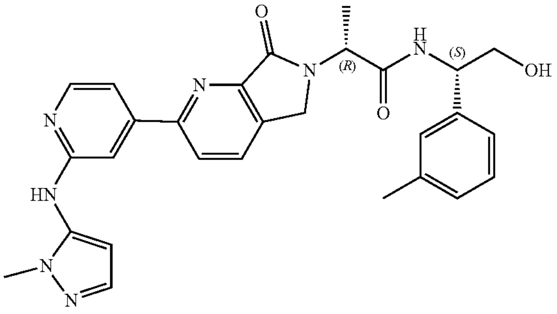
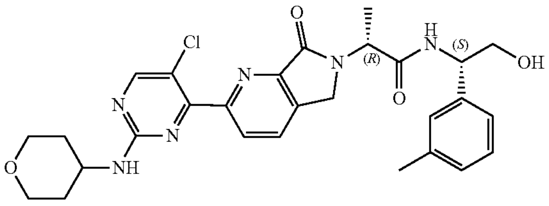
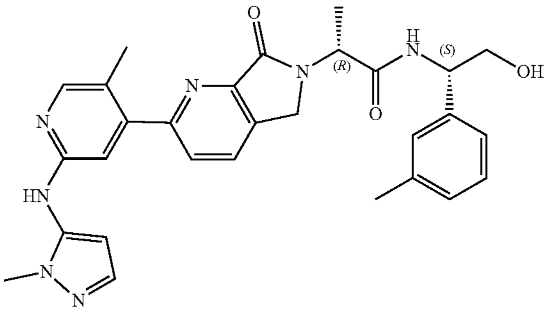
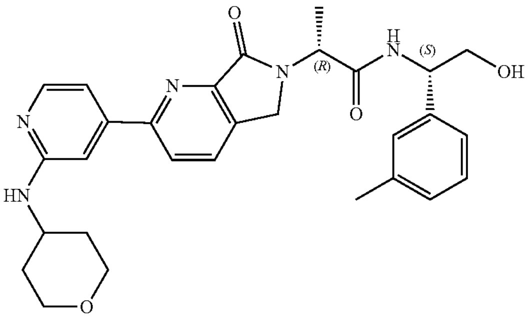
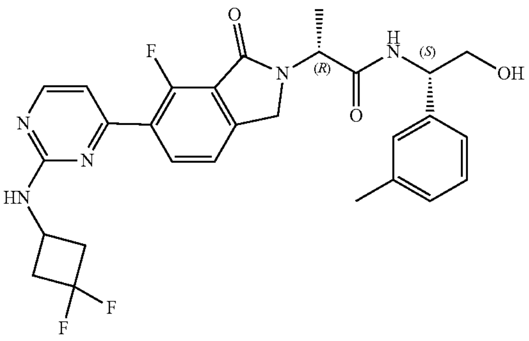
-continued
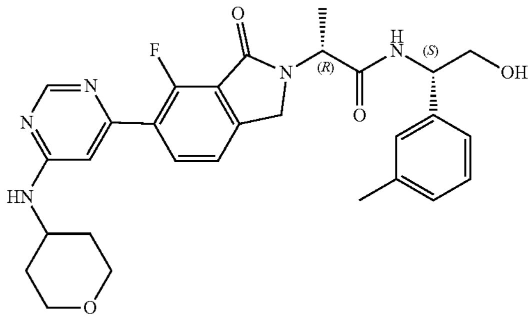
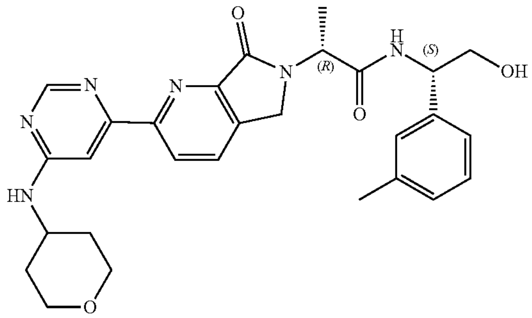
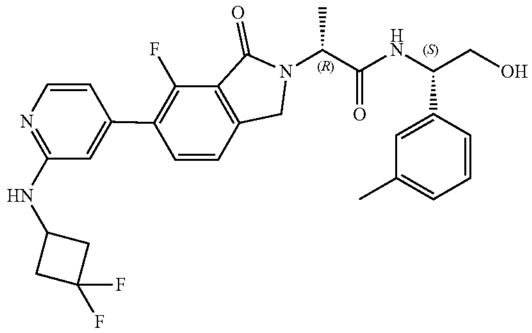
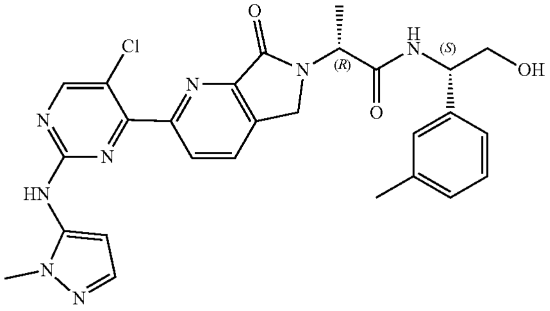
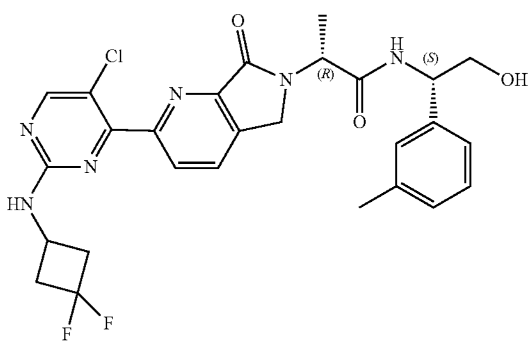

-continued
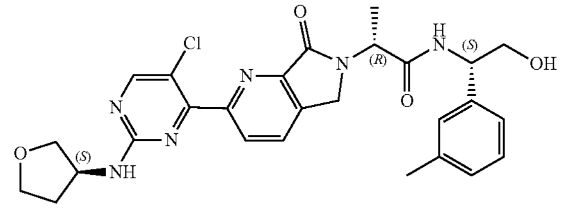
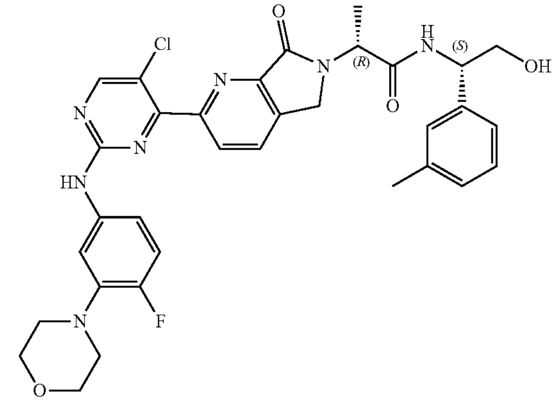
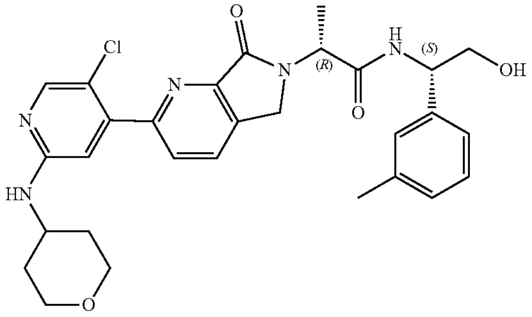
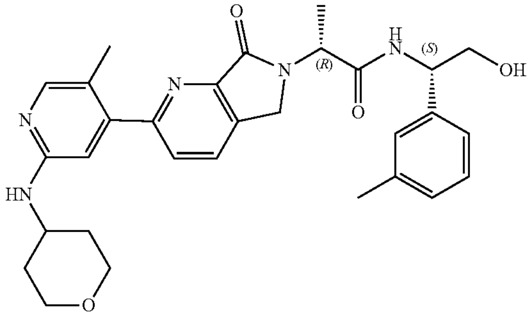
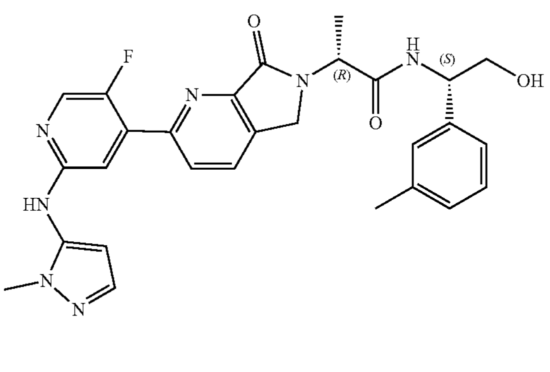
-continued
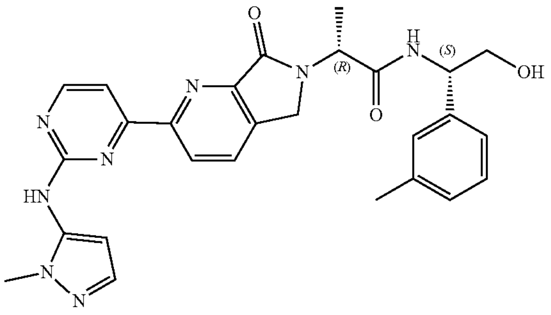
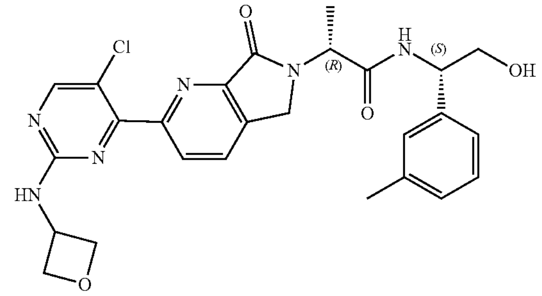
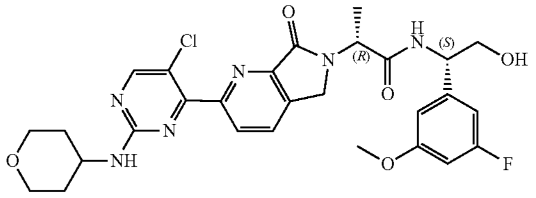
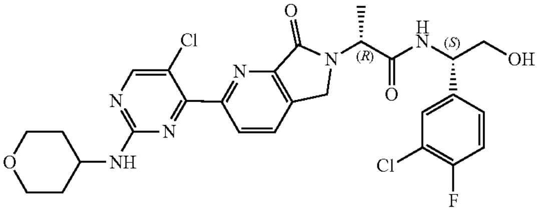
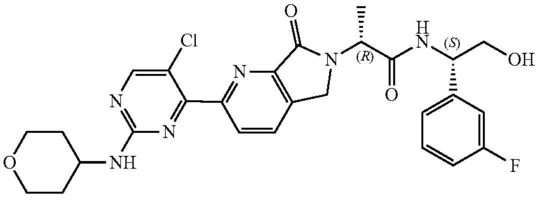
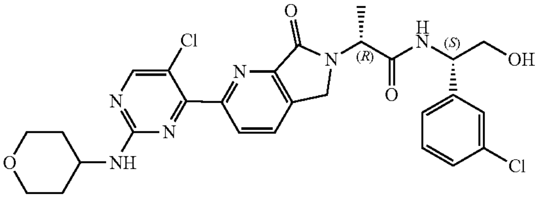
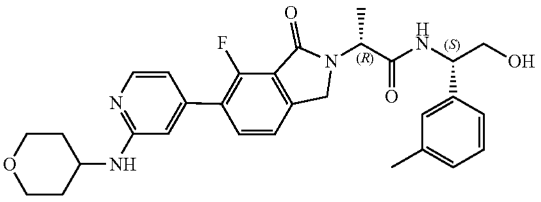

-continued
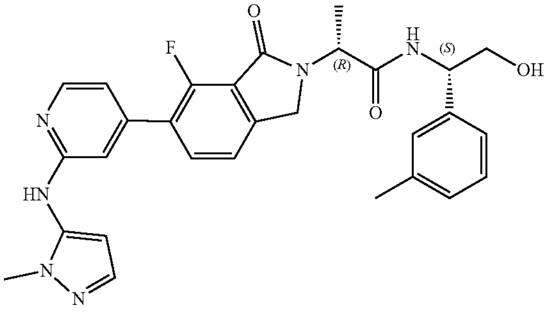
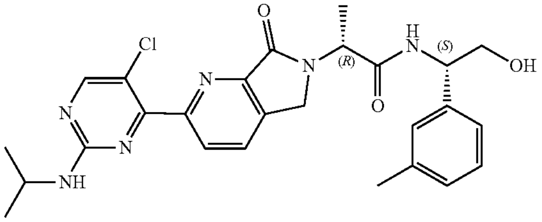
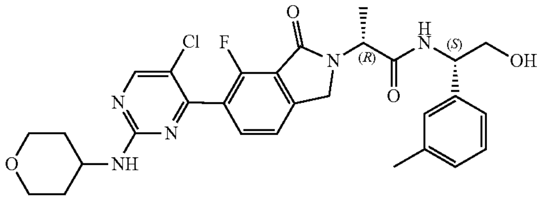
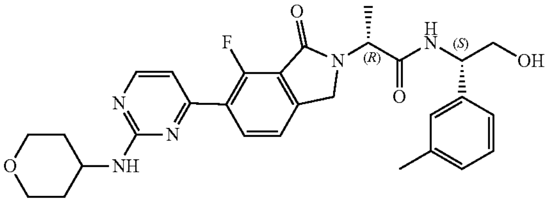
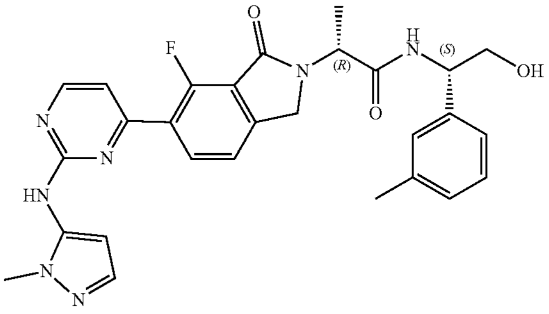
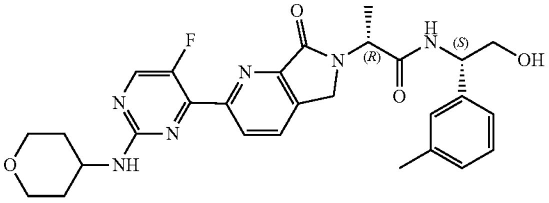
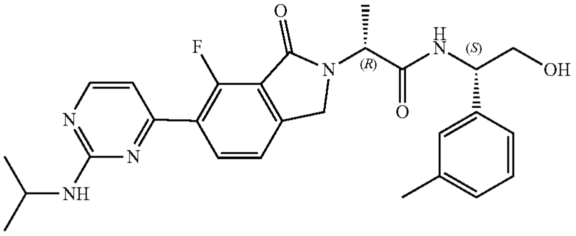
-continued
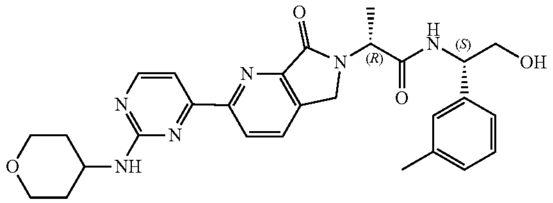
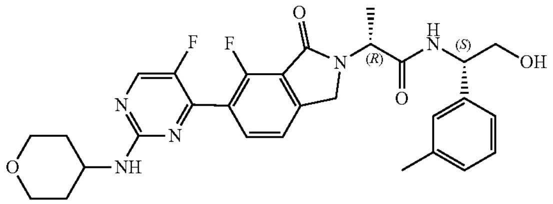
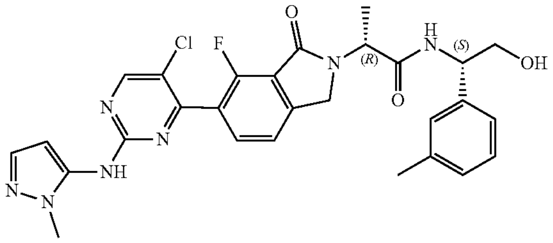
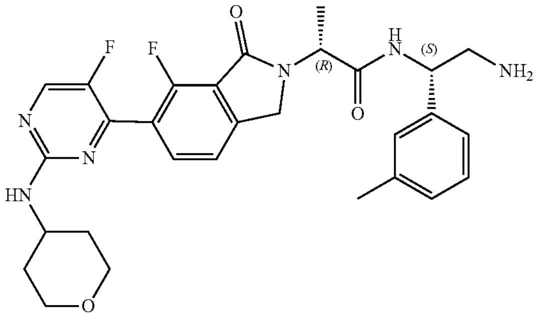
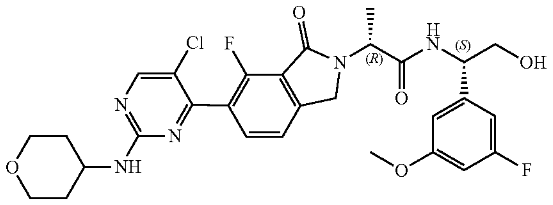
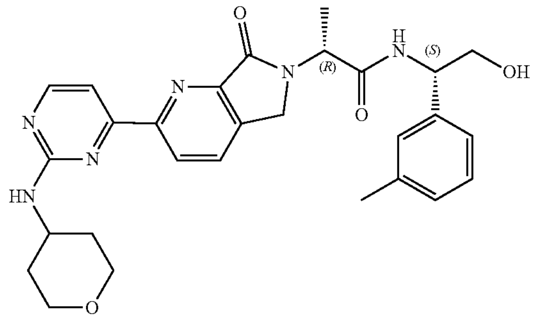
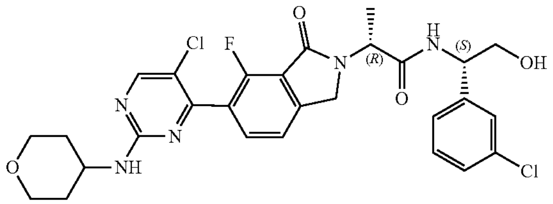

-continued
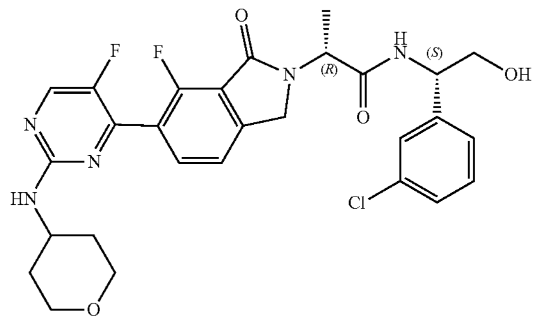
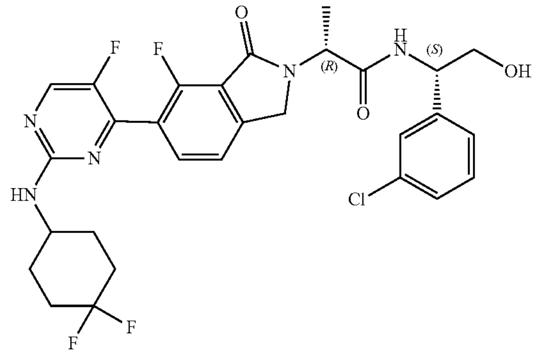
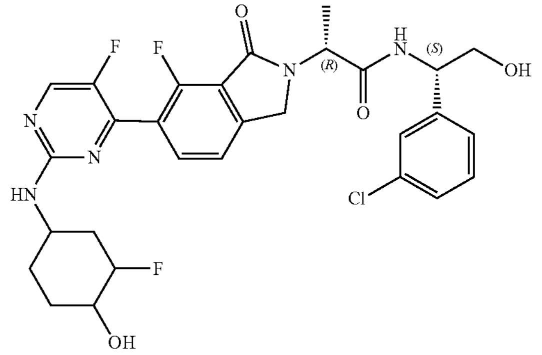
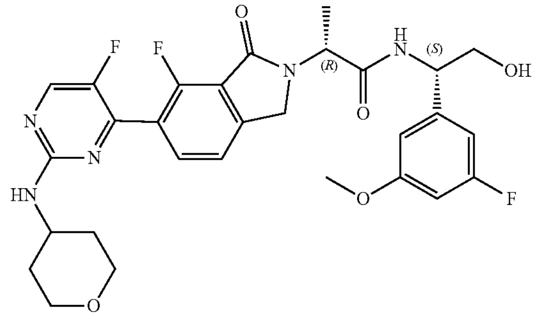
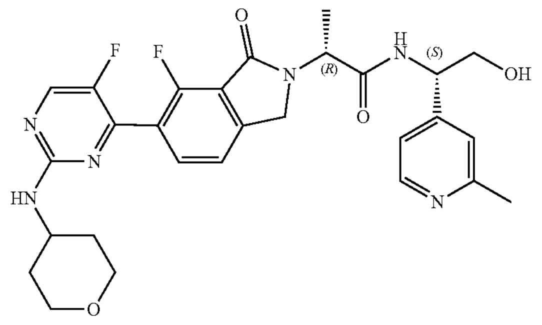
-continued
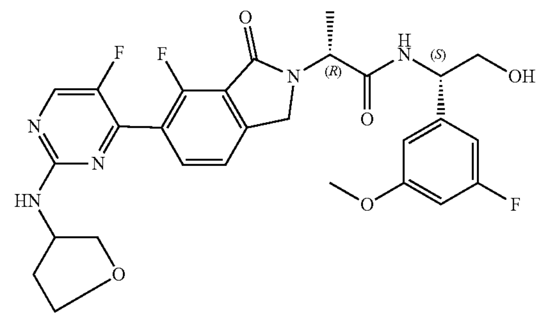
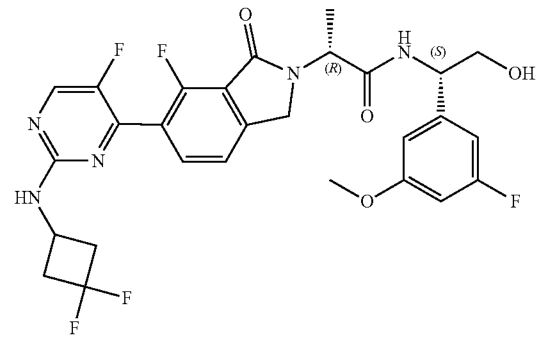
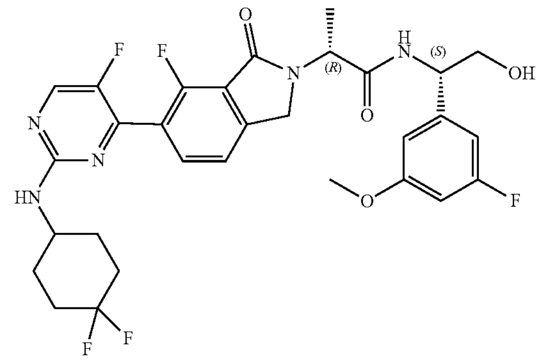
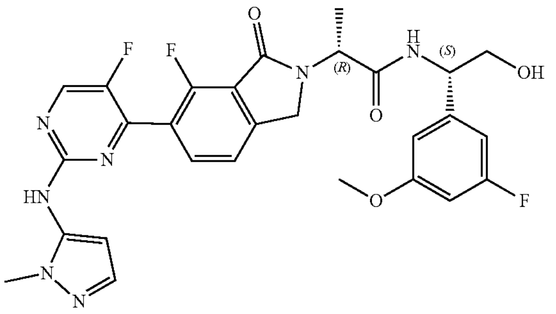
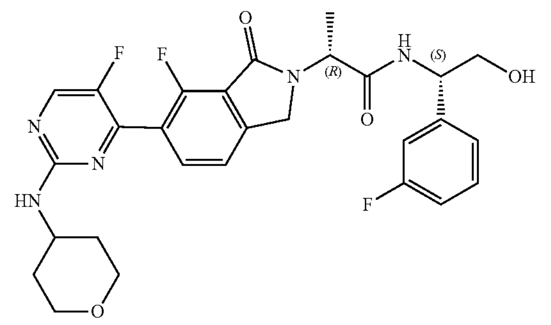

-continued

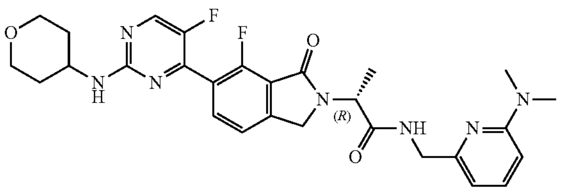

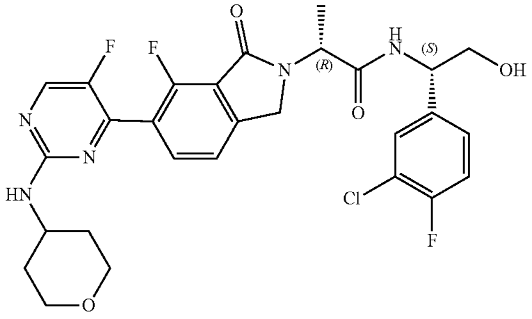

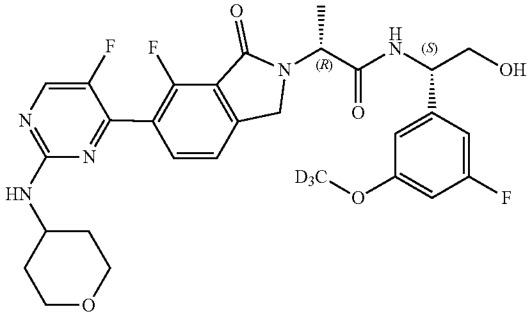

-continued

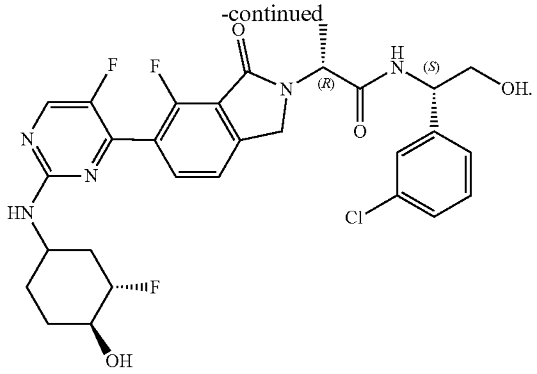

In the second aspect, the present disclosure provides a method for preparing the compound represented by formula (I), comprising steps a to c:

a) carrying out a cross-coupling reaction between an intermediate compound represented by general formula (A1) or (A2) or (A3) with an intermediate compound represented by general formula (B1) or (B2) or (B3) to obtain a compound represented by general formula (C1) or (C2) under the reaction conditions of the presence of transition metal catalyst;

b) under the reaction conditions of acid catalysis, base catalysis or transition metal catalysis coupling reaction conditions, reacting the compound represented by general formula (C1) with a raw material compound represented by general formula $R_1NH_2$ to obtain the compound represented by general formula (C2);

c) after removing the protecting group of the compound represented by general formula (C2), preparing the compound represented by formula (I) by a conventional condensation reaction of a carboxylic acid and an amine;

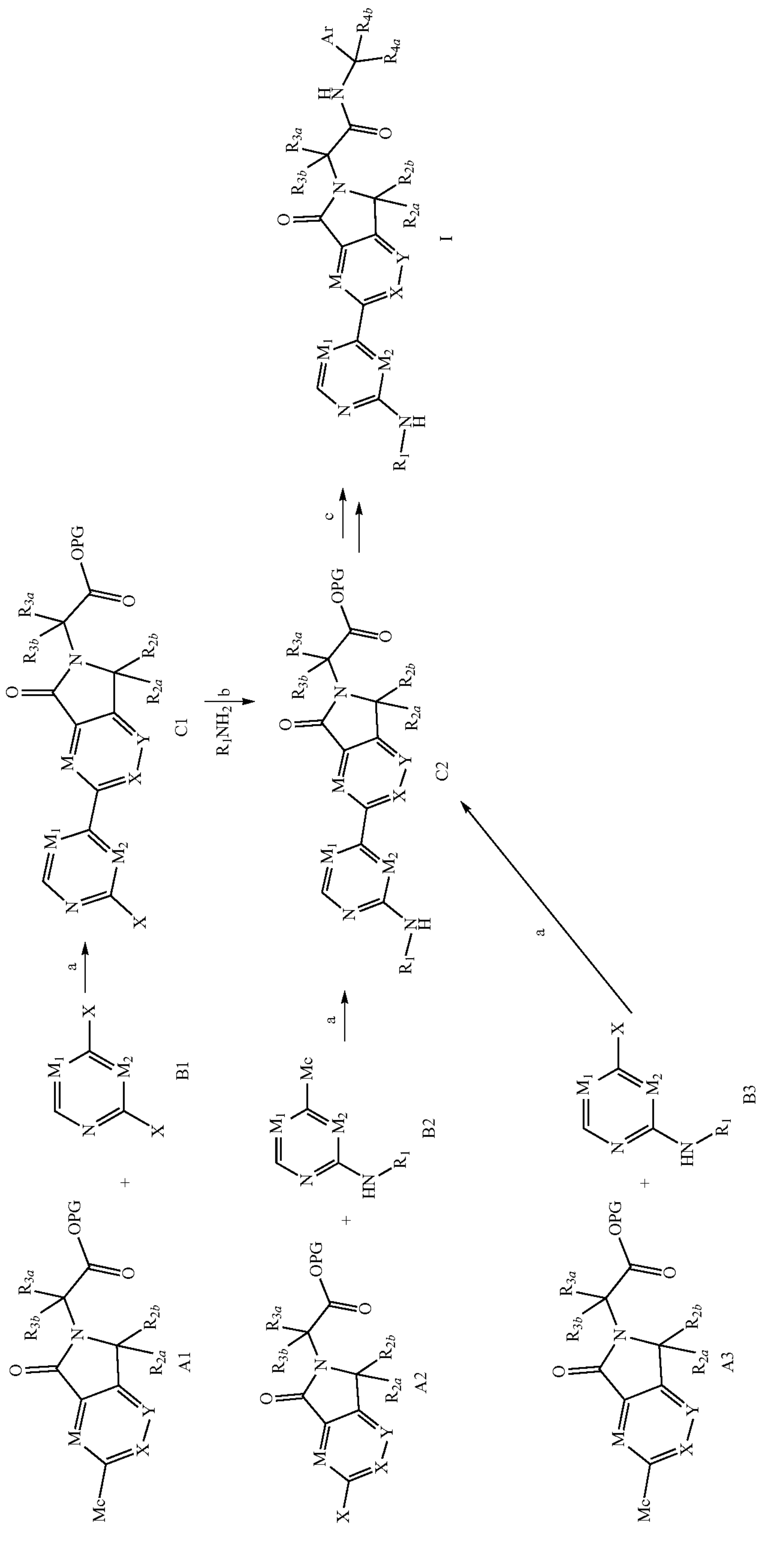
a
a
a
$R_1NH_2$ b
c

In each formula, Mc represents boric acid, borate, organotin, organozinc, etc.; X represents halogen, sulfonate, etc.; PG represents a common carboxylic acid protecting group such as methyl, ethyl, tert-butyl, benzyl, etc., and the other groups are defined as above;

preferably, the steps a), b), c) are each carried out in a solvent, and the solvent is selected from the group consisting of water, methanol, ethanol, isopropanol, butanol, ethylene glycol, ethylene glycol methyl ether, N-methylpyrrolidone, dimethylsulfoxide, tetrahydrofuran, toluene, dichloromethane, 1,2-dichloroethane, acetonitrile, N,N-dimethylformamide, N,N-dimethylacetamide, dioxane, or a combination thereof.

Preferably, the transition metal catalyst is selected from the group consisting of tris(dibenzylideneacetone)dipalladium ($Pd_2(dba)_3$), tetrakis(triphenylphosphine)palladium ($Pd(PPh_3)_4$), palladium acetate, palladium chloride, bis(triphenylphosphine)palladium dichloride, palladium trifluoroacetate, bis(triphenylphosphinepalladium) acetate, [1,1'-bis(diphenylphosphino)ferrocene]palladium dichloride, dichlorobis(tri-o-tolylphosphine)palladium, [1,2-bis(diphenylphosphino)ethane]dichloropalladium, or a combination thereof, the catalyst ligand is selected from the group consisting of tri-tert-butylphosphine, tri-tert-butylphosphine tetrafluoroborate, tri-n-butylphosphine, triphenylphosphine, tri-p-tolylphosphine, tricyclohexylphosphine, tri(o-tolyl)phosphine, or a combination thereof.

Preferably, an inorganic base is selected from the group consisting of sodium hydride, potassium hydroxide, sodium acetate, potassium acetate, potassium tert-butoxide, sodium tert-butoxide, potassium fluoride, cesium fluoride, potassium phosphate, potassium carbonate, potassium bicarbonate, sodium carbonate, sodium bicarbonate, or a combination thereof, an organic base is selected from the group consisting of pyridine, triethylamine, N,N-diisopropylethylamine, 1,8-diazabicyclo[5.4.0]undec-7-ene (DBU), lithium hexamethyldisilazane, sodium hexamethyldisilazane, dimethylpyridine, or a combination thereof.

Preferably, the acid is selected from the group consisting of hydrochloric acid, sulfuric acid, nitric acid, methanesulfonic acid, benzenesulfonic acid, p-toluenesulfonic acid, camphorsulfonic acid, etc., or a combination thereof.

Preferably, the combination of condensing agents is selected from the group consisting of DCC (dicyclohexylcarbodiimide), DIC (diisopropylcarbodiimide), CDI (carbonyldiimidazole), EDCI (1-ethyl-3-(3-dimethylaminopropyl)carbodiimide), HOAt (1-hydroxy-7-azabenzotriazole), HOBt (1-hydroxybenzotriazole), BOP (Castros reagent), PyBOP (1H-benzotriazol-1-yloxytripyrrolidinophosphonium hexafluorophosphate), HATU (2-(7-azabenzotriazol-1-yl)-N,N,N',N'-tetramethyluronium hexafluorophosphate), TBTU (0-(benzotriazol-1-yl)-N,N,N',N'-tetramethyluronium tetrafluoroborate), etc., or a combination thereof.

In the third aspect, the present disclosure provides a pharmaceutical composition, comprising (i) the compound represented by formula (I), the pharmaceutically acceptable salt thereof, the enantiomer thereof, the diastereomer thereof, the tautomer thereof, the solvate thereof or the polymorph thereof, and (ii) a pharmaceutically acceptable carrier. A dose of the compound represented by the formula (I), the pharmaceutically acceptable salt thereof, the enantiomer thereof, the diastereomer thereof, the tautomer thereof, the solvate thereof or the polymorph thereof can be a therapeutic effective amount.

In another preferred embodiment, the pharmaceutical composition is a pharmaceutical composition for preventing and/or treating diseases related to ERK kinase.

In another preferred embodiment, the pharmaceutical composition is a pharmaceutical composition for preventing and/or treating a tumor, comprising (i) the compound represented by formula (I), the pharmaceutically acceptable salt thereof, the enantiomer thereof, the diastereomer thereof, the tautomer thereof, the solvate thereof or the polymorph thereof, and (ii) a pharmaceutically acceptable carrier; wherein, the tumor comprises, but is not limited to non-small cell lung cancer, small cell lung cancer, melanoma, lung adenocarcinoma, lung squamous cell carcinoma, breast cancer, prostate cancer, liver cancer, pancreatic cancer, skin cancer, stomach cancer, bowel cancer (e.g., colon cancer), cholangiocarcinoma, brain cancer, leukemia, lymphoma or nasopharyngeal carcinoma.

In another preferred embodiment, the pharmaceutical composition is a pharmaceutical composition for preventing and/or treating an inflammatory/autoimmune disease, comprising (i) the compound represented by formula (I), the pharmaceutically acceptable salt thereof, the enantiomer thereof, the diastereomer thereof, the tautomer thereof, the solvate thereof or the polymorph thereof, and (ii) a pharmaceutically acceptable carrier; wherein the inflammatory/autoimmune disease comprises, but is not limited to, arthritis, pancreatitis, lupus erythematosus, inflammatory bowel disease, sepsis, septicemia, etc.

In the fourth aspect, the present disclosure provides a use of a substance X in the manufacture of a medicament, the substance X is the compound represented by formula (I), the pharmaceutically acceptable salt thereof, the enantiomer thereof, the diastereomer thereof, the tautomer thereof, the solvate thereof or the polymorph thereof, or the pharmaceutical composition; the medicament is a medicament for preventing and/or treating diseases related to ERK.

In a certain embodiment, the ERK can be ERK1/2.

In a certain embodiment, the disease related to ERK can be a tumor or an inflammatory/autoimmune disease.

In a certain embodiment, the tumor is non-small cell lung cancer, small cell lung cancer, melanoma, lung adenocarcinoma, lung squamous cell carcinoma, breast cancer, prostate cancer, liver cancer, pancreatic cancer, skin cancer, stomach cancer, bowel cancer (e.g., colon cancer), cholangiocarcinoma, brain cancer, leukemia, lymphoma or nasopharyngeal carcinoma.

In a certain embodiment, the inflammatory/autoimmune disease is arthritis, pancreatitis, lupus erythematosus, inflammatory bowel disease, sepsis or septicemia.

In the fifth aspect, the present disclosure provides a use of a substance X in the manufacture of an ERK inhibitor, the substance X is the compound represented by formula (I), the pharmaceutically acceptable salt thereof, the enantiomer thereof, the diastereomer thereof, the tautomer thereof, the solvate thereof or the polymorph thereof.

In a certain embodiment, the ERK can be ERK1/2.

In a certain embodiment, the ERK inhibitor is used in vitro.

The compound represented by formula (I) described in the present disclosure can inhibit various tumor cells, especially can efficiently kill tumors related to abnormal Ras-Raf-MEK-ERK signaling pathway, and act on tumor cells (such as MiaPaca-2) and will not cause p-ERK upregulation, while the existing clinical research compound BVD523 will cause p-ERK feedback upregulation when acting on MiaPaca-2. So, the compound represented by formula (I) of the present disclosure is a class of therapeutic drugs with a new mechanism of action and plays a very important role in the treatment of drug resistance in the Ras-Raf-MEK-ERK pathway.

In the sixth aspect, the present disclosure provides a method for preventing and/or treating a tumor or an inflammatory/immune disease, which comprises administering a therapeutically effective amount of a substance X to an individual in need thereof, wherein the substance X is the compound represented by formula (I), the pharmaceutically acceptable salt thereof, the enantiomer thereof, the diastereomer thereof, the tautomer thereof, the solvate thereof or the polymorph thereof, or the pharmaceutical composition.

In a certain embodiment, the tumor is non-small cell lung cancer, small cell lung cancer, melanoma, lung adenocarcinoma, lung squamous cell carcinoma, breast cancer, prostate cancer, liver cancer, pancreatic cancer, skin cancer, stomach cancer, bowel cancer (e.g., colon cancer), cholangiocarcinoma, brain cancer, leukemia, lymphoma or nasopharyngeal carcinoma.

In a certain embodiment, the inflammatory/autoimmune disease is arthritis, pancreatitis, lupus erythematosus, inflammatory bowel disease, sepsis or septicemia.

The compound represented by formula (I) described in the present disclosure can inhibit various tumor cells, especially can efficiently kill tumors related to abnormal Ras-Raf-MEK-ERK signaling pathway, and act on tumor cells (such as MiaPaca-2) and will not cause p-ERK upregulation, while the existing clinical research compound BVD523 will cause p-ERK feedback upregulation when acting on MiaPaca-2. So, the compound represented by formula (I) of the present disclosure is a class of therapeutic drugs with a new mechanism of action and plays a very important role in the treatment of drug resistance in the Ras-Raf-MEK-ERK pathway.

Terms

Unless otherwise defined, all technical terms herein have the same meaning as generally understood by those skilled in the art to which the subject of the claims are concerned. Unless otherwise indicated, all patents, patent applications, and publications cited herein are incorporated herein by reference in their entirety.

It should be understood that the foregoing brief description and the following detailed description are exemplary and only for explanation, but do not impose any limitation on the subject of the present disclosure. The singular forms used in the present disclosure include the meaning of the plural forms unless otherwise specified. It must be noted that the singular forms used in the specification and claims include the plural forms of the things indicated, unless otherwise clearly indicated herein. It should also be noted that "or", "alternatively" is used to represent "and/or" unless otherwise indicated. In addition, the terms "include", "contain", "comprise" and other forms thereof, such as "including", "containing" and "comprising" used are not restrictive.

Definitions of standard chemical terms are available in references (including Carey and Sundberg "ADVANCED ORGANIC CHEMISTRY 4TH ED." Vols. A (2000) and B (2001), Plenum Press, New York). Unless otherwise indicated, conventional methods within the technical scope of the art, such as mass spectrometry, NMR, IR and UV/VIS spectroscopy, and pharmacological methods are used. Unless specifically defined, the terms used herein in the descriptions of analytical chemistry, synthetic organic chemistry, and pharmaceutical and medicinal chemistry are known in the art. Standard techniques can be used in chemical synthesis, chemical analysis, drug preparation, formulation and delivery, and treatment of patients. For example, reaction and purification may be performed according to the manufacturer's instructions for use of the kit, or in a manner known in the art or in accordance with the specification of the present disclosure. The techniques and methods described above may generally be implemented according to conventional methods well known in the art based on the descriptions in the multiple schematic and more specific references cited and discussed in the specification. In the specification, groups and substituents thereof can be selected by those skilled in the art to provide stable structural moieties and compounds.

When a substituent is described by a conventional chemical formula written from left to right, the substituent also includes a chemically equivalent substituent obtained when the structural formula is written from right to left. For example, $-CH_2O-$ is equivalent to $-OCH_2-$.

The section headings used herein are only for the purpose of arranging the article and should not be construed as limiting the subject described above. References, in whole or in part, cited herein including but not limited to patents, patent applications, articles, books, operating manuals, and papers, are hereby incorporated by reference in their entirety.

Some chemical groups defined herein are preceded by simplified symbols to represent the total number of carbon atoms present in the groups. For example, $C_{1-6}$ alkyl refers to the alkyl with a total of 1 to 6 carbon atoms as defined below. The total number of the carbon atoms in the simplified symbol does not include carbon that may be present in a substituent of the group.

In addition to those as described above, when used in the specification and claims of the present disclosure, the following terms have the meanings as described below unless otherwise specified.

In the present disclosure, the term "halogen" refers to fluorine, chlorine, bromine, or iodine; "hydroxyl" refers to a $-OH$ group; "hydroxyalkyl" refers to the alkyl substituted by the hydroxyl ($-OH$), and the alkyl is as defined below; "carbonyl" refers to a $-C(=O)-$ group; "nitro" refers to $-NO_2$; "cyano" refers to $-CN$; "amino" refers to $-NH_2$; "substituted amino" refers to the amino substituted with one or two of the alkyl, alkylcarbonyl, arylalkyl and heteroarylalkyl as defined below, for example, monoalkylamino, dialkylamino, alkylamido, arylalkylamino, and heteroarylalkylamino; "carboxyl" refers to $-COOH$.

In the present disclosure, as a group or a part of another group (e.g., used in groups such as alkyl substituted by halogen, etc.), the term "alkyl" refers to a straight or branched hydrocarbon chain group which only consists of carbon atoms and hydrogen atoms, contains no unsaturated bonds, has, for example, 1-12 (preferably 1-8, more preferably 1-6) carbon atoms, and is linked to the rest of a molecule by a single bond. Examples of alkyl include, but are not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl, decyl, etc.

In the present disclosure, as a group or a part of another group, the term "alkenyl" refers to a straight or branched hydrocarbon chain group which only consists of carbon atoms and hydrogen atoms, contains at least one double bond, has, for example, 2-14 (preferably 2-10, more preferably 2-6) carbon atoms, and is linked to the rest of a molecule by a single bond. Examples of alkenyl include, but are not limited to, vinyl, propenyl, allyl, but-1-enyl, but-2-enyl, pent-1-enyl, pent-1,4-dienyl, etc.

In the present disclosure, as a group or a part of another group, the term "alkynyl" refers to a straight or branched hydrocarbon chain group which only consists of carbon atoms and hydrogen atoms, contains at least one triple bond and optionally one or more double bonds, has, for example, 2-14 (preferably 2-10, more preferably 2-6) carbon atoms, and is linked to the rest of a molecule by a single bond. Examples of alkynyl include, but are not limited to, ethynyl, prop-1-ynyl, but-1-ynyl, pent-1-en-4-ynyl, etc.

In the present disclosure, as a group or a part of another group, the term "cycloalkyl" refers to a stable non-aromatic monocyclic or polycyclic hydrocarbyl only consisting of carbon atoms and hydrogen atoms, wherein the cycloalkyl may include a fused ring system, a bridged ring system, or a spiro system with 3 to 15 carbon atoms, preferably 3 to 10 carbon atoms, more preferably 3 to 8 carbon atoms, and the cycloalkyl is saturated or unsaturated and may be linked to the rest of a molecule by a single bond via any suitable carbon atom. Unless otherwise specified in the specification, the carbon atoms in the cycloalkyl may optionally be oxidized. Examples of cycloalkyl include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-dihydroindenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-cyclopentadienyl, etc.

In the present disclosure, as a group or apart of another group, the term "heterocyclyl" refers to a stable 3- to 20-membered non-aromatic cyclic group consisting of 2 to 14 carbon atoms and 1 to 6 heteroatoms selected from nitrogen, phosphorus, oxygen, and sulfur. Unless otherwise specified in the specification, the heterocyclyl may be a monocyclic, bicyclic, tricyclic or more-ring system, wherein the heterocyclyl may include a fused ring system, a bridged ring system, or a spiro system; nitrogen, carbon or sulfur atom in the heterocyclyl thereof may optionally be oxidized; the nitrogen atom may optionally be quaternized; the heterocyclyl may be partially or completely saturated. The heterocyclyl may be linked to the rest of a molecule by a single bond via carbon atoms or heteroatoms. In the heterocyclyl containing a fused ring, one or more rings may be aryl or heteroaryl as defined below, provided that a junction to the rest of a molecule is a non-aromatic ring atom. For the objects of the present disclosure, the heterocyclyl is preferably a stable 4- to 11-membered non-aromatic monocyclic, bicyclic, bridged ring or spiro group containing 1 to 3 heteroatoms selected from nitrogen, oxygen and sulfur, and more preferably a stable 4- to 8-membered non-aromatic monocyclic, bicyclic, bridged ring or spiro group containing 1 to 3 heteroatoms selected from nitrogen, oxygen and sulfur. Examples of the heterocyclyl include, but are not limited to, pyrrolidinyl, morpholinyl, piperazinyl, homopiperazinyl, piperidinyl, thiomorpholinyl, 2,7-diaza-spiro[3.5]nonan-7-yl, 2-oxa-6-aza-spiro[3.3]heptan-6-yl, 2,5-diaza-bicyclo[2.2.1]heptan-2-yl, azetidinyl, pyranyl, tetrahydropyranyl, thiopyranyl, tetrahydrofuranyl, oxazinyl, dioxolane, tetrahydroisoquinolinyl, decahydroisoquinolinyl, imidazolinyl, imidazolidinyl, quinazinyl, thiazolidinyl, isothiazolidinyl, isoxazolidinyl, dihydroindolyl, octahydroindolyl, octahydroisoindolyl, pyrrolidinyl, pyrazolidinyl, phthalimido, etc.

In the present disclosure, as a group or a part of another group, the term "aryl" refers to a conjugated hydrocarbon ring system group with 6 to 18 carbon atoms (preferably 6 to 10 carbon atoms). For the object of the present disclosure, the aryl may be a monocyclic, bicyclic, tricyclic or more-ring system, or may be fused to the cycloalkyl or heterocyclyl as defined above, provided that the aryl is linked to the rest part of a molecule by a single bond via atoms on the aromatic ring. Examples of the aryl include, but are not limited to, phenyl, naphthyl, anthryl, phenanthryl, fluorenyl, 2,3-dihydro-1H-isoindolyl, 2-benzoxazolidone, 2H-1,4-benzoxazin-3(4H)-one-7-yl, etc.

In the present disclosure, the term "arylalkyl" refers to the alkyl as defined above which is substituted with the aryl as defined above.

In the present disclosure, as a group or a part of another group, the term "heteroaryl" refers to a 5- to 16-membered conjugated ring group with 1 to 15 carbon atoms (preferably 1 to 10 carbon atoms) and 1 to 6 heteroatoms selected from nitrogen, oxygen and sulfur in the ring. Unless otherwise specified in the specification, the heteroaryl may be a monocyclic, bicyclic, tricyclic or more-ring system, or may be fused to the cycloalkyl or heterocyclyl as defined above, provided that the heteroaryl is linked to the rest part of a molecule by a single bond via atoms on the aromatic ring. Nitrogen, carbon or sulfur atoms in the heteroaryl may optionally be oxidized; the nitrogen atoms may optionally be quaternized. For the objects of the present disclosure, the heteroaryl is preferably a stable 5- to 12-membered aromatic group containing 1 to 5 heteroatoms selected from nitrogen, oxygen and sulfur, and more preferably a stable 5- to 10-membered aromatic group containing 1 to 4 heteroatoms selected from nitrogen, oxygen and sulfur or a 5- to 6-membered aromatic group containing 1 to 3 heteroatoms selected from nitrogen, oxygen and sulfur. Examples of the heteroaryl include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indazinyl, isoindolyl, indazolyl, isoindazolyl, purinyl, quinolyl, isoquinolyl, diazanaphthyl, naphthyridinyl, quinoxalinyl, pteridinyl, carbazolyl, carbolinyl, phenanthridinyl, phenanthrolinyl, acridyl, phenazinyl, isothiazolyl, benzothiazolyl, benzothiophenyl, oxotriazolyl, cinnolinyl, quinazolyl, phenylthio, pyrrocolinyl, o-phenanthrolinyl, isoxazolyl, phenoxazinyl, phenothiazinyl, 4,5,6,7-tetrahydrobenzo[b]thienyl, naphthopyridyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, etc.

In the present disclosure, the term "heteroarylalkyl" refers to the alkyl as defined above, which is substituted by the heteroaryl as defined above.

In the present disclosure, "optional" or "optionally" indicates that an event or condition described herein below may or may not occur, and the description includes both the presence and absence of the event or condition at the same time. For example, "optionally substituted aryl" indicates that the aryl is substituted or unsubstituted, and the description includes both the substituted aryl and the unsubstituted aryl at the same time.

In the present disclosure, the term "moiety", "structure moiety", "chemical moiety", "group", or "chemical group" refers to a particular segment or functional group in a molecule. A chemical moiety is generally considered to be a chemical entity embedded in or attached to a molecule.

"Stereoisomer" refers to a compound which consists of the same atoms bonded by the same bonds, but with different three-dimensional structures. The present disclosure covers various stereoisomers and mixtures thereof.

When the olefinic double bond is contained in the compound of the present disclosure, the compound of the present disclosure is intended to encompass both the E- and Z-geometric isomers, unless otherwise specified.

"Tautomer" refers to an isomer formed by transferring a proton from an atom of a molecule to another atom of the same molecule. All tautomeric forms of the compound of the present disclosure are included within the scope of the present disclosure.

The compound of the present disclosure or the pharmaceutically acceptable salt thereof may contain one or more chiral carbon atoms and thus may yield an enantiomer, a diastereoisomer, and other stereoisomeric forms. Each chiral carbon atom may be defined as (R)- or (S)- based on stereochemistry. The present disclosure is intended to include all possible isomers, as well as racemic and optically pure forms thereof. A racemate, a diastereomer or an enantiomer may be selected as raw materials or intermediates for the preparation of the compound of the present disclosure. Optically active isomers can be prepared using chiral synthons or chiral reagents, or resolved using conventional techniques such as crystallization and chiral chromatography.

Conventional techniques for preparing/separating individual isomers include chiral synthesis from suitable optically pure precursors, or resolution of racemates (or racemates of salts or derivatives) using, for example, chiral high performance liquid chromatography, for example, see Gerald Gub (I) tz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

In the present disclosure, the term "pharmaceutically acceptable salt" includes a pharmaceutically acceptable acid addition salt and a pharmaceutically acceptable base addition salt.

"Pharmaceutically acceptable acid addition salt" refers to a salt formed with an inorganic acid or an organic acid and can retain the biological effectiveness of a free base without other side effects, wherein the inorganic acid salt includes, but is not limited to, hydrochloride, hydrobromide, sulfate, nitrate, phosphate, etc.; the organic acid salt includes, but is not limited to, formate, acetate, 2,2-dichloroacetate, trifluoroacetate, propionate, hexanoate, caprylate, decanoate, undecylenate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, methanesulfonate, benzene sulfonate, p-tosylate, alginate, ascorbate, salicylate, 4-aminosalicylate, naphthalene disulfonate, etc. The salts can be prepared by methods known in the art.

"Pharmaceutically acceptable base addition salt" refers to a salt formed with an inorganic base or an organic base and can retain the biological effectiveness of a free acid without other side effects. Salts derived from the inorganic base include, but are not limited to, sodium salts, potassium salts, lithium salts, ammonium salts, calcium salts, magnesium salts, iron salts, zinc salts, copper salts, manganese salts, aluminum salts, etc. Preferred inorganic salts are the ammonium salts, the sodium salts, the potassium salts, the calcium salts and the magnesium salts. Salts derived from the organic base include, but are not limited to, the following salts of primary, secondary and tertiary amines, substituted amines including naturally substituted amines, cyclic amines, and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, etc. Preferred organic bases include isopropylamine, diethylamine, ethanolamine, trimethylamine, dicyclohexylamine, choline, and caffeine. The salts can be prepared by methods known in the art.

"Polymorph" refers to different solid crystalline phases of some compounds of the present disclosure in the solid state due to the presence of two or more different molecular arrangements. Some compounds of the present disclosure may be present in more than one crystalline form, and the present disclosure is intended to include various crystal forms and mixtures thereof.

Typically, crystallization may produce a solvate of the compound of the present disclosure. The term "solvate" used in the present disclosure refers to an aggregate containing one or more molecules of the compound of the present disclosure and one or more molecules of a solvent, wherein the solvent may be water, in which case the solvate is a hydrate. Alternatively, the solvent may be an organic solvent. Thus, the compound of the present disclosure may be present in hydrates, including monohydrates, dihydrates, hemihydrates, sesquihydrates, trihydrates, tetrahydrates, etc., and corresponding solvated forms. The compound of the present disclosure can form a true solvate, but in some cases, the compound can also retain only indeterminate water or a mixture of water and a part of indeterminate solvent. The compound of the present disclosure may be reacted in the solvent or precipitated or crystallized from the solvent. The solvate of the compound of the present disclosure is also included within the scope of the present disclosure.

The present disclosure further comprises a prodrug of the compound described above. In the present disclosure, the term "prodrug" indicates a compound can be converted under physiological conditions or by solvolysis to a bioactive compound of the present disclosure. Therefore, the term "prodrug" refers to a pharmaceutically acceptable metabolic precursor of the compound of the present disclosure. When the prodrug is administered to an individual in need, the prodrug may be inactive but is converted into the active compound of the present disclosure in vivo. The prodrug is usually converted rapidly in vivo to produce the parent compound of the present disclosure, for example, by hydrolysis in the blood. The prodrug compound generally provides the advantages of solubility, histocompatibility, or sustained release in mammalian organisms. The prodrug includes known amino protective groups and carboxyl protective groups. For specific preparation method for the prodrug, refer to Saulnier, M. G., et al., Bioorg. Med. Chem. Lett. 1994, 4, 1985-1990; Greenwald, R. B., et al., J. Med. Chem. 2000, 43, 475.

In the present disclosure, "pharmaceutical composition" refers to a formulation of the compound of the present disclosure and a medium generally accepted in the art for delivering a bioactive compound to a mammal (e.g., human). The medium includes a pharmaceutically acceptable carrier. The object of the pharmaceutical composition is to promote the administration of an organism, and facilitate the absorption of active ingredients, thereby exerting the bioactivity.

In the present disclosure, the term "pharmaceutically acceptable" used herein refers to a substance (e.g., a carrier or a diluent) that does not affect the bioactivity or nature of the compound of the present disclosure and is relatively nontoxic, i.e., the substance can be administered to an individual without causing any adverse biological reactions or interacting adversely with any component contained in the composition.

In the present disclosure, the term "pharmaceutically acceptable carrier" includes but is not limited to, any adjuvants, excipients, fluidizers, sweeteners, diluents, preservatives, dyes/colorants, flavoring agents, surfactants, wetting agents, dispersants, suspensions, stabilizers, isotonic agents, solvents, or emulsifiers, which are licensed by the relevant government authorities to be acceptable for use in humans or livestocks.

In the present disclosure, the terms such as "tumor", "diseases associated with abnormal cell proliferation" of the present disclosure include, but are not limited to, leukemia, gastrointestinal stromal tumor, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell cancer, cervical cancer, ovarian cancer, intestinal cancer, nasopharyngeal cancer, brain cancer, bone cancer, esophageal cancer, melanoma, renal cancer, buccal cavity cancer, etc.

In the present disclosure, the terms "prevention", "prevent", and "preventing" used herein include reduction of the possibility of occurrence or exacerbation of diseases or conditions to patients.

In the present disclosure, the term "treatment" and other similar synonyms include the following meanings:

(I) Preventing the occurrence of diseases or conditions in the mammals, especially when such mammals are susceptible to such diseases or conditions but have not been diagnosed with the diseases or conditions;

(II) inhibiting the diseases or conditions, i.e., restraining the development of the diseases or conditions;

(III) alleviating the diseases or conditions, i.e., resolving the diseases or conditions; or (IV) relieving symptoms caused by the diseases or conditions.

In the present disclosure, the terms "effective amount", "therapeutically effective amount" or "pharmaceutically effective amount" used herein refer to an amount of at least one agent or compound sufficient to alleviate one or more symptoms of the disease or condition being treated to a certain extent after administration. The outcome may be a resolution and/or remission of signs, symptoms or etiology, or any other desired change in a biological system. For example, the "effective amount" for treatment refers to an amount of the composition containing the compound disclosed herein that is required to provide a clinically significant remission effect. The effective amount suitable for any individual case may be determined using techniques such as dose escalation trials.

In the present disclosure, the terms "taking", "administering", "administration", etc. used herein refer to methods capable of delivering the compound or the composition to a desired site for a biological action. The methods include, but are not limited to, oral route, transduodenal route, parenteral injection (including intravenous, subcutaneous, intraperitoneal, intramuscular, intraarterial injection or infusion), topical administration, and transrectal administration. Those skilled in the art are familiar with administration techniques that can be used for the compound and methods described herein, for example, techniques discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compound and the composition discussed herein are administered orally.

In the present disclosure, the term "pharmaceutical compositions", "combination medication", "administration of other therapies", or "administration of other therapeutic agents", used herein refer to a drug therapy obtained by mixing or combining more than one active ingredient, including fixed and unfixed combinations of active ingredients. The term "fixed combination" refers to the simultaneous administration of at least one compound described herein and at least one synergistic agent to a patient in the form of a single entity or a single dosage form. The term "unfixed combination" refers to the simultaneous administration, co-administration, or sequential administration in turn of at least one compound and at least one synergistic formulation described herein to a patient in the form of a separate entity. The terms are also applied in the cocktail therapy, for example by administering three or more active ingredients.

Those skilled in the art should also understand that in the methods described below, a functional group of the intermediate compound may need to be protected by an appropriate protective group. Such functional group includes hydroxyl, amino, mercapto and carboxylic acid. Appropriate hydroxyl protective groups include trialkylsilyl or diarylalkylsilyl (e.g., tert-butyldimethylsilyl, tert-butyldiphenylsilyl or trimethylsilyl), tetrahydropyranyl, benzyl, etc. Appropriate amino, amidino and guanidino protective groups include tert-butoxycarbonyl, benzyloxycarbonyl, etc. Appropriate mercapto protective groups include —C(O)—R (wherein "R" is alkyl, aryl or arylalkyl), p-methoxybenzyl, triphenylmethyl, etc. Appropriate carboxyl protective groups include alkyl, aryl or arylalkyl esters.

The protective groups may be introduced and removed in accordance with standard techniques known to those skilled in the art and described herein. The use of the protective groups is detailed in Greene, T. W. and P. G. M. Wuts, Protective Groups in Organic Synthesis, (1999), 4th Ed., Wiley. The protective group may also be a polymer resin.

It should be understood that within the scope of the present disclosure, the technical features of the present disclosure described above and the technical features specifically described below (e.g., embodiments) can be combined with each other to form new or preferred technical schemes. Due to the limitation of space, they will not be enumerated herein one by one.

On the premise of not violating the general knowledge in the art, the above preferred conditions can be arbitrarily combined to obtain preferred embodiments of the present disclosure.

The reagents and raw materials used in the present disclosure are commercially available.

The positive effects of the present disclosure lie in that: The prepared compound represented by formula (I) has a novel structure and a good ERK1/2 kinase inhibitory activity, and the compound has a specific inhibitory effect on ERK1/2 kinase at a very low concentration (less than or equal to 10 nmol/L), and demonstrates quite excellent cell proliferation inhibitory activity related to Ras-Raf-MEK-ERK; the compound represented by formula (I) of the present disclosure can inhibit various tumor cells, especially can efficiently kill tumors related to abnormal Ras-Raf-MEK-ERK signaling pathway, and act on tumor cells (such as MiaPaca-2) and will not cause p-ERK upregulation, while the existing clinical research compound BVD523 will cause p-ERK feedback upregulation when acting on MiaPaca-2. So, the compound represented by formula (I) of the present disclosure is a class of therapeutic drugs with a new mechanism of action and plays a very important role in the treatment of drug resistance in the Ras-Raf-MEK-ERK pathway, and can be used for treating diseases associated with mutation or abnormal expression of Ras-Raf-MEK-ERK kinase, such as tumors or inflammation or autoimmune diseases.

DETAILED DESCRIPTION OF THE PREFERRED EMBODIMENTS

Preparation Method I of Intermediate: Preparation of Pyrido Five-Membered Lactam Intermediate A1: tert-Butyl (R)-2-(2-chloro-7-oxo-5,7-dihydro-6H-pyrrolo[3,4-b]pyridin-6-yl)propanoate

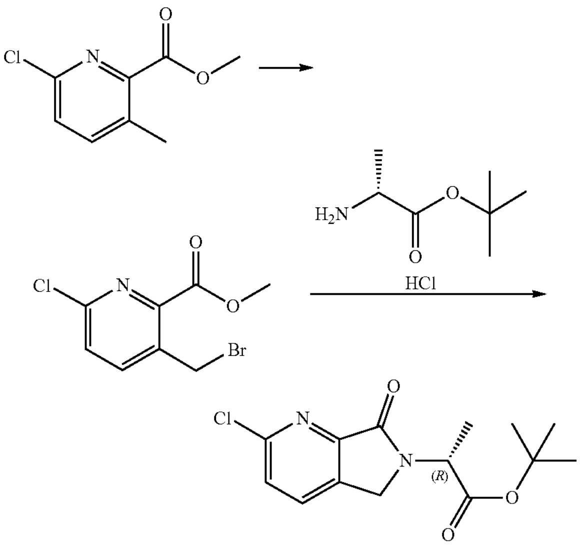

Step 1: Compound methyl 6-chloro-3-methylpicolinate (4.5 g, 24.2 mmol) was dissolved in carbon tetrachloride ($CCl_4$) (90 mL), and N-bromosuccinimide (NBS) (4.3 g, 24.2 mmol) and azobisisobutyronitrile (AIBN) (397 mg, 2.42 mmol) were added thereto under the protection of nitrogen, and the reaction solution was heated to 80° C. and reacted overnight. The reaction was cooled down, and quenched with water, and then concentrated under reduced pressure, and the mixture was extracted with petroleum ether and washed with water. The organic phase was washed once with saturated brine, dried over anhydrous sodium sulfate, and subjected to column chromatography (petroleum ether) to obtain methyl 3-(bromomethyl)-6-chloropicolinate as a white solid (4.85 g). LC-MS $[M+H]^+$: m/z 266.3. $^1H$ NMR (400 MHz, DMSO-$d_6$): δ8.15 (d, J=8.0 Hz, 1H), 7.79 (d, J=8.4 Hz, 1H), 4.95 (s, 2H), 3.93 (s, 3H).

Step 2: Compound 3-(bromomethyl)-6-chloropicolinate (5.1 g, 19.4 mmol) was dissolved in methanol (MeOH) (200 mL), and D-alanine tert-butyl ester (17.6 g, 97.1 mmol), N,N-diisopropylethylamine (DIEA) (32 mL, 194 mmol) were added thereto, and the reaction solution was reacted overnight at room temperature under the protection of nitrogen. The mixture was concentrated, and subjected to column chromatography (petroleum ether/ethyl acetate=5/1) to obtain compound tert-butyl (R)-2-(2-chloro-7-oxo-5,7-dihydro-6H-pyrrolo[3,4-b]pyridin-6-yl)propanoate as a white solid (3.88 g). LC-MS $[M+H]^+$: m/z 297.4. $^1H$ NMR (400 MHz, DMSO-$d_6$): δ8.17 (d, 1H), 7.74 (d, 1H), 4.79-4.83 (m, 1H), 4.50-4.61 (m, 2H), 1.50 (d, J=5.6 Hz, 3H), 1.39 (s, 9H).

Preparation of Intermediate A2: (R)-2-(6-Bromo-7-fluoro-1-oxoisoindolin-2-yl)propanoic acid

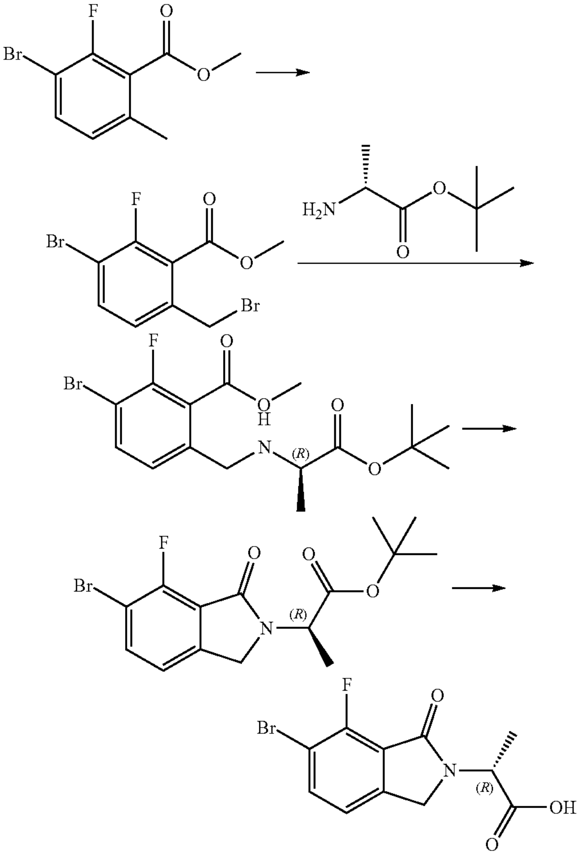

Step 1: Compound methyl 3-bromo-2-fluoro-6-methylbenzoate (5.4 g, 21.86 mmol), azobisisobutyronitrile (AIBN) (389 mg, 2.186 mmol), N-bromosuccinimide (NBS) (3.9 g, 21.86 mmol) were dissolved in carbon tetrachloride ($CCl_4$) (100 mL), and the mixture was reacted at 80° C. overnight, filtered, and washed with saturated sodium bicarbonate solution, and then washed with saturated brine. The mixture was dried, and concentrated to obtain a crude product of methyl 3-bromo-6-(bromomethyl)-2-fluorobenzoate (6.5 g), which was directly used in the next step.

Step 2: Compound methyl 3-bromo-6-(bromomethyl)-2-fluorobenzoate (6.5 g, 19.94 mmol) and D-alanine tert-butyl ester (7.24 g, 39.88 mmol) were dissolved in methanol (100 mL), and triethylamine (14 mL, 99.7 mmol) was added thereto at room temperature, then the mixture was heated to 75° C. and reacted overnight, and concentrated to obtain a crude product of methyl (R)-3-bromo-6-(((1-(tert-butoxy)-1-oxopropan-2-yl)amino)methyl)-2-fluorobenzoate as a yellow oil (5.5 g), which was directly used in the next reaction.

Step 3: The compound (5.5 g, 14.1 mmol) (the oil in the previous step) was dissolved in chlorobenzene (80 mL), and DIPEA (9.02 g, 70.51 mmol) was added thereto at room temperature, and the reaction solution was reacted under microwave irradiation at 250° C. for 2 hours, concentrated and subjected to column chromatography (volume ratio of petroleum ether/ethyl acetate PE/EA:4:1) to obtain tert-butyl (R)-2-(6-bromo-7-fluoro-1-oxoisoindolin-2-yl)propanoate as a white solid (2.7 g). LC-MS $[M+H]^+$: m/z 302.3. $^1H$ NMR (400 MHz, DMSO-$d_6$): δ7.94 (dd, J=8.0, 6.0 Hz, 1H), 7.43 (d, J=8.0 Hz, 1H), 4.72-4.75 (m, 1H), 4.53 (d, J=9.2 Hz, 2H), 1.47 (d, J=7.2 Hz, 3H), 1.39 (s, 3H).

Step 4: Compound tert-butyl (R)-2-(6-bromo-7-fluoro-1-oxoisoindolin-2-yl)propanoate (200 mg) was dissolved in dichloromethane (5 mL), then TFA (1 mL) was added thereto, and the reaction solution was stirred for 3 hours, and then concentrated to remove TFA to obtained (R)-2-(6-bromo-7-fluoro-1-oxoisoindolin-2-yl)propanoic acid as a white solid (186 mg), which was directly used in the next step. LC-MS $[M+H]^+$: m/z 303.

Embodiment 1: (R)—N—((S)-2-Hydroxy-1-(m-tolyl)ethyl)-2-(2-(2-((1-methyl-1H-pyrazol-5-yl)amino)pyridin-4-yl)-7-oxo-5,7-dihydro-6H-pyrrolo[3,4-b]pyridin-6-yl)propanamide

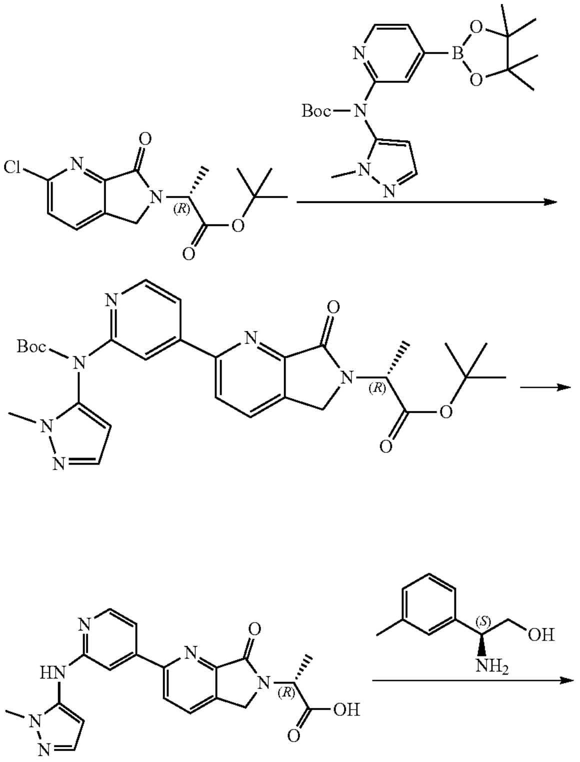

-continued

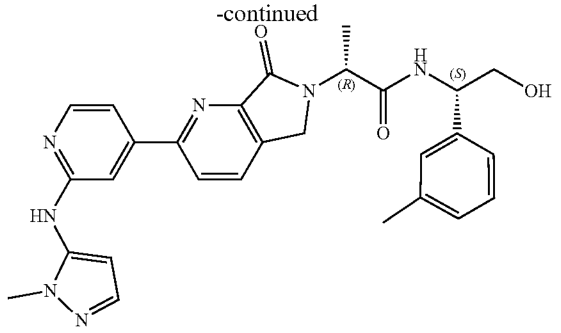

Step 1: Intermediate A1 (47 mg, 0.16 mmol) was dissolved in dioxane/water (3 mL/0.3 mL), then borate (96 mg, 0.24 mmol), sodium carbonate ($Na_2CO_3$) (51 mg, 0.48 mmol) were added thereto under the protection of nitrogen, and bis(triphenylphosphine)palladium(II) chloride [$Pd(PPh_3)_2Cl_2$] (5.6 mg, 0.01 mmol) was added thereto. The reaction solution was reacted overnight at 90° C., then cooled down, and concentrated, and then the residue was separated on a preparative plate to obtain tert-butyl (R)-2-(2-(2-((tert-butoxycarbonyl)(1-methyl-1H-pyrazol-5-yl)amino)pyridin-4-yl)-7-oxo-5,7-dihydro-6H-pyrrolo[3,4-b]pyridin-6-yl)propanoate (pale yellow solid, 36 mg). LC-MS $[M+H]^+$: m/z 535.2.

Step 2: The pale yellow solid (36 mg, 0.07 mmol) in the previous step was dissolved in dichloromethane (DCM) (3 mL), and trifluoroacetic acid (TFA) (1 mL) was added thereto, and the reaction solution was reacted overnight at room temperature under the protection of nitrogen. The mixture was concentrated, and dried to obtain (R)-2-(2-(2-((1-methyl-1H-pyrazol-5-yl)amino)pyridin-4-yl)-7-oxo-5,7-dihydro-6H-pyrrolo[3,4-b]pyridin-6-yl)propanoic acid (pale yellow oil, 62.2 mg). LC-MS $[M+H]^+$: m/z 379.1.

Step 3: The oil (25.3 mg, 0.07 mmol) in the previous step was dissolved in dimethylformamide (DMF) (3 mL), and (S)-2-amino-2-(m-tolyl)ethan-1-ol (15.1 mg, 0.1 mmol) was added thereto. Under the protection of nitrogen, 2-(7-azabenzotriazol-1-yl)-N,N,N',N'-tetramethyluronium hexafluorophosphate (HATU) (51 mg, 0.13 mmol), DIEA (36.4 mg, 0.27 mmol) were added thereto. The reaction solution was reacted overnight at room temperature, and the complete of the reaction was detected, and the target compound (yellow solid, 10.7 mg) was prepared. LC-MS $[M+H]^+$: m/z 512.2. $^1H$-NMR (400 MHz, DMSO-$d_6$): δ 9.18 (s, 1H), 8.55 (d, J=8.0 Hz, 1H), 8.19-8.27 (m, 3H), 7.70 (s, 1H), 7.49 (d, J=8.0 Hz, 1H), 7.19-7.23 (m, 1H), 7.04-7.11 (m, 3H), 6.34 (d, J=7.2 Hz, 1H), 5.03-5.09 (m, 1H), 4.78-4.81 (m, 1H), 4.74-4.76 (d, 1H), 4.59-4.60 (m, 1H), 3.72 (s, 3H), 3.60-3.65 (m, 2H), 3.35-3.39 (m, 1H), 2.29 (s, 3H), 1.44 (d, J=5.6 Hz, 3H).

Embodiment 2: (R)-2-(2-(5-Chloro-2-((tetrahydro-2H-pyran-4-yl)amino)pyrimidin-4-yl)-7-oxo-5,7-dihydro-6H-pyrrolo[3,4-b]pyridin-6-yl)-N—((S)-2-hydroxy-1-(m-tolyl)ethyl)propanamide

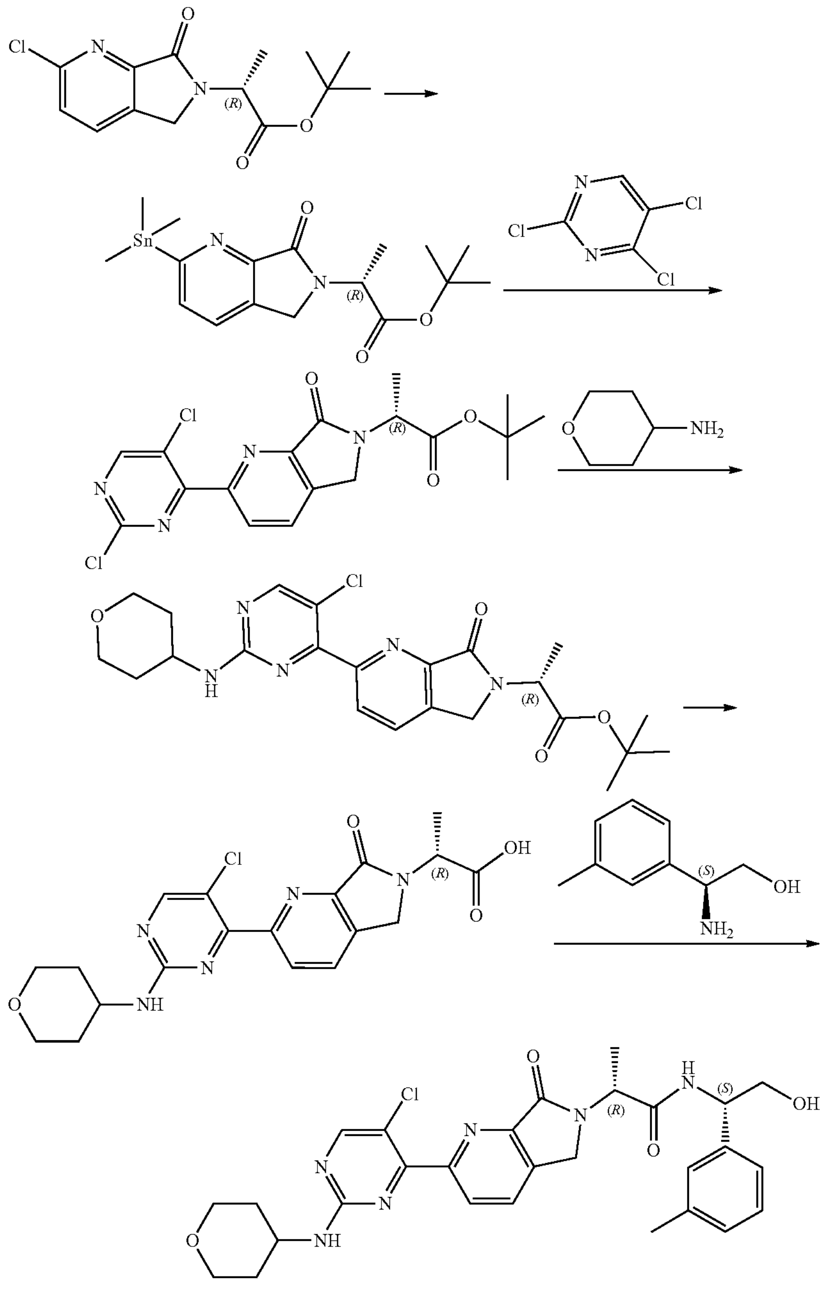

Step 1, step 2: Intermediate A1 (200 mg, 0.68 mmol) was dissolved in dioxane (3 mL), and hexamethylditin (221 mg, 0.68 mmol) was added thereto, and tetrakis(triphenylphosphine)palladium [$Pd(PPh_3)_4$] (55 mg, 0.07 mmol) was added thereto, and the reaction solution was reacted at 100° C. for 6 hours, then cooled down, and 2,4,5-trichloropyrimidine (125 mg, 0.68 mmol), $Pd(PPh_3)_4$(58 mg, 0.05 mmol) were added thereto. Then the mixture was reacted overnight at 90° C., cooled down, wash with saturated potassium fluoride (KF) solution, and extracted twice with ethyl acetate. The mixture was dried over anhydrous sodium sulfate, and subjected to column chromatography (petroleum ether/ethyl acetate=3/1) to obtain the target compound (pale yellow solid, 25.8 mg). LC-MS$[M+H]^+$: m/z 409.3. $^1H$ NMR (400 MHz, $CDCl_3$): δ8.74 (s, 1H), 8.10 (d, J=8.0 Hz, 1H), 8.04-8.06 (m, 2H), 5.23-5.27 (m, 1H), 4.84-4.85 (m, 1H), 4.504.53 (m, 1H), 1.59 (d, J=6.8 Hz, 3H), 1.46 (s, 9H).

Step 3: The pale yellow solid (24 g, 0.06 mmol) in the previous step was dissolved in DMF (2 mL), then 4-aminopyran (8.5 mg, 0.08 mmol), DIEA (21.7 mg, 0.17 mmol)

were added thereto. Under the protection of nitrogen, the reaction solution was reacted overnight at 65° C. The mixture was concentrated to obtain a crude product of compound tert-butyl (R)-2-(2-(5-chloro-2-((tetrahydro-2H-pyran-4-yl)amino)pyrimidin-4-yl)-7-oxo-5,7-dihydro-6H-pyrrolo[3,4-b]pyridin-6-yl)propanoate as a yellow solid (40 mg), which was used in the next step. LC-MS $[M+H]^+$: m/z 474.1.

Step 4, step 5: These steps were synthesized according to the methods of step 3, step 4 of embodiment 1 to obtain the target compound (white solid, 6.3 mg). LC-MS $[M+H]^+$: m/z 551.1. $^1H$ NMR (400 MHz, $CDCl_3$): δ8.52 (s, 1H), 7.87 (s, 1H), 7.21 (d, J=8.0 Hz, 1H), 7.13-7.16 (m, 2H), 7.08 (d, J=8.4 Hz, 1H), 5.28-5.31 (m, 1H), 4.96-5.05 (m, 2H), 5.22-5.24 (m, 1H), 4.11-4.14 (m, 1H), 4.02-4.03 (m, 2H), 3.85-3.90 (m, 1H), 3.74-3.75 (m, 1H), 3.51-3.55 (m, 2H), 2.35 (s, 3H), 2.09 (m, 2H), 1.79 (m, 2H), 1.53 (d, J=5.6 Hz, 3H).

Embodiment 3: (R)—N—((S)-2-Hydroxy-1-(m-tolyl)ethyl)-2-(2-(5-methyl-2-((1-methyl-1H-pyrazol-5-yl)amino)pyridin-4-yl)-7-oxo-5,7-dihydro-6H-pyrrolo[3,4-b]pyridin-6-yl)propanamide

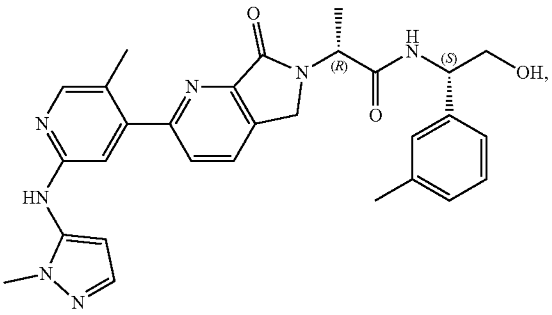

the target compound (yellow solid, 66.1 mg) was obtained according to the synthetic route of embodiment 1. LC-MS $[M+H]^+$: m/z 526.2. $^1H$ NMR (400 MHz, DMSO-$d_6$): δ 8.86 (s, 1H), 8.56 (d, J=8.2 Hz, 1H), 8.20 (d, J=8.0 Hz, 1H), 8.10 (s, 1H), 7.79 (d, J=8.0 Hz, 1H), 7.33 (d, J=7.6 Hz, 1H), 7.19-7.23 (m, 1H), 7.04-7.11 (m, 3H), 6.90 (s, 1H), 6.23-6.25 (d, 1H), 5.05-5.03 (m, 1H), 4.73-4.81 (m, 2H), 4.58-4.60 (m, 1H), 3.50-3.59 (m, 3H), 2.29 (s, 3H), 2.20 (s, 3H), 1.45 (d, J=6.4 Hz, 3H).

Embodiment 4: (R)—N—((S)-2-Hydroxy-1-(m-tolyl)ethyl)-2-(7-oxo-2-(2-((tetrahydro-2H-pyran-4-yl)amino)pyridin-4-yl)-5,7-dihydro-6H-pyrrolo[3,4-b]pyridin-6-yl)propanamide

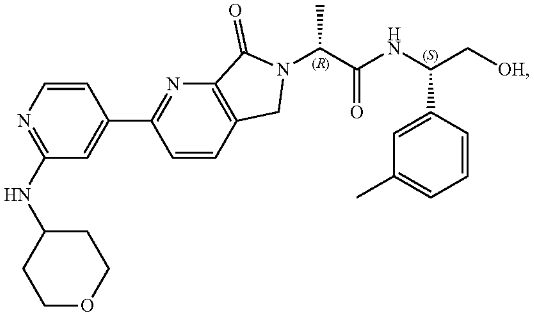

the target compound (white solid, 48.5 mg) was obtained according to the synthesis method of embodiment 1. LC-MS $[M+H]^+$: m/z 516.2. $^1H$ NMR (400 MHz, DMSO-$d_6$): 8.55 (d, J=8.0 Hz, 1H), 8.18(d, J=8.0 Hz, 1H),8.09 (s, 1H), 8.11 (s, 1H), 7.30 (s, 1H), 7.19-7.22 (i, 1H), 7.04-7.15 (m, 4H), 6.79 (d, J=6.4 Hz, 1H), 5.03-5.06 (i, 1H), 4.71-4.88 (i, 3H), 4.58 (d, J=5.6 Hz, 1H), 3.86-4.01 (m, 3H), 3.52-3.55 (i, 2H), 3.39-3.45 (m, 2H), 1.45 (d, J=6.8 Hz, 3H), 2.29 (s, 3H), 1.90-1.93 (m, 2H), 1.40-1.48 (i, 5H).

Using different commercially available reagents and intermediates A1 and A2 as raw materials, the following embodiment compounds were prepared and synthesized according to the methods of embodiment 1 and embodiment 2:

| Embodiment | Structure | Analytical data (LC-MS and $^1H$-NMR) |
|---|---|---|
| 5 | 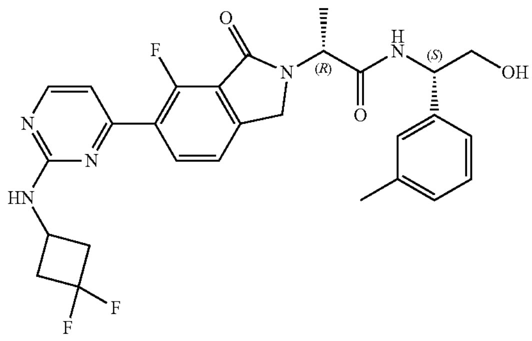 | $[M + H]^+$: m/z 540.1. (400 MHz, $CD_3OD$): δ 8.36-8.29 (m, 2H), 7.94 (dd, J = 8.0, 6.0 Hz, 1H), 7.53 (d, J = 8.0 Hz, 1H), 7.43 (d, J = 8.0 Hz, 1H), 7.35-6.94 (m, 3H), 5.31-5.33 (m, 1H), 5.01-5.07 (m, 2H), 4.49-4.53 (m, 1H), 4.38-4.42 (m, 1H), 3.90 (d, J = 9.2 Hz, 1H), 3.70 (d, J = 10.4 Hz, 1H), 3.07-3.11 (m, 2H), 2.68-2.75 (m, 3H), 2.28 (s, 3H), 1.50-1.53 (d, J = 6.4 Hz, 3H). |

-continued

| Embod-iment | Structure | Analytical data (LC-MS and $^1$H-NMR) |
|---|---|---|
| 6 | 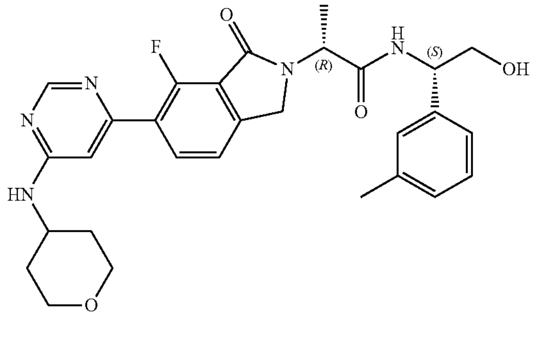 | [M + H]$^+$: m/z 533.2. (400 MHz, $CD_3OD$): 8.57 (s, 1H), 8.01 (dd, J = 8.0, 6.0 Hz, 1H), 7.51 (s, 1H), 7.48 (d, J = 8.0 Hz, 1H), 7.19-7.22 (m, 1H), 7.04-7.15 (m, 2H), 6.79 (s, 1H), 5.01-5.05 (m, 1H), 4.75-4.84 (m, 3H), 4.56 (d, J = 5.6 Hz, 1H), 3.89-4.01 (m, 3H), 3.53-3.56 (m, 2H), 3.36-3.40 (m, 2H), 1.45 (d, J = 6.8 Hz, 3H), 2.28 (s, 3H), 1.89-1.94 (m, 2H), 1.41-1.47 (m, 5H). |
| 7 | 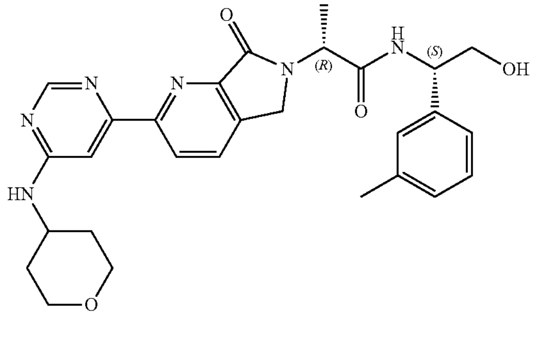 | [M + H]$^+$: m/z 517.4. (400 MHz, $CD_3OD$): 8.57 (s, 1H), 8.11 (d, J = 8.0 Hz, 1H), 7.84 (d, J = 8.0 Hz, 1H), 7.51 (s, 1H), 7.19-7.22 (m, 1H), 7.04-7.15 (m, 2H), 6.79 (s, 1H), 5.01-5.05 (m, 1H), 4.75-4.83 (m, 3H), 4.54 (d, J = 5.6 Hz, 1H), 3.89-4.00 (m, 3H), 3.52-3.56 (m, 2H), 3.36-3.41 (m, 2H), 2.44 (d, J = 6.8 Hz, 3H), 2.26 (s, 3H), 1.90-1.94 (m, 2H), 1.40-1.47 (m, 5H). |
| 8 | 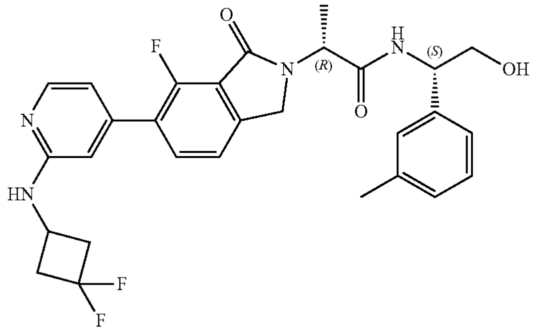 | [M + H]$^+$: m/z 539.1. (400 MHz, $CD_3OD$) δ 8.16 (d, J = 5.2 Hz, 1H), 7.76 (t, J = 7.2 Hz, 1H), 7.44-7.49 (m, 2H), 7.22 (t, J = 7.6 Hz, 1H), 7.16-7.05 (m, 2H), 6.99-7.02 (m, 1H), 6.95 (s, 1H), 5.28-5.32 (m, 1H), 5.01-5.06 (m, 2H), 4.47-4.52 (m, 1H), 4.39-4.44 (m, 1H), 3.88 (d, J = 9.2 Hz, 1H), 3.71 (d, J = 10.4 Hz, 1H), 3.05-3.10 (m, 2H), 2.67-2.73 (m, 2H), 2.41 (s, 4H), 1.50-1.54(d, J = 6.4 Hz, 3H). |
| 9 | 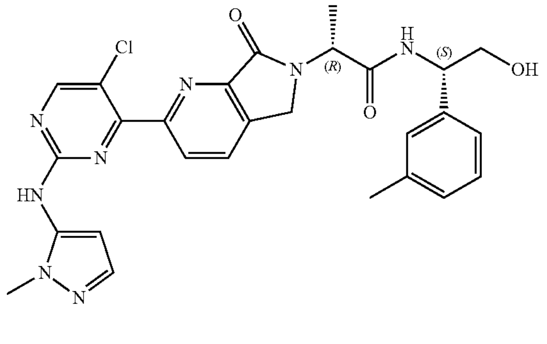 | [M + H]$^+$: m/z 547.0. (400 MHz, $CDCl_3$): δ 8.51 (s, 1H), 7.72 (d, J = 8.0 Hz, 1H), 7.33 (d, J = 7.6 Hz, 1H), 7.19-7.23 (m, 1H), 7.13-7.16 (m, 2H), 7.08 (d, J = 8.4 Hz, 1H), 7.04-7.11 (m, 1H), 6.90 (s, 1H), 5.05-5.03 (m, 1H), 4.73-4.81 (m, 2H), 4.58-4.60 (m, 1H), 3.50-3.59 (m, 2H), 2.29 (s, 3H), 2.20 (s, 3H), 1.45 (d, J = 6.4 Hz, 3H). |

-continued
| Embod-iment | Structure | Analytical data (LC-MS and $^1$H-NMR) |
|---|---|---|
| 10 | 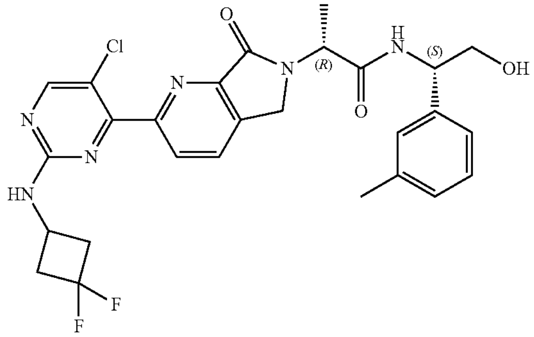 | $[M + H]^+$: m/z 557.0. (400 MHz, $CDCl_3$): δ 8.50 (s, 1H), 7.78-7.80 (m, 2H), 7.19-7.22 (m, 5H), 7.09 (d, J = 6.8 Hz, 1H), 5.31-5.33 (m, 1H), 5.01-5.07 (m, 2H), 4.49-4.53 (m, 1H), 4.38-4.42 (m, 1H), 3.90 (d, J = 9.2 Hz, 1H), 3.70 (d, J = 10.4 Hz, 1H), 3.07-3.11 (m, 2H), 2.68-2.75 (m, 3H), 2.28 (s, 3H), 1.50-1.53 (d, J = 6.4 Hz, 3H). |
| 11 | 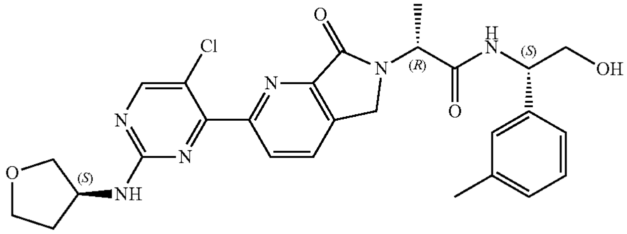 | $[M + H]^+$: m/z 537.2. (400 MHz, $CDCl_3$): δ 8.46 (s, 1H), 7.70-7.73 (m, 1H), 7.21-7.24 (m, 4H), 7.09 (d, J = 6.8 Hz, 1H), 5.30-5.32 (m, 1H), 5.04-5.09 (m, 2H), 4.63 (s, 1H), 4.44-4.49 (m, 1H), 4.02-4.09 (m, 2H), 3.82-3.94 (m, 3H), 3.69-3.71 (m, 1H), 2.36-2.40 (m, 5H), 1.50 (d, J = 6.8 Hz, 3H). |
| 12 | 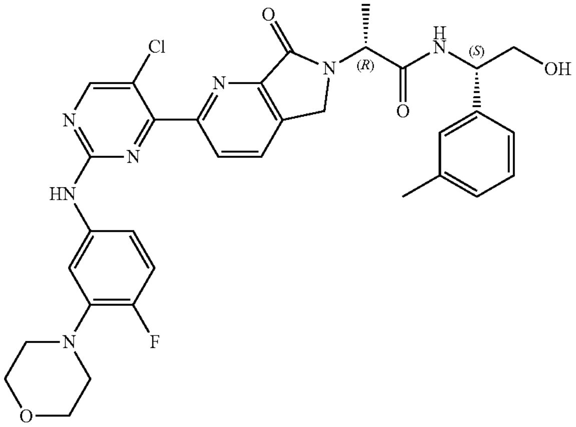 | $[M + H]^+$: m/z 646.1. (400 MHz, $CDCl_3$): δ 8.74 (s, 1H), 8.51-8.54 (m, 2H), 7.60-7.70 (m, 2H), 7.52 (s, 1H), 7.30 (d, J = 8.0 Hz, 1H), 7.18-7.25 (m, 3H), 7.01-7.09 (m, 2H), 5.34-5.36 (m, 2H), 5.11-5.16 (m, 2H), 4.42 (d, J = 5.6 Hz, 1H), 3.89-3.98 (m, 5H), 3.66-3.70 (m, 1H), 3.13 (s, 4H), 2.34 (s, 3H), 1.50 (d, J = 7.2 Hz, 3H). |
| 13 | 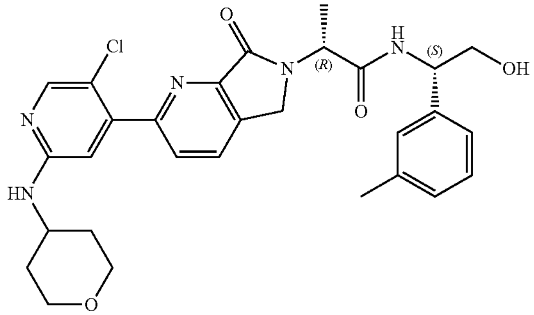 | $[M + H]^+$: m/z 550.1 |

-continued
| Embodiment | Structure | Analytical data (LC-MS and $^1$H-NMR) |
|---|---|---|
| 14 | 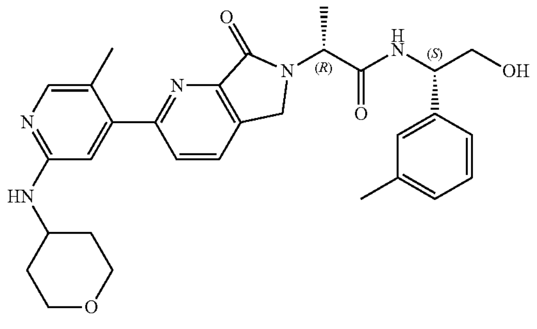 | $[M + H]^+$: m/z 530.3. (400 MHz, DMSO-$d_6$): δ 8.86 (s, 1H), 8.56 (d, J = 8.2 Hz, 1H), 8.20 (d, J = 8.0 Hz, 1H), 8.10 (s, 1H), 7.19-7.23 (m, 1H), 7.04-7.11 (m, 3H), 6.90 (s, 1H), 5.01-5.05 (m, 1H), 4.75-4.83 (m, 3H), 4.54 (d, J = 5.6 Hz, 1H), 3.89-4.00 (m, 3H), 3.52-3.56 (m, 2H), 3.36-3.41 (m, 2H), 2.26 (s, 3H), 1.90-1.94 (m, 2H), 1.40-1.45 (m, 5H). |
| 15 | 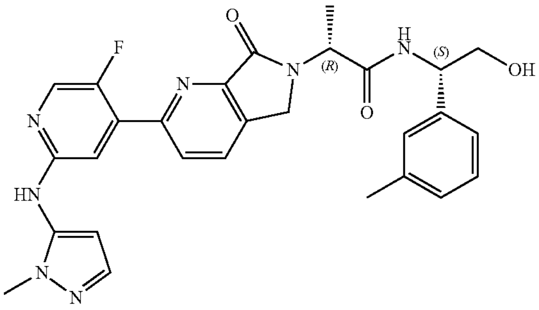 | $[M + H]^+$: m/z 530.4. |
| 16 | 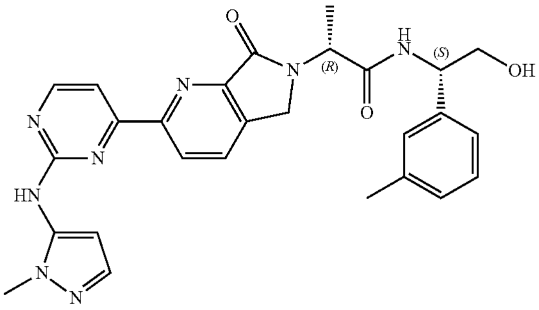 | $[M + H]^+$: m/z 513.1. |
| 17 | 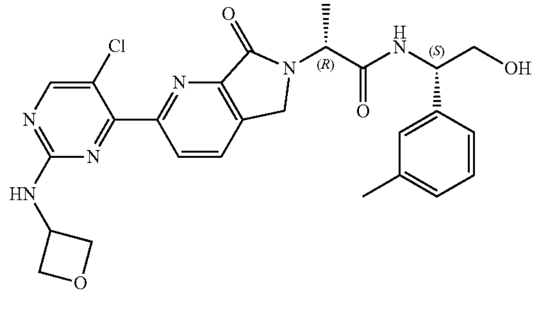 | $[M + H]^+$: m/z 523.2. (400 MHz, $CD_3OD$): δ 8.42 (s, 1H), 8.21 (d, J = 8.0 Hz, 1H), 7.97 (d, J = 8.0 Hz, 1H), 7.09-7.22 (m, 4H), 5.08-5.16 (m, 2H), 4.92-4.96 (m, 3H), 4.84 (s, 1H), 4.74 (s, 1H), 4.64-4.69 (m, 2H), 3.70-3.72 (m, 2H), 2.34 (s, 3H), 1.59 (d, J = 7.2 Hz, 3H) |
| 18 | 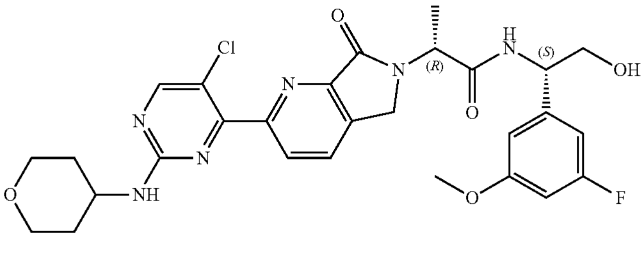 | $[M + H]^+$: m/z 585.2. (400 MHz, DMSO-$d_6$): δ 8.61 (d, J = 8.0 Hz, 1H), 8.50 (s, 1H), 8.24 (d, J = 8.0 Hz, 1H), 7.92 (d, J = 8.0 Hz, 1H), 7.68-7.71 (m, 1H), 6.68-6.74 (m, 3H), 5.02-5.07 (m, 1H), 4.94-4.96 (m, 1H), 4.79-4.83 (m, 1H), 4.61-4.74 (m, 2H), 3.85-3.94 (m, 3H), 3.76 (s, 3H), 3.53-3.55 (m, 2H), 3.34 (s, 2H), 1.82-1.85 (m, 2H), 1.46-1.57 (m, 5H) |

-continued

| Embodiment | Structure | Analytical data (LC-MS and $^1$H-NMR) |
|---|---|---|
| 19 | 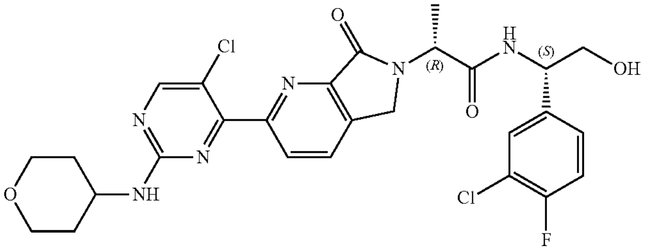 | $[M + H]^+$: m/z 589.1. (400 MHz, DMSO-$d_6$): δ 8.65 (d, J = 7.6 Hz, 1H), 8.50 (s, 1H), 8.24 (d, J = 8.0 Hz, 1H), 7.92 (d, J = 8.0 Hz, 1H), 7.66-7.70 (m, 1H), 7.51-7.54 (m, 1H), 7.30-7.41 (m, 2H), 4.96-5.06 (m, 2H), 4.82-4.87 (m, 1H), 4.60-4.72 (m, 2H), 3.85-3.95 (m, 3H), 3.54-3.57 (m, 2H), 3.34 (s, 2H), 1.83-1.85 (m, 2H), 1.41-1.57 (m, 5H) |
| 20 | 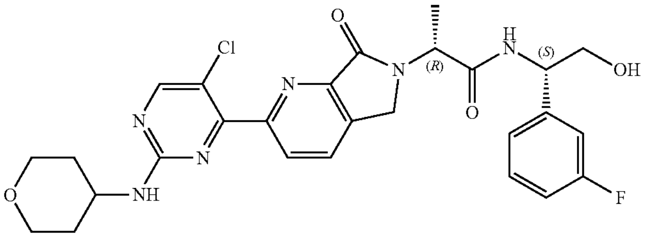 | $[M + H]^+$: m/z 555.2. (400 MHz, DMSO-$d_6$): δ 8.64 (d, J = 8.4 Hz, 1H), 8.50 (s, 1H), 8.24 (d, J = 8.0 Hz, 1H), 7.92 (d, J = 8.0 Hz, 1H), 7.69 (s, 1H), 7.34-7.40 (m, 1H), 7.05-7.16 (m, 3H), 5.02-5.08 (m, 1H), 4.95-4.98 (m, 1H), 4.84-4.89 (m, 1H), 4.61-4.78 (m, 2H), 3.85-3.92 (m, 3H), 3.55-3.58 (m, 2H), 3.41 (m, 2H), 1.82-1.85 (m, 2H), 1.44-1.57 (m, 5H) |
| 21 | 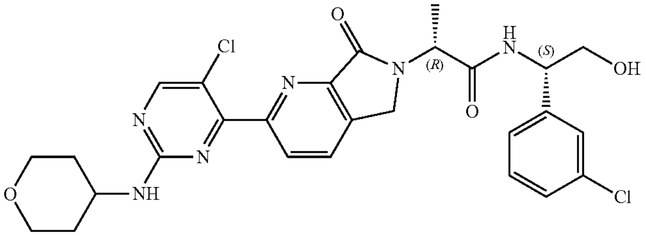 | $[M + H]^+$: m/z 571.1. (400 MHz, DMSO-$d_6$): δ 8.66 (d, J = 8.0 Hz, 1H), 8.50 (s, 1H), 8.24 (d, J = 8.0 Hz, 1H), 7.92 (d, J = 8.0 Hz, 1H), 7.69 (s, 1H), 7.27-7.38 (m, 4H), 5.02-5.07 (m, 1H), 4.96-4.99 (m, 1H), 4.82-4.87 (m, 1H), 4.60-4.78 (m, 2H), 3.82-3.95 (m, 3H), 3.55-3.58 (m, 2H), 3.34 (s, 2H), 1.82-1.85 (m, 2H), 1.44-1.57 (m, 5H) |
| 22 | 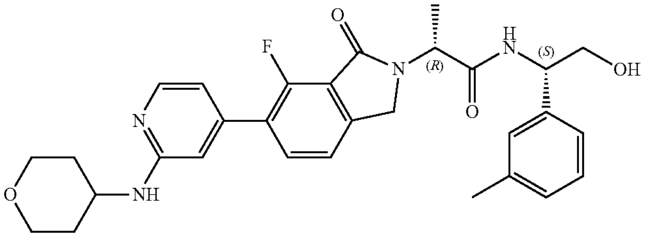 | $[M + H]^+$: m/z 533.3 (400 MHz, $CD_3OD$) δ 7.92 (s, 1H), 7.89-7.77(m, 1H), 7.57 (d, J = 7.6 Hz, 1H), 7.29-7.18 (m, 2H), 7.17-6.97 (m, 4H), 5.05-4.91 (m, 1H), 4.97-4.93 (m, 1H), 4.69-4.82 (m, 2H), 4.02 (dd, J = 2.8, 8.4 Hz, 2H), 3.94-3.82 (m, 1H), 3.80-3.65 (m, 2H), 3.61-3.48 (m, 2H), 2.34 (s, 3H), 2.09-1.95 (m, 2H), 1.69-1.65 (m, 2H), 1.56 (d, J = 7.2 Hz, 3H) |

Embodiment 23: (R)-2-(7-Fluoro-6-(2-((1-methyl-1H-pyrazol-5-yl)amino)pyridin-4-yl)-1-isoindolin-2-yl)-N—((S)-2-hydroxy-1-(m-tolyl)ethyl)propanamide

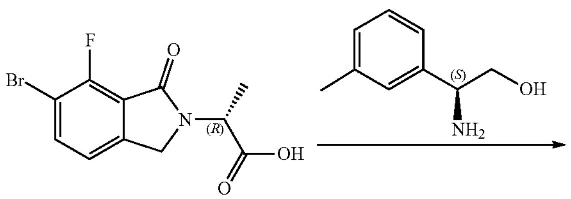

-continued

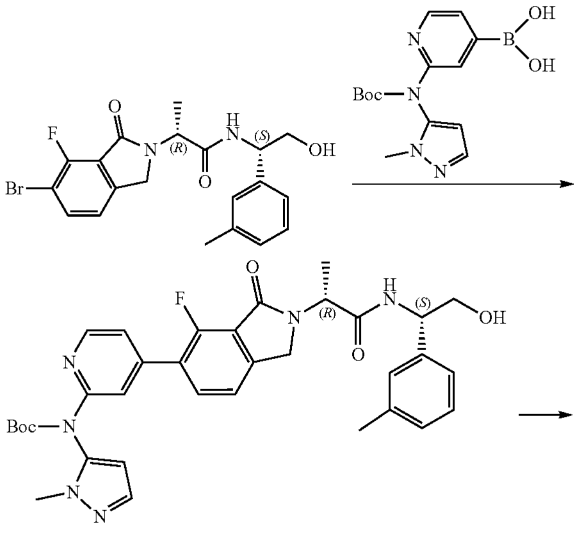

-continued

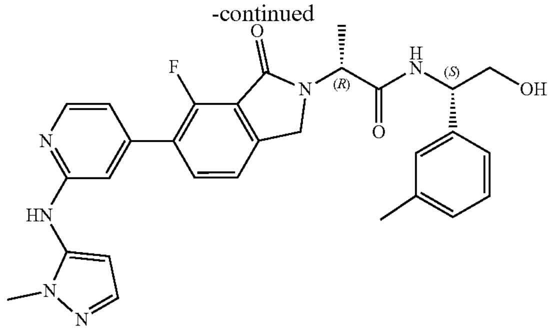

Step 1: Intermediate A2 (186 mg, 0.616 mmol) and amino alcohol raw material (111.76 mg, 0.739 mmol) were dissolved in DMF (10 mL), then 2-(7-azabenzotriazol-1-yl)-N,N,N',N'-tetramethyluronium hexafluorophosphate (HATU) (468.16 mg, 1.232 mmol) and DIPEA (0.41 mL, 2.46 mmol) was added thereto, and the reaction was stirred for 16 hours. The reaction solution was poured into 20 mL of water, and extracted with ethyl acetate (50 mL*3), then washed with saturated brine, and then dried, and the mixture was concentrated, and subjected to column chromatography (volume ratio of PE/EA:1:1) to obtain intermediate (R)-2-(6-bromo-7-fluoro-1-isoindolin-2-yl)-N—((S)-2-hydroxy-1-(m-tolyl)ethyl)propanamide (gray solid, 256 mg). LC-MS $[M+H]^+$: m/z 437.4. $^1$H-NMR (400 MHz, DMSO-$d_6$): δ 8.55 (d, J=8.4 Hz, 1H), 8.00-7.83 (m, 1H), 7.41 (d, J=8.0 Hz, 1H), 7.20 (t, J=7.2 Hz, 1H), 7.09-7.03 (m, 3H), 4.93-4.87 (m, 2H), 4.78-4.76 (m, 1H), 4.69-4.51 (dd, J=18.4, 24.0 Hz, 1H), 3.50-3.53 (m, 2H), 2.29 (s, 3H), 1.39 (d, J=7.2 Hz, 3H).

Step 2, step 3: (R)-2-(6-Bromo-7-fluoro-1-isoindolin-2-yl)-N—((S)-2-hydroxy-1-(m-tolyl)ethyl)propanamide (80 mg, 0.184 mmol) and pyridine borate raw material (76 mg, 0.24 mmol) were dissolved in dioxane/water (5 mL/1.5 mL). Under the protection of nitrogen, 1,1'-bis(di-tert-butylphosphino)ferrocene palladium dichloride (12 mg, 0.0184 mmol) and potassium phosphate ($K_3PO_4$) (59 g, 0.276 mmol) were added thereto, and the reaction solution was reacted at 90° C. for 3 hours, and poured into 300 mL of water. The mixture was extracted with ethyl acetate (500 mL*3), then washed with saturated brine, dried, and rotary evaporated to dryness to obtain a crude product, which was directly dissolved in DCM (5 mL), added with trifluoroacetic acid (1 mL), and stirred for 3 hours. The mixture was rotary evaporated to dryness and the pH was adjusted to neutral. The mixture was extracted with dichloromethane (50 mL*2), dried, concentrated, and subjected to column chromatography (volume ratio of DCM/MeOH:50:1) to obtain embodiment 23 (yellow solid, 63.5 mg). LC-MS $[M+H]^+$: m/z 529.3. $^1$H NMR (400 MHz, $CD_3OD$) δ8.16 (d, J=5.2 Hz, 1H), 7.76 (t, J=7.2 Hz, 1H), 7.44-7.49 (m, 2H), 7.22 (t, J=7.6 Hz, 1H), 7.16-7.05 (m, 3H), 6.99-7.02 (m, 1H), 6.95 (s, 1H), 6.26 (d, J=2.0 Hz, 1H), 5.04 (q, J=7.2 Hz, 1H), 4.94 (t, J=6.4 Hz, 1H), 4.80-4.64 (dd, J=18.4, 23.2 Hz, 2H), 3.80-3.61 (m, 5H), 2.33 (s, 3H), 1.55 (d, J=10.8 Hz, 3H).

Embodiment 24: (R)-2-(2-(5-Chloro-2-(isopropylamino)pyrimidin-4-yl)-7-oxo-5,7-dihydro-6H-pyrrolo[3,4-b]pyridin-6-yl)-N—((S)-2-hydroxy-1-(m-tolyl)ethyl)propanamide

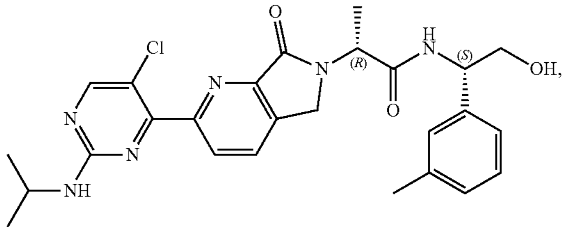

embodiment 24 (white solid, 43 mg) was prepared according to the same method of embodiment 2. LC-MS $[M+H]^+$: m/z 509.3. $^1$H NMR (400 MHz, DMSO-$d_6$) δ 8.58 (d, J=8.0 Hz, 1H), 8.48 (s, 1H), 8.23 (d, J=8.0 Hz, 1H), 7.92 (d, J=8.0 Hz, 1H), 7.52-7.55 (m, 1H), 7.18-7.22 (m, 1H), 7.04-7.15 (m, 3H), 5.03-5.08 (m, 1H), 4.59-4.82 (m, 4H), 4.01-4.03 (m, 1H), 3.53 (d, J=6.4 Hz, 2H), 2.29 (s, 3H), 1.44 (d, J=7.2 Hz, 3H), 0.84 (d, J=7.2 Hz, 6H).

Embodiment 25: (R)-2-(6-(5-Chloro-2-((tetrahydro-2H-pyran-4-yl)amino)pyrimidin-4-yl)-7-fluoro-1-oxoisoindolin-2-yl)-N—((S)-2-hydroxy-1-(m-tolyl)ethyl)propanamide

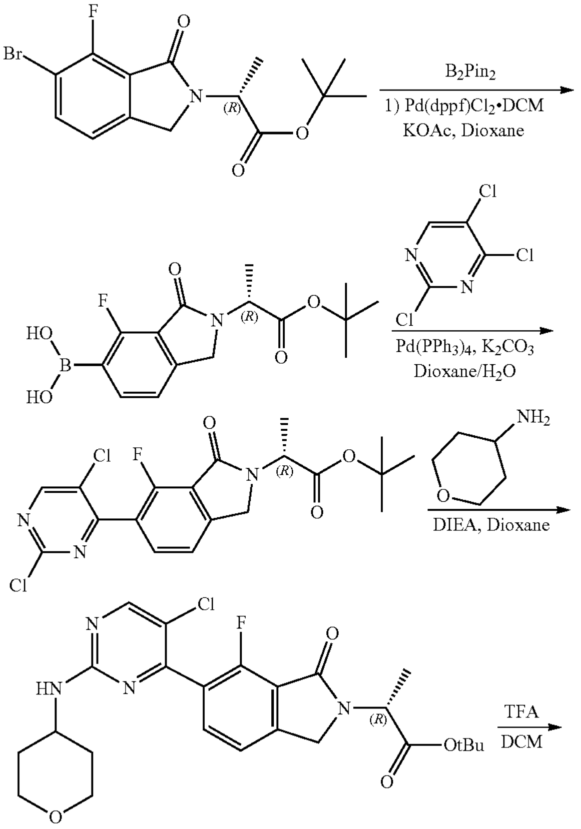

-continued

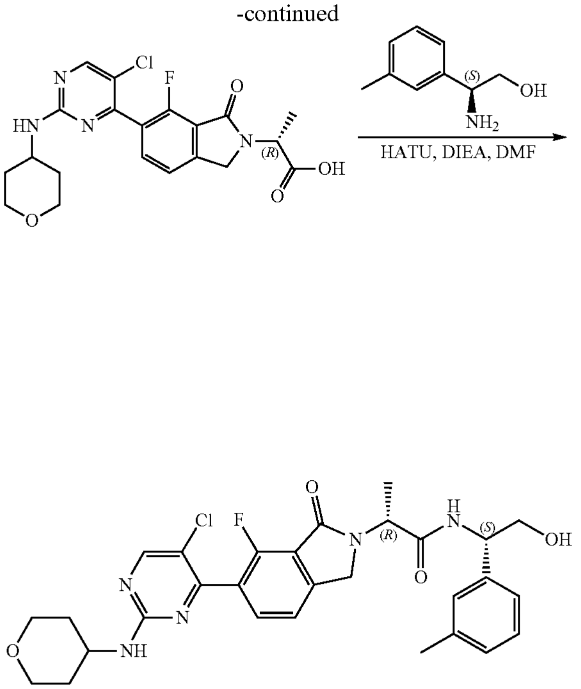

Step 1: Compound tert-butyl (R)-2-(6-bromo-7-fluoro-1-oxoisoindolin-2-yl)propanoate (2.7 g, 7.5 mmol) and pinacol borate ($B_2Pin_2$) (3.83 g, 15.1 mmol) were dissolved in dioxane (50 mL). Under the protection of nitrogen, 1,1'-bis (diphenylphosphino)ferrocene-palladium(II)dichloride dichloromethane complex Pd(dppf)$Cl_2$.DCM (306 mg, 0.375 mmol) and potassium acetate (2.2 g, 22.5 mmol) were added thereto, and the reaction solution was reacted at 110° C. for 16 hours, then poured into 300 mL of water, and then extracted with ethyl acetate (500 mL*3). The mixture was washed with saturated brine, rotary evaporated to dryness, and subjected to reversed-phase column chromatography (acetonitrile/water) to obtain (R)-(2-(1-(tert-butoxy)-1-oxopropan-2-yl)-4-fluoro-3-oxoisoindolin-5-yl)boronic acid as a yellow solid (950 mg). LC-MS $[M+H]^+$: m/z 268.0. $^1H$ NMR (400 MHz, DMSO-$d_6$): δ 8.37 (s, 2H), 7.77 (dd, J=7.4, 5.0 Hz, 1H), 7.38 (d, J=7.5 Hz, 1H), 4.75-4.71 (m, 1H), 4.57-4.45 (m, 2H), 1.47 (d, J=7.4 Hz, 3H), 1.39 (s, 9H).

Step 2: Compound (R)-(2-(1-tert-butoxy)-1-oxopropan-2-yl)-4-fluoro-3-oxoisoindolin-5-yl)boronic acid (200 mg, 0.619 mmol) and 2,4,5-trichloropyrimidine (227 mg, 1.23 mmol) were dissolved in dioxane/water (12 mL/4 mL). Under the protection of nitrogen, $Pd(PPh_3)_4$(36 mg, 0.03 mmol) and potassium carbonate ($K_2CO_3$) (171 mg, 1.24 mmol) were added thereto, and the reaction solution was reacted at 90° C. for 16 hours, concentrated and subjected to column chromatography (PE/EA=2:1) to obtain tert-butyl (R)-2-(6-(2,5-dichloropyrimidin-4-yl)-7-fluoro-1-oxoisoindolin-2-yl)propanoate as a white solid (100 mg). LC-MS $[M+H]^+$: m/z 370.2.

Step 3: Compound tert-butyl (R)-2-(6-(2,5-dichloropyrimidin-4-yl)-7-fluoro-1-oxoisoindolin-2-yl)propanoate (60 mg, 0.141 mmol), tetrahydro-2H-pyran-4-amine (42.7 mg, 0.423 mmol), DIEA (72.2 mg, 0.564 mmol) were dissolved in absolute ethanol (4 mL), and the reaction solution was reacted at 90° C. overnight, concentrated and subjected to column chromatography (PE/EA=1:1) to obtain tert-butyl (R)-2-(6-(5-chloro-2-((tetrahydro-2H-pyran-4-yl)amino)pyrimidin-4-yl)-7-fluoro-1-oxoisoindolin-2-yl)propanoate as a white solid (45.6 mg), which was directly used in the next step. LC-MS $[M+H]^+$: m/z 491.5.

Step 4: Compound tert-butyl (R)-2-(6-(5-chloro-2-((tetrahydro-2H-pyran-4-yl)amino)pyrimidin-4-yl)-7-fluoro-1-oxoisoindolin-2-yl)propanoate (45.6 mg) was dissolved in dichloromethane (3 mL), then TFA (1.5 mL) was added thereto, and the mixture was stirred for 3 hours, then concentrated to remove TFA to obtain (R)-2-(6-(5-chloro-2-((tetrahydro-2H-pyran-4-yl)amino)pyrimidin-4-yl)-7-fluoro-1-oxoisoindolin-2-yl)propanoic acid as a gray-black oil (45 mg), which was directly used in the next step. LC-MS $[M+H]^+$: m/z 435.0.

Step 5: Compound (R)-2-(6-(5-chloro-2-((tetrahydro-2H-pyran-4-yl)amino)pyrimidin-4-yl)-7-fluoro-1-oxoisoindolin-2-yl)propanoic acid (45 mg, 0.104 mmol) was dissolved in DCM (4 mL), then (S)-2-amino-2-(m-tolyl)ethan-1-ol (18.8 mg, 0.124 mmol), HATU (59.3 mg, 0.156 mmol), DIEA (53.7 mg, 0.416 mmol) were added thereto in turn, and the reaction solution was stirred overnight at room temperature for 3 hours, poured into saturated aqueous sodium carbonate solution (10 mL), and extracted with DCM (10 mL*3), and then dried over magnesium sulfate ($MgSO_4$). The mixture was filtered, concentrated and subjected to preparative column chromatography (acid method-trifluoroacetic acid) to obtain (R)-2-(6-(5-chloro-2-((tetrahydro-2H-pyran-4-yl)amino)pyrimidin-4-yl)-7-fluoro-1-oxoisoindolin-2-yl)-N—((S)-2-hydroxy-1-(m-tolyl)ethyl) propanamide as a yellow solid (24.93 mg). LC-MS $[M+H]^+$: m/z 568.2. $^1H$ NMR (400 MHz, $CD_3OD$): δ8.35 (s, 1H), 7.69 (dd, J=7.7, 6.2 Hz, 1H), 7.50 (d, J=7.8 Hz, 1H), 7.22 (t, J=7.6 Hz, 1H), 7.16 (s, 1H), 7.12 (d, J=7.6 Hz, 1H), 7.08 (d, J=7.4 Hz, 1H), 5.04-5.02 (m, 1H), 4.97-4.91 (m, 1H), 4.87-4.80 (m, 1H), 4.69-4.65 (m, 1H), 4.04-3.90 (m, 2H), 3.77-3.66 (m, 2H), 3.56-3.43 (m, 2H), 2.34 (s, 3H), 1.97 (d, J=12.5 Hz, 2H), 1.67-1.57 (m, 2H), 1.55 (d, J=7.3 Hz, 3H).

Embodiment 26: (R)-2-(7-Fluoro-1-oxo-6-(2-((tetrahydro-2H-pyran-4-yl)amino)pyrimidin-4-yl)isoindolin-2-yl)-N—((S)-2-hydroxy-1-(m-tolyl)ethyl)propenamide

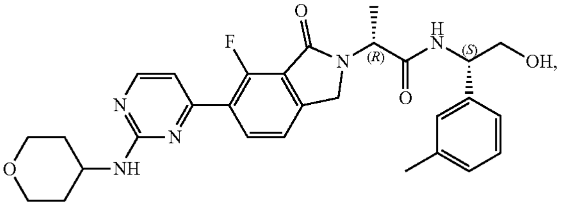

(R)-2-(7-fluoro-1-oxo-6-(2-((tetrahydro-2H-pyran-4-yl) amino)pyrimidin-4-yl)isoindolin-2-yl)-N—((S)-2-hydroxy-1-(m-tolyl)ethyl)propanamide as a yellow solid (3.79 mg) was prepared according to the same method of embodiment 25. LC-MS $[M+H]^+$: m/z 534.3. $^1H$ NMR (400 MHz, $CD_3OD$): δ8.36-8.29 (m, 2H), 7.53 (d, J=8.0 Hz, 1H), 7.35-6.94 (m, 5H), 5.06-5.01 (m, 1H), 4.94-4.91 (m, 1H), 4.83 (d, J=18.4 Hz, 1H), 4.67 (d, J=18.4 Hz, 1H), 4.17-4.07 (m, 1H), 4.01-3.96 (m, 2H), 3.76-3.68 (m, 2H), 3.56 (t, J=11.6 Hz, 2H), 2.34 (s, 3H), 2.02 (d, J=12.9 Hz, 2H), 1.70-1.63 (m, 2H), 1.55 (d, J=7.3 Hz, 3H).

Embodiment 27: (R)-2-(7-Fluoro-6-(2-((1-methyl-1H-pyrazol-5-yl)amino)pyrimidin-4-yl)-1-oxoisoindolin-2-yl)-N—((S)-2-hydroxy-1-(m-tolyl)ethyl) propanamide

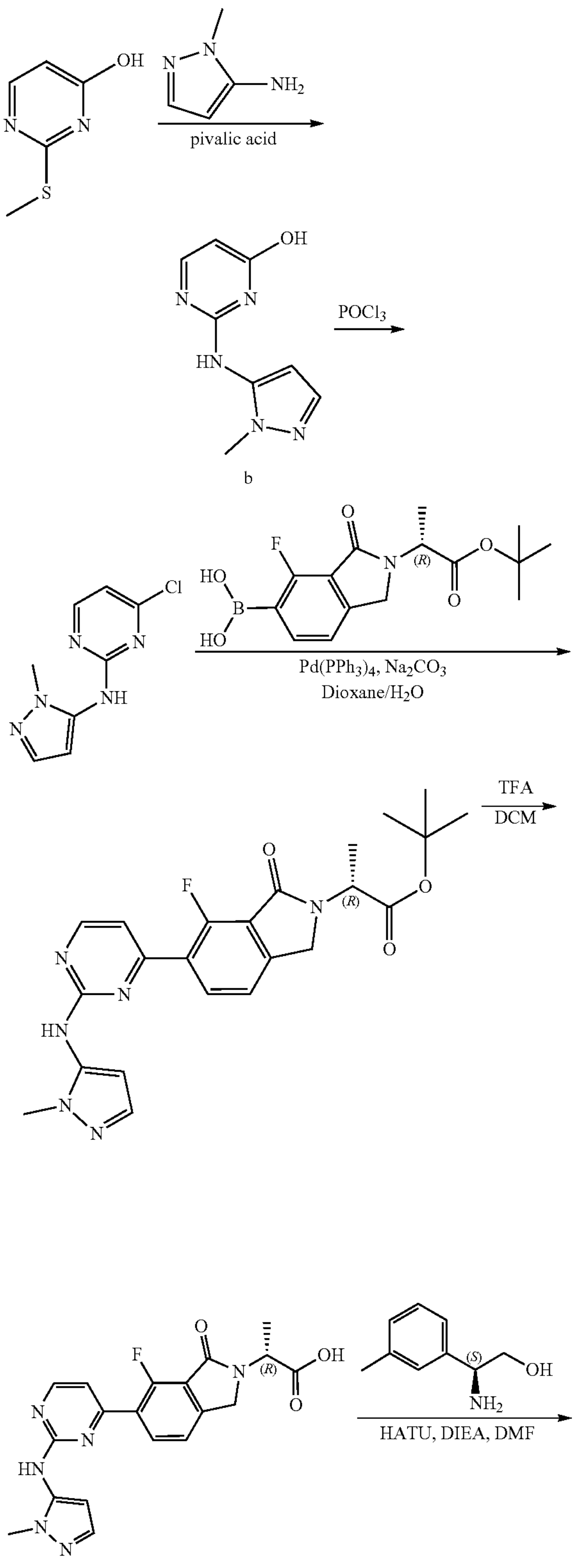

-continued

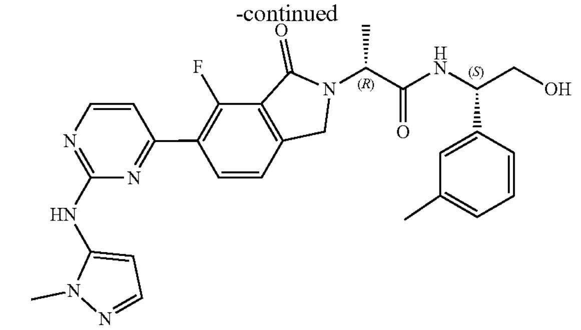

Step 1: Compound 2-(methylthio)pyrimidin-4-ol (1.0 g, 7.03 mmol) and 1-methyl-1H-pyrazol-5-amine (819 mg, 8.44 mmol) were dissolved in isovaleric acid (8 mL), and the reaction solution was reacted at 110° C. for 16 hours, cooled to 70° C., added with petroleum ether (30 mL) and stirred. The mixture was naturally cooled to room temperature, filtered, and the filter cake was washed with petroleum ether to obtain a crude product of 2-((1-methyl-1H-pyrazol-5-yl)amino)pyrimidin-4-ol as a pale yellow solid (1.5 g), which was directly used in the next step.

Step 2: Compound 2-((1-methyl-1H-pyrazol-5-yl)amino)pyrimidin-4-ol (1.5 g) was dissolved in phosphorus oxychloride (12 mL). Under the protection of nitrogen, the reaction solution was reacted at 70° C. for 3 hours, concentrated, and dissolved with dichloromethane. The pH was adjusted to 7 to 8 with saturated sodium bicarbonate, and the mixture was extracted, dried, concentrated and subjected to column chromatography (PE/EA=2:1) to obtain 4-chloro-N-(1-methyl-1H-pyrazol-5-yl)pyrimidin-2-amine as a white solid (590 mg). LC-MS $[M+H]^+$: m/z 210.4.

Step 3: Compound 4-chloro-N-(1-methyl-1H-pyrazol-5-yl)pyrimidin-2-amine (50 mg, 0.155 mmol) and (R)-(2-(1-(tert-butoxy)-1-oxopropan-2-yl)-4-fluoro-3-oxoisoindolin-5-yl)boronic acid (64.7 mg, 0.301 mmol) were dissolved in dioxane/water (3 mL/1 mL). Under the protection of nitrogen, $Pd(PPh_3)_4$(9 mg, 0.0078 mmol) and $K_2CO_3$ (43 mg, 0.31 mmol) were added thereto, and the reaction solution was reacted at 90° C. for 16 hours, concentrated and subjected to column chromatography (PE/EA=0:1) to obtain tert-butyl (R)-2-(7-fluoro-6-(2-((1-methyl-1H-pyrazol-5-yl)amino)pyrimidin-4-yl)-1-oxoisoindolin-2-yl)propanoate as a white solid (80 mg). LC-MS $[M+H]^+$: m/z 453.2.

Step 4: Compound tert-butyl (R)-2-(7-fluoro-6-(2-((1-methyl-1H-pyrazol-5-yl)amino)pyrimidin-4-yl)-1-oxoisoindolin-2-yl)propionate (13 mg) was dissolved in dichloromethane (3 mL), then TFA (1.5 mL) was added thereto, and the reaction solution was stirred for 3 hours, concentrated to remove TFA to obtain (R)-2-(7-fluoro-6-(2-((1-methyl-1H-pyrazol-5-yl)amino)pyrimidin-4-yl)-1-oxoisoindolin-2-yl)propionic acid as a gray-black oil (10 mg), which was directly used in the next step.

Step 5: Compound (R)-2-(7-fluoro-6-(2-((1-methyl-1H-pyrazol-5-yl)amino)pyrimidin-4-yl)-1-oxoisoindolin-2-yl) propionic acid (10 mg, 0.025 mmol) was dissolved in DCM (2 mL), and then 4-chloro-N-(1-methyl-1H-pyrazol-5-yl) pyrimidin-2-amine (4.54 mg, 0.03 mmol), HATU (14 mg, 0.038 mmol), DIEA (13 mg, 0.1 mmol) were added thereto in turn, and the reaction was stirred overnight at room temperature, then poured into saturated aqueous sodium carbonate solution (10 mL), and then extracted with DCM (10 mL*3), dried over $MgSO_4$. The mixture was filtered, and concentrated and subjected to preparative column chromatography (acid method-trifluoroacetic acid) to obtain (R)-2-(7-fluoro-6-(2-((1-methyl-1H-pyrazol-5-yl)amino)-1H-pyrazol-5-yl)amino)pyrimidin-4-yl)-1-oxoisoindolin-2-yl)-N—((S)-2-hydroxy-1-(m-tolyl)ethyl)propanamide as a yellow solid (3.7 mg). LC-MS $[M+H]^+$: m/z 534.3. $^1H$ NMR (400 MHz, MeOD-$d_4$): δ8.36-8.29 (m, 2H), 7.53 (d, J=8.0 Hz, 1H), 7.35-6.94 (m, 5H), 5.06-5.01 (m, 1H), 4.94-4.91 (m, 1H), 4.83 (d, J=18.4 Hz, 1H), 4.67 (d, J=18.4 Hz, 1H), 4.17-4.07 (m, 1H), 4.01-3.96 (m, 2H), 3.76-3.68 (m, 2H), 3.56 (t, J=11.6 Hz, 2H), 2.34 (s, 3H), 2.02 (d, J=12.9 Hz, 2H), 1.70-1.63 (m, 2H), 1.55 (d, J=7.3 Hz, 3H).

Embodiment 28: (R)-2-(2-(5-Fluoro-2-((tetrahydro-2H-pyran-4-yl)amino)pyrimidin-4-yl)-7-oxo-5,7-dihydro-6H-pyrrolo[3,4-b]pyridin-6-yl)-N—((S)-2-hydroxy-1-(m-tolyl)ethyl)propanamide

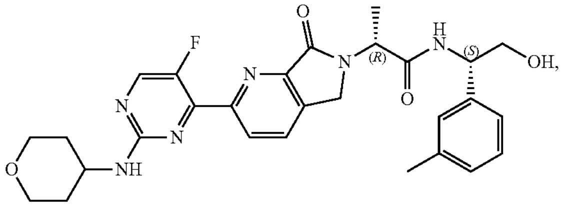

compound (R)-2-(2-(5-fluoro-2-((tetrahydro-2H-pyran-4-yl)amino)pyrimidin-4-yl)-7-oxo-5,7-dihydro-6H-pyrrolo[3,4-b]pyridin-6-yl)-N—((S)-2-hydroxy-1-(m-tolyl)ethyl)propanamide as a white solid (4.6 mg) was prepared according to the same method of embodiment 2. LC-MS $[M+H]^+$: m/z 535.2. $^1H$ NMR (400 MHz, $CDCl_3$): δ8.71 (s, 1H), 8.32 (s, 1H), 7.89 (s, 1H), 7.75 (s, 1H), 7.17-7.26 (m, 3H), 7.06 (d, J=7.2, 1H), 5.27-5.31 (m, 1H), 5.08-5.14 (m, 1H), 5.01 (d, J=18.8 Hz, 1H), 4.51 (d, J=18.4 Hz, 1H), 3.90-4.03 (m, 4H), 3.84-3.88 (m, 1H), 3.71-3.74 (m, 1H), 3.51-3.58 (m, 2H), 2.32 (s, 3H), 1.97-2.08 (m, 2H), 1.57-1.67 (m, 2H), 1.53 (d, J=6.0 Hz, 3H).

Embodiment 29: (R)-2-(7-Fluoro-6-(2-(isopropylamino)pyrimidin-4-yl)-1-oxoisoindolin-2-yl)-N—((S)-2-hydroxy-1-(m-tolyl)ethyl)propanamide

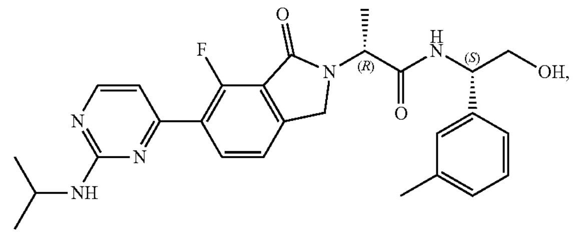

(R)-2-(7-fluoro-6-(2-(isopropylamino)pyrimidin-4-yl)-1-oxoisoindolin-2-yl)-N—((S)-2-hydroxy-1-(m-tolyl)ethyl) propanamide as a white solid (0.9 mg) was prepared by the same method of embodiment 25. LC-MS $[M+H]^+$: m/z 492.2. $^1H$ NMR (400 MHz, MeOD-$d_4$): δ8.33-8.29 (m, 2H), 7.49 (d, J=8.4 Hz, 1H), 7.21 (t, J=7.6 Hz, 1H), 7.16 (s, 1H), 7.12 (d, J=7.6 Hz, 1H), 7.08-7.06 (m, 2H), 5.34 (t, J=4.8 Hz, 1H), 5.06-5.01 (q, 1H),4.83 (d, J=18.4 Hz, 1H), 4.66 (d, J=18.4 Hz, 1H), 4.23-4.15 (m, 1H), 3.72-3.70 (m, 2H), 2.34 (s, 3H), 1.55 (d, J=4.0 Hz, 3H), 1.26-1.25 (d, 6H).

Embodiment 30: (R)—N—((S)-2-Hydroxy-1-(m-tolyl)ethyl)-2-(7-oxo-2-(2-((tetrahydro-2H-pyran-4-yl)amino)pyrimidin-4-yl)-5,7-dihydro-6H-pyrrolo[3,4-b]pyridin-6-yl)propanamide

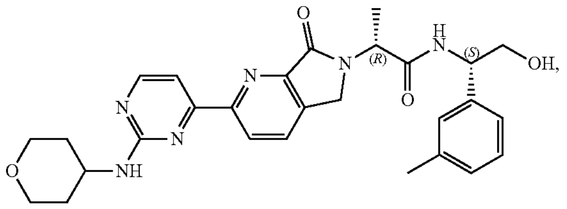

compound (R)—N—((S)-2-hydroxy-1-(m-tolyl)ethyl)-2-(7-oxo-2-(2-((tetrahydro-2H-pyran-4-yl)amino)pyrimidin-4-yl)-5,7-dihydro-6H-pyrrolo[3,4-b]pyridin-6-yl)propanamide as a white solid (7.1 mg) in embodiment 30 was prepared by the same method of embodiment 2. LC-MS $[M+H]^+$: m/z 517.3. $^1H$ NMR (400 MHz, MeOD-$d_4$): δ8.68 (d, J=8.0 Hz, 1H), 8.44 (d, J=6.0 Hz, 1H), 8.23 (d, J=8.0 Hz, 1H), 7.94 (d, J=6.0 Hz, 1H), 7.07-7.24 (m, 4H), 5.14-5.19 (m, 1H), 4.93-4.96 (t, J=7.6 Hz, 1H), 4.89 (d, J=18.0 Hz, 1H), 4.73 (d, J=18.0 Hz, 1H), 4.19-4.25 (m, 1H), 4.02 (m, 2H), 3.68-3.75 (m, 2H), 3.58-3.63 (t, J=21.6 Hz, 2H), 2.34 (s, 3H), 2.03-2.08 (m, 2H), 1.68-1.75 (m, 2H), 1.60 (d, J=7.2 Hz, 3H).

Embodiment 31: (R)-2-(7-Fluoro-6-(5-fluoro-2-((tetrahydro-2H-pyran-4-yl)amino)pyrimidin-4-yl)-1-oxoisoindolin-2-yl)-N—((S)-2-hydroxy-1-(m-tolyl)ethyl)propanamide

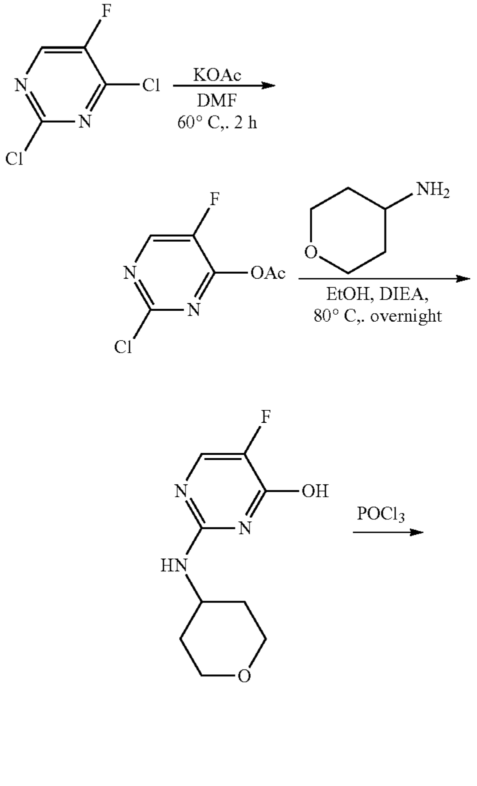

-continued

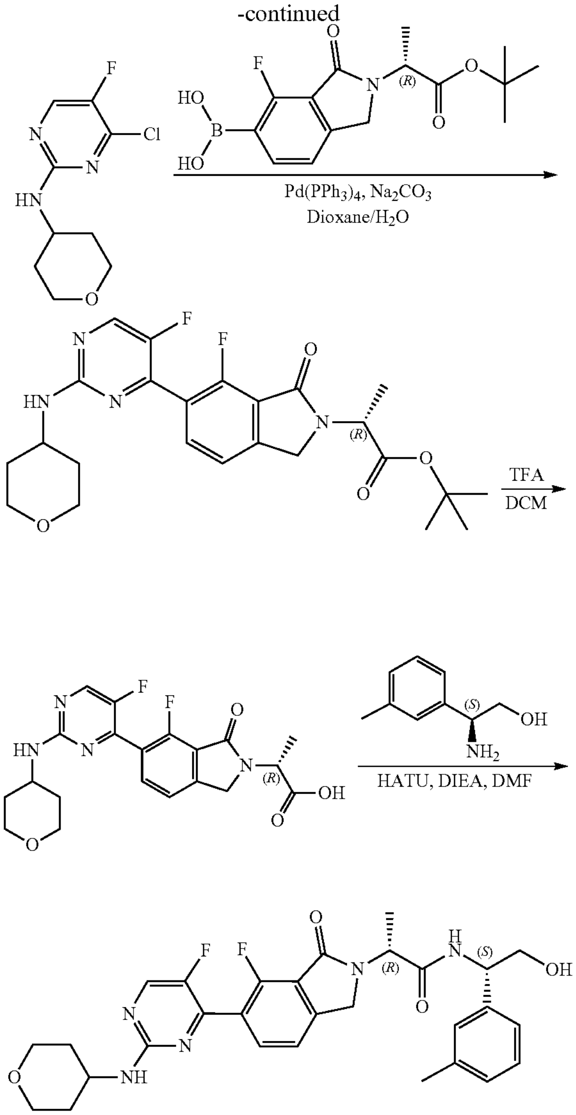

Step 1: Compound 2,4-dichloro-5-fluoropyrimidine (2.0 g, 12 mmol) was dissolved in DMF (20 mL), and potassium acetate (2.3 g, 24 mmol) was added thereto. Under the protection of nitrogen, the reaction solution was reacted at 60° C. for 2 hours. The mixture was added with water, and the pH was adjusted to 4 to 5 with 3N HCl, and the aqueous phase was washed twice with ethyl acetate, dried over anhydrous sodium sulfate and concentrated to obtain compound 2-chloro-5-fluoropyrimidin-4-yl acetate as a yellow solid (800 mg).

Step 2: Compound 2-chloro-5-fluoropyrimidin-4-yl acetate (100 mg, 0.68 mmol) was dissolved in n-butanol (5 mL), then 4-amino-tetrahydropyran (205 mg, 2.0 mmol), p-toluenesulfonic acid monohydrate (259 mg, 3.4 mmol) were added thereto. Under the protection of nitrogen, the reaction solution was reacted at 120° C. overnight. The mixture was concentrated, added with water, and the aqueous phase was extracted for seven times with dichloromethane and isopropanol (3/1), and then dried over anhydrous sodium sulfate and concentrated to obtain compound 5-fluoro-2-((tetrahydro-2H-pyran-4-yl)amino)pyrimidin-4-ol as a white solid (73 mg). LC-MS $[M+H]^+$-: m/z 214.0.

Step 3: Compound 5-fluoro-2-((tetrahydro-2H-pyran-4-yl)amino)pyrimidin-4-ol (73 mg, 0.34 mmol) was dissolved in phosphorus oxychloride ($POCl_3$) (5 mL), and the reaction solution was reacted at 90° C. overnight under the protection of nitrogen. The mixture was concentrated, diluted with dichloromethane, and washed with saturated aqueous sodium bicarbonate solution ($NaHCO_3$), then dried over anhydrous sodium sulfate and subjected to column chromatography (PE/EA=5/1) to obtain compound 4-chloro-5-fluoro-N-(tetrahydro-2H-pyran-4-yl)pyrimidin-2-amine as a white solid (25.9 mg). LC-MS$[M+H]^+$-: m/z 232.4.

Step 4: Compound 4-chloro-5-fluoro-N-(tetrahydro-2H-pyran-4-yl)pyrimidin-2-amine (25.9 mg), (R)-(2-(1-(tert-butoxy)-1-oxopropan-2-yl)-4-fluoro-3-oxoisoindolin-5-yl)boronic acid (34.5 mg, 0.11 mmol) were dissolved in dioxane/$H_2O$ (3 mL/1 mL), and $K_2CO_3$ (29 mg, 0.21 mmol) was added thereto. Under the protection of nitrogen, $Pd(PPh_3)_4$ was added thereto, and the reaction solution was reacted at 90° C. overnight. The mixture was washed with water, extracted with EA, concentrated, and subjected to column chromatography by a wet process to obtain compound tert-butyl (R)-2-(7-fluoro-6-(5-fluoro-2-((tetrahydro-2H-pyran-4-yl)amino)pyrimidin-4-yl)-1-oxoisoindolin-2yl)-propanoate as a yellow solid (36 mg). LC-MS $[M+H]^+$-: m/z 475.3.

Step 5, step 6 were operated with reference to embodiment 25 to obtain compound (R)-2-(7-fluoro-6-(5-fluoro-2-((tetrahydro-2H-pyran-4-yl)amino)pyrimidin-4-yl)-1-oxoisoindolin-2-yl)-N—((S)-2-hydroxy-1-(m-tolyl)ethyl) propanamide as a white solid (16 mg). LC-MS $[M+H]^+$: m/z 552.3. $^1$H NMR (400 MHz, $CD_3OD$): δ8.31 (d, J=2.0 Hz, 1H), 7.84-7.88 (dd, J=6.4, 7.6 Hz, 1H), 7.53 (d, J=7.6 Hz, 1H), 7.07-7.24 (m, 4H), 5.01-5.06 (m, 1H), 4.92-4.95 (m, 1H), 4.81 (d, J=18.4 Hz, 1H), 4.68 (d, J=18.4 Hz, 1H), 3.94-3.99 (m, 3H), 3.71-3.73 (m, 2H), 3.48-3.55 (m, 2H), 2.34 (s, 3H), 1.98-2.01 (m, 2H), 1.54-1.62 (m, 2H), 1.55 (d, J=7.2 Hz, 2H).

Embodiment 32: (R)-2-(6-(5-Chloro-2-((1-methyl-1H-pyrazol-5-yl)amino)pyrimidin-4-yl)-7-fluoro-1-oxoisoindolin-2-yl)-N—((S)-2-hydroxy-1-(m-tolyl) ethyl)propanamide

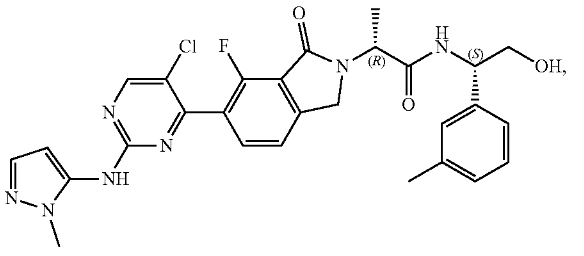

compound (R)-2-(6-(5-chloro-2-((1-methyl-1H-pyrazol-5-yl)amino)pyrimidin-4-yl)-7-fluoro-1-oxoisoindolin-2-yl)-N—((S)-2-hydroxy-1-(m-tolyl)ethyl)propanamide as a white solid (27.6 mg) was obtained according to the operation of embodiment 31. LC-MS $[M+H]^+$: m/z 564.1. $^1$H NMR (400 MHz, $CD_3OD$): δ8.57 (s, 1H), 7.75-7.71 (m, 1H), 7.52 (d, J=7.6 Hz, 1H), 7.48 (s, 1H), 7.22 (t, J=7.6 Hz, 1H), 7.16-7.07 (m, 3H), 6.40 (d, J=2.0 Hz, 1H), 5.05-5.01 (m, 1H), 4.95-4.92 (m, 1H), 4.81 (d, J=18.4 Hz, 1H), 4.68 (d, J=18.4 Hz, 1H), 3.78 (s, 3H), 3.73-3.69 (m, 2H), 2.33 (s, 3H), 1.55 (d, J=7.6 Hz, 3H).

Embodiment 33: (R)-2-(6-(5-Chloro-2-((tetrahydro-2H-pyran-4-yl)amino)pyrimidin-4-yl)-7-fluoro-1-oxoisoindolin-2-yl)-N—((S)-1-(3-fluoro-5-methoxyphenyl)-2-hydroxyethyl)propanamide

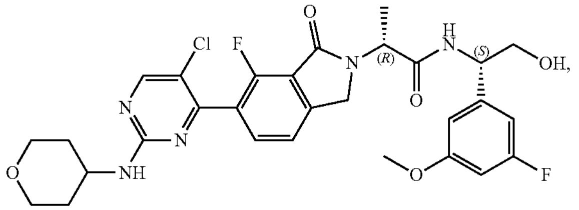

(R)-2-(6-(5-chloro-2-((tetrahydro-2H-pyran-4-yl)amino)pyrimidin-4-yl)-7-fluoro-1-oxoisoindolin-2-yl)-N—((S)-1-(3-fluoro-5-methoxyphenyl)-2-hydroxyethyl)propanamide as a yellow solid (28.2 mg) of embodiment 33 was prepared according to the same method of embodiment 25. LC-MS $[M+H]^+$: m/z 602.2. $^1H$ NMR (400 MHz, $CD_3OD$): δ8.35 (s, 1H), 7.69 (dd, J=7.6, 6.0 Hz, 1H), 7.50 (d, J=8.0 Hz, 1H), 6.74 (s, 1H), 6.68 (d, J=9.2 Hz, 1H), 6.61-6.57 (m, 1H), 5.06-5.01 (m, 1H), 4.95-4.90 (m, 1H), 4.86 (d, J=18.4 Hz, 1H), 4.68 (d, J=18.4 Hz, 1H), 4.02-3.94 (m, 3H), 3.80 (s, 3H), 3.74-3.71 (m, 2H), 3.52-3.47 (m, 2H), 1.99-1.95 (m, 2H), 1.65-1.55 (m, 5H).

Embodiment 34: (R)-2-(6-(5-Chloro-2-((tetrahydro-2H-pyran-4-yl)amino)pyrimidin-4-yl)-7-fluoro-1-oxoisoindolin-2-yl)-N—((S)-1-(3-chlorophenyl)-2-hydroxyethyl)propanamide

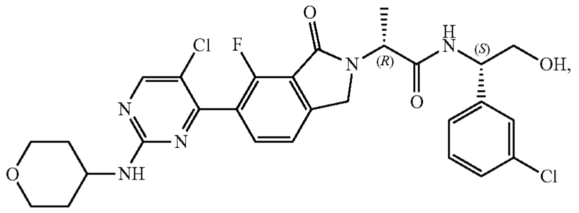

(R)-2-(6-(5-chloro-2-((tetrahydro-2H-pyran-4-yl)amino)pyrimidin-4-yl)-7-fluoro-1-oxoisoindolin-2-yl)-N—((S)-1-(3-chlorophenyl)-2-hydroxyethyl)propanamide as a yellow solid (20.9 mg) of embodiment 34 was prepared according to the same method of embodiment 25. LC-MS $[M+H]^+$: m/z 588.2. $^1H$ NMR (400 MHz, $CD_3OD$): δ8.35 (s, 1H), 7.69 (dd, J=7.6, 6.4 Hz, 1H), 7.50 (d, J=7.6 Hz, 1H), 7.38-7.26 (m, 4H), 5.06-5.01 (m, 1H), 4.97-4.93 (m, 1H), 4.82 (d, J=18.0 Hz, 1H), 4.66 (d, J=18.4 Hz, 1H), 4.02-3.94 (m, 3H), 3.78-3.70 (m, 2H), 3.52-3.47 (m, 2H), 1.98-1.95 (m, 2H), 1.62-1.55 (m, 5H).

Embodiment 35: (R)—N—((S)-2-Hydroxy-1-(m-tolyl)ethyl)-2-(7-oxo-2-(2-((tetrahydro-2H-pyran-4-yl)amino)pyrimidin-4-yl)-5,7-dihydro-6H-pyrrolo[3,4-b]pyridin-6-yl)propanamide

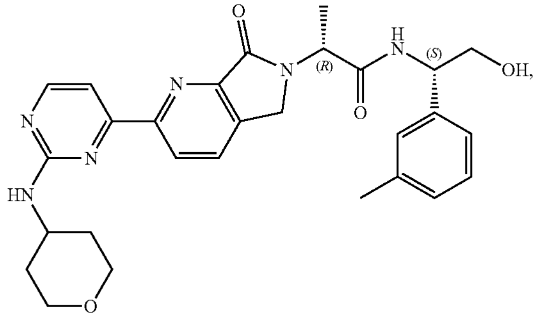

(R)—N—((S)-2-hydroxy-1-(m-tolyl)ethyl)-2-(7-oxo-2-(2-((tetrahydro-2H-pyran-4-yl)amino)pyrimidin-4-yl)-5,7-dihydro-6H-pyrrolo[3,4-b]pyridin-6-yl)propanamide as a white solid (7.1 mg) of embodiment 35 was prepared according to the same method of embodiment 2. LC-MS $[M+H]^+$: m/z 517.3. $^1H$ NMR (400 MHz, $CD_3OD$): δ8.68 (d, J=8.0 Hz, 1H), 8.44 (d, J=6.0 Hz, 1H), 8.23 (d, J=8.0 Hz, 1H), 7.94 (d, J=6.0 Hz, 1H), 7.07-7.24 (m, 4H), 5.14-5.19 (m, 1H), 4.93-4.96 (t, J=7.6 Hz, 1H), 4.89 (d, J=18.0 Hz, 1H), 4.73 (d, J=18.0 Hz, 1H), 4.19-4.25 (m, 1H), 4.02 (m, 2H), 3.68-3.75 (m, 2H), 3.58-3.63 (t, J=21.6 Hz, 2H), 2.34 (s, 3H), 2.03-2.08 (m, 2H), 1.68-1.75 (m, 2H), 1.60 (d, J=7.2 Hz, 3H).

Embodiments 36 to 50 were synthesized according to the method of embodiment 31.

| Embodiment | Structure | Analytical data (LC-MS and $^1H$-NMR) |
|---|---|---|
| 36 | 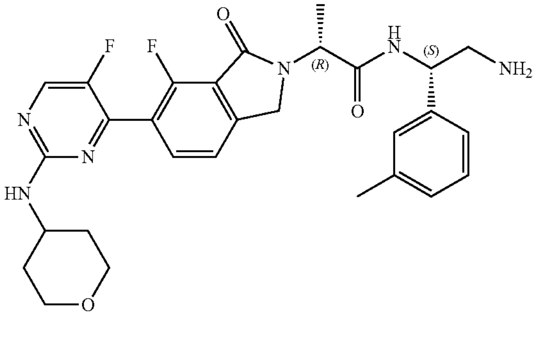 | $[M + H]^+$: m/z 551.1. (400 MHz, $CD_3OD$): δ 8.31 (d, J = 2.0 Hz, 1H), 7.84-7.88 (dd, J = 6.4, 7.6 Hz, 1H), 7.53 (d, J = 7.6 Hz, 1H), 7.07-7.24 (m, 4H), 5.01-5.06 (m, 1H), 4.92-4.95 (m, 1H), 4.81-4.83 (m, 1H), 4.68 (d, J = 18.4 Hz, 1H), 3.94-3.99 (m, 3H), 3.71-3.73 (m, 3H), 3.48-3.55 (m, 2H), 2.34 (s, 3H), 1.98-2.01 (m, 2H), 1.54-1.62 (m, 2H), 1.55 (d, J = 7.2 Hz, 2H). |

-continued
| Embodiment | Structure | Analytical data (LC-MS and $^1$H-NMR) |
|---|---|---|
| 37 | 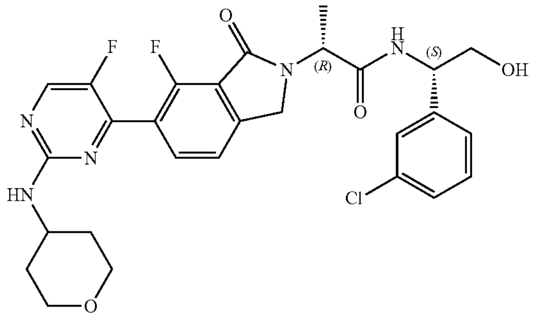 | [M + H]$^+$: m/z 572.2. (400 MHz, $CD_3OD$): δ 8.35 (d, J = 2.0 Hz, 1H), 7.84-7.88 (dd, J = 6.4, 7.6 Hz, 1H), 7.53 (d, J = 7.6 Hz, 1H), 7.07-7.24 (m, 4H), 5.01-5.06 (m, 1H), 4.92-4.95 (m, 1H), 4.81 (d, J = 18.4 Hz, 1H), 4.68 (d, J = 18.4 Hz, 1H), 3.94-3.99 (m, 3H), 3.71-3.73 (m, 2H), 3.48-3.55 (m, 2H), 2.34 (s, 3H), 1.98-2.01 (m, 2H), 1.54-1.62 (m, 2H), 1.55 (d, J = 7.2 Hz, 2H). |
| 38 | 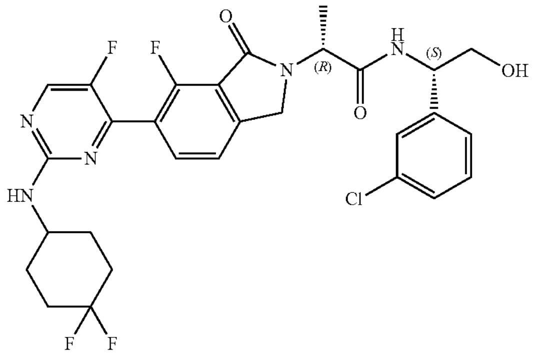 | [M + H]$^+$: m/z 606.1. |
| 39 | 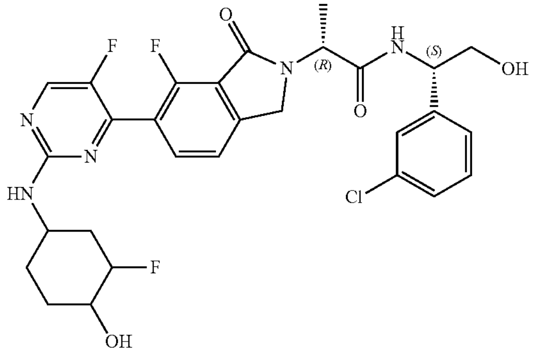 | [M + H]$^+$: m/z 604.0 |
| 40 | 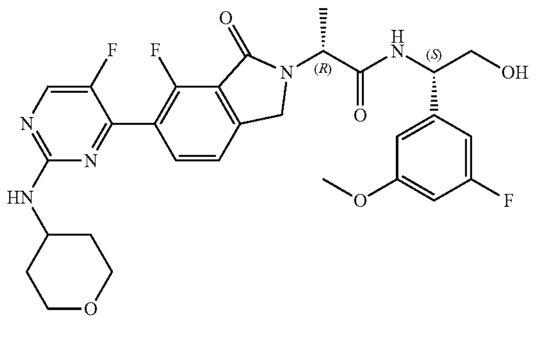 | [M + H]$^+$: m/z 585.8. $^1$H-NMR (40 MHz, $CD_3OD$): δ 8.33 (s, 1H), 7.70 (dd, J = 7.6, 6.0 Hz, 1H), 7.52 (d, J = 8.0 Hz, 1H), 6.74 (s, 1H), 6.68 (d, J = 9.2 Hz, 1H), 6.61-6.57 (m, 1H), 5.06-5.01 (m, 1H), 4.95-4.90 (m, 1H), 4.86 (d, J = 18.4 Hz, 1H), 4.68 (d, J = 18.4 Hz, 1H), 3.80 (s, 3H), 3.74-3.71 (m, 2H), 3.52-3.47 (m, 2H), 1.99-1.95 (m, 2H), 1.65-1.55 (m, 5H). |

-continued
| Embodiment | Structure | Analytical data (LC-MS and $^1$H-NMR) |
|---|---|---|
| 41 | 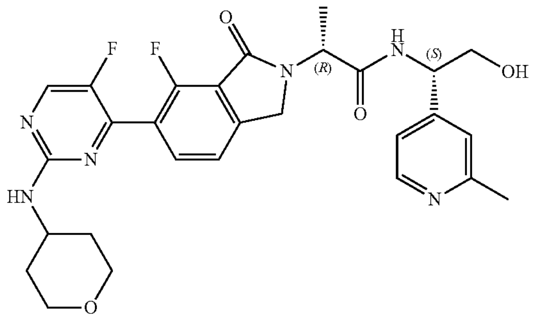 | $[M + H]^+$: m/z 553.1 |
| 42 | 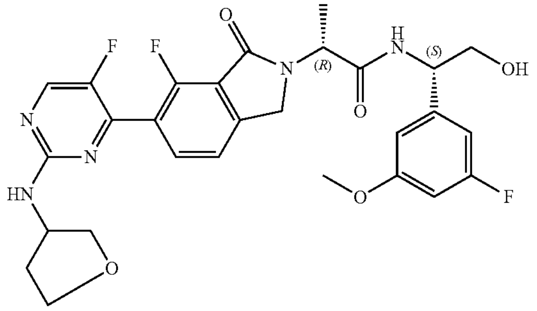 | $[M + H]^+$: m/z 572.2 |
| 43 | 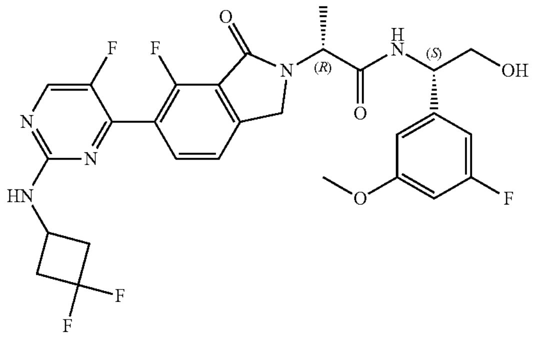 | $[M + H]^+$: m/z 592.4. (400 MHz, $CD_3OD$): δ 8.35 (s, 1H), 7.69 (dd, J = 7.6, 6.0 Hz, 1H), 7.50 (d, J = 8.0 Hz, 1H), 6.74 (s, 1H), 6.68 (d, J = 9.2 Hz, 1H), 6.61-6.57 (m, 1H), 5.06-5.01 (m, 1H), 4.86 (d, J = 18.4 Hz, 1H), 4.68 (d, J = 18.4 Hz, 1H), 4.38-4.42 (m, 1H), 4.02-3.94 (m, 3H), 3.80 (s, 3H), 3.07-3.11 (m, 2H), 2.68-2.75 (m, 2H), 1.65-1.55 (m, 3H). |
| 44 | 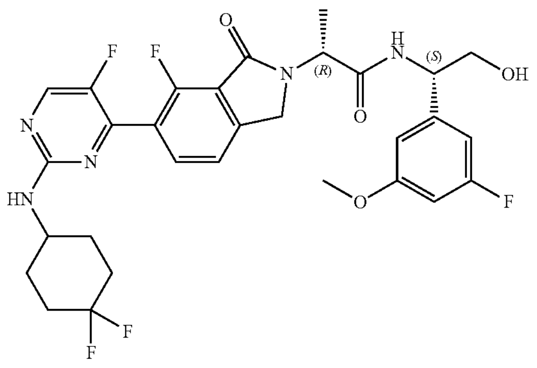 | $[M + H]^+$: m/z 620.2 |

-continued
| Embodiment | Structure | Analytical data (LC-MS and $^1$H-NMR) |
|---|---|---|
| 45 | 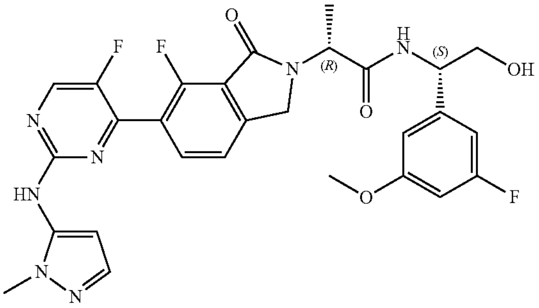 | $[M + H]^+$: m/z 582.1. (400 MHz, $CD_3OD$): δ 8.57 (s, 1H), 7.75-7.71 (m, 1H), 7.52 (d, J = 7.6 Hz, 1H), 7.48(s, 1H), 7.22-7.26 (m, 2H), 7.16-7.07 (m, 3H), 6.68 (d, J = 9.2 Hz, 1H), 6.40 (d, J = 2.0 Hz, 1H), 5.05-5.01 (m, 1H), 4.95-4.92 (m, 1H), 4.81 (d, J = 18.4 Hz, 1H), 4.68 (d, J = 18.4 Hz, 1H), 3.78 (s, 3H), 3.73-3.69 (m, 2H), 2.33 (s, 3H), 1.55 (d, J = 7.6 Hz, 3H). |
| 46 | 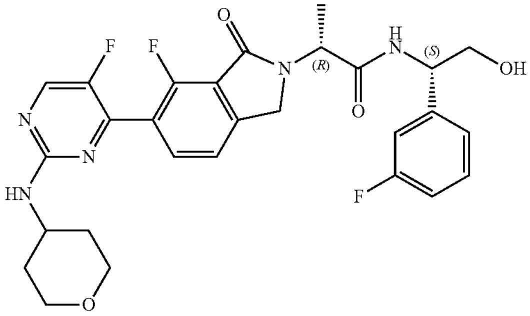 | $[M + H]^+$: m/z 556.2 |
| 47 | 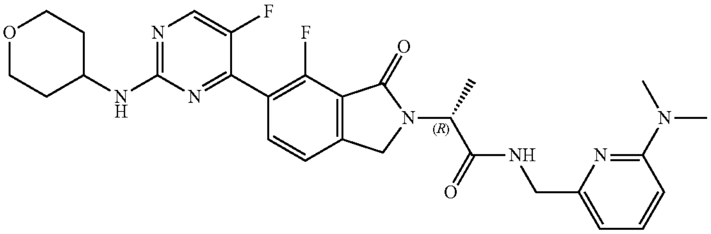 | $[M + H]^+$: m/z 552.1 |
| 48 | 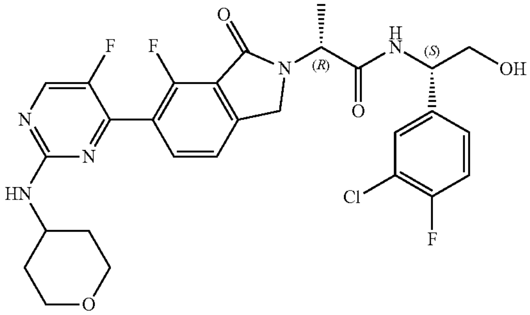 | $[M + H]^+$: m/z 590.2 |
| 49 | 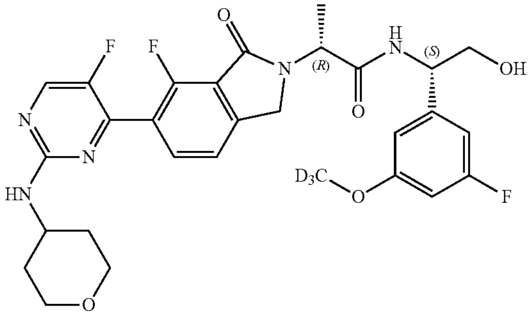 | $[M + H]^+$: m/z 589.2. (400 MHz, $CD_3OD$): δ 8.33 (s, 1H), 7.70 (dd, J = 7.6, 6.0 Hz, 1H), 7.52 (d, J = 8.0 Hz, 1H), 6.74 (s, 1H), 6.68 (d, J = 9.2 Hz, 1H), 6.61-6.57 (m, 1H), 5.06-5.01 (m, 1H), 4.95-4.90 (m, 1H), 4.86 (d, J = 18.4 Hz, 1H), 4.68 (d, J = 18.4 Hz, 1H), 3.74-3.71 (m, 2H), 3.52-3.47 (m, 2H), 1.99-1.95 (m, 2H), 1.65-1.55 (m, 5H). |

-continued

| Embodiment | Structure | Analytical data (LC-MS and $^1$H-NMR) |
|---|---|---|
| 50 | 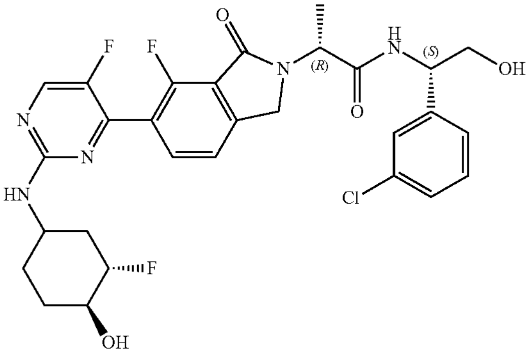 | $[M + H]^+$: m/z 604.1 |

Comparative Compound 1: (R)-2-(6-(5-Chloro-2-((tetrahydro-2H-pyran-4-yl)amino)pyrimidin-4-yl)-1-oxoisoindolin-2-yl)-N—((S')-2-hydroxy-11-(in-tolyl)ethyl)propanamide

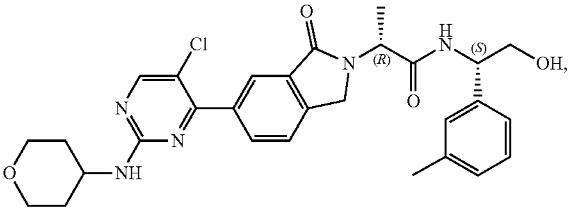

comparative compound 1 was prepared according to the synthetic method of embodiment 683 on page 667 of patent WO2017068412A1. LC-MS $[M+H]^+$: m/z 550.7. $^1$H NMR (400 MHz, DMSO-$d_6$): δ 8.55 (d, J=8.0 Hz, 1H), 8.45 (s, 1H), 8.03 (s, 1H), 7.97 (dd, J=0.8, 8.0 Hz, 1H), 7.74 (d, J=8.0 Hz, 1H), 7.62 (bs, 1H), 7.21 (t, J=7.2 Hz, 1H), 7.04-7.11 (m, 3H), 4.97-5.03 (m, 1H), 4.87 (t, J7.2 Hz, 1H), 4.59-4.82 (m, 3H), 3.85-3.93 (m, 3H), 3.50-3.55 (m, 2H), 3.33-3.40 (m, 2H), 2.29 (s, 3H), 1.82-1.86 (m, 2H), 1.48-1.58 (m, 2H), 1.43 (d, J=7.2 Hz, 3H).

Comparative Compound 2: (R)—N—((S)-1-(3-Chlorophenyl)-2-hydroxyethyl)-2-(6-(2-((1-methyl-1H-pyrazol-5-yl)amino)pyridin-4-yl)-1-oxoisoindolin-2-yl)propanamide

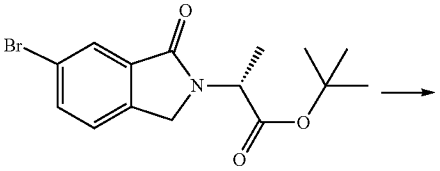

-continued

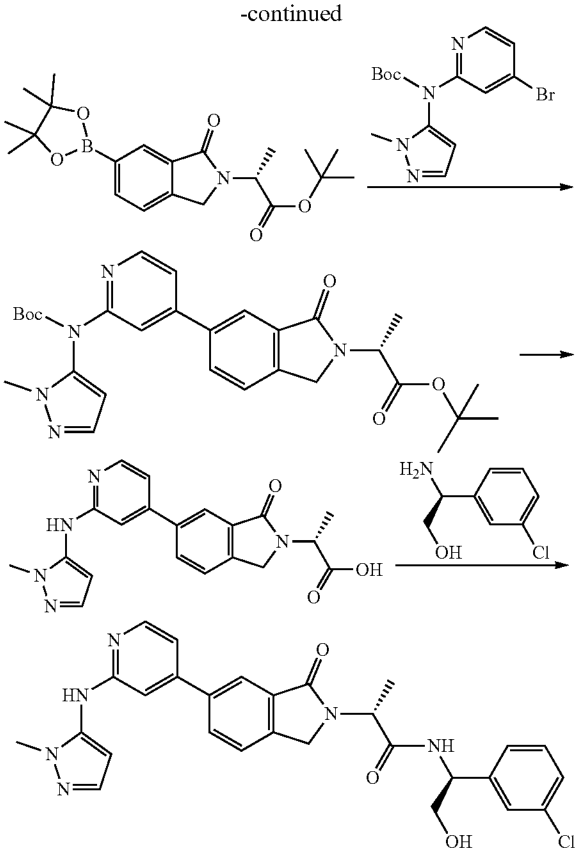

Step 1: tert-Butyl (R)-2-(6-bromo-1-isoindolin-2-yl)propionate (100 mg, 0.29 mmol) and pinacol diborane (150 mg, 0.59 mmol) were dissolved in 1,4-dioxane (3 mL). Under the protection of nitrogen, potassium acetate (KOAc) (87 mg, 0.89 mmol), 1,1'-bis(diphenylphosphino)ferrocene (dppf) (33 mg, 0.06 mmol) and 1,1'-bis(diphenylphosphino)ferrocene-palladium(II)dichloride dichloromethane complex (Pd (dppf)$Cl_2$·$CH_2Cl_2$) (24 mg, 0.03 mmol) were added thereto. The reaction system was replaced with nitrogen for three times, heated to 100° C., and reacted overnight. The mixture was concentrated, and separated by column chromatography to obtain a borate compound (white solid, 83.3 mg). LC-MS $[M+H]^+$: m/z 388.2.

Step 2: The borate compound (83.3 mg, 0.22 mmol) obtained in the previous step and tert-butyl (4-bromopyridin-2-yl)(1-methyl-1H-pyrazol-5-yl)carboxylate (86 mg, 0.22 mmol) were dissolved in 1,4-dioxane/water (6 mL/1 mL). Under the protection of nitrogen, $Na_2CO_3$ (68 mg, 0.65 mmol) and $Pd(PPh_3)_4$(12.4 mg, 0.01 mmol) were added thereto, and the reaction system was replaced with nitrogen for three times, then heated to 80° C., and then reacted overnight. The mixture was concentrated, and separated by column chromatography to obtain tert-butyl (R)-2-(6-(2-((tert-butoxycarbonyl)(1-methyl-1H-pyrazol-5-yl)amino) pyridin-4-yl)-1-isoindolin-2-yl)propionate (white solid, 56.4 mg). LC-MS $[M+H]^+$: m/z 434.2.

Step 3: The compound (56.4 mg, 0.13 mmol) obtained in the previous step was dissolved in anhydrous dichloromethane (1 mL), and TFA (0.5 mL) was added dropwise, and the reaction solution was reacted at room temperature overnight, concentrated at room temperature to obtain a crude product. The crude product was added with DCM and rotary evaporated to dryness, and the process was repeated for three times to obtain (R)-2-(6-(2-((1-methyl-1H-pyrazol-5-yl) amino)pyridin-4-yl)-1-isoindolin-2-yl)propionic acid (white solid, 66.6 mg). LC-MS $[M+H]^+$: m/z 378.2.

Step 4: The compound (66.6 mg, 0.18 mmol) obtained in the previous step was dissolved in DMF (3 mL), then HATU (B4 mg, 0.35 mmol) and DIEA (93 mg, 0.72 mmol) were added thereto, and the reaction solution was stirred for 5 minutes at room temperature, and amino alcohol raw material (30 mg, 0.18 mmol) was added thereto, and the reaction solution was reacted overnight at room temperature. The mixture was diluted with ethyl acetate, washed with saturated ammonium chloride ($NH_4Cl$), dried, concentrated and subjected to column chromatography to obtain comparative compound 2 (white solid product, 26 mg). LC-MS $[M+H]^+$: m/z 531.3. $^1$H NMR (400 MHz, $CD_3OD$): δ8.16 (d, J=8.0 Hz, 1H), 8.06 (s, 1H), 7.93 (dd, J=8.0, 1.6 Hz, 1H), 7.71 (d, J=8.0 Hz, 1H), 7.45 (s, 1H), 7.38 (s, 1H), 7.26-7.35 (m, 3H), 7.13 (dd, J=1.6, 5.6 Hz, 1H), 7.01 (m, 2H), 6.27 (s, 1H), 5.06-5.09 (m, 1H), 4.93-4.96 (m, 1H), 4.64-4.84 (m, 1H), 3.72-3.75 (m, 5H), 1.57 (d, J=7.6 Hz, 3H).

Comparative Compound 3: (R)-2-(3-(5-Chloro-2-((tetrahydro-2H-pyran-4-yl)amino)pyrimidin-4-yl)-5-oxo-5,7-dihydro-6H-pyrrolo[3,4-b]pyridin-6-yl)-N—((S)-2-hydroxy-1-(m-tolyl)ethyl)propanamide

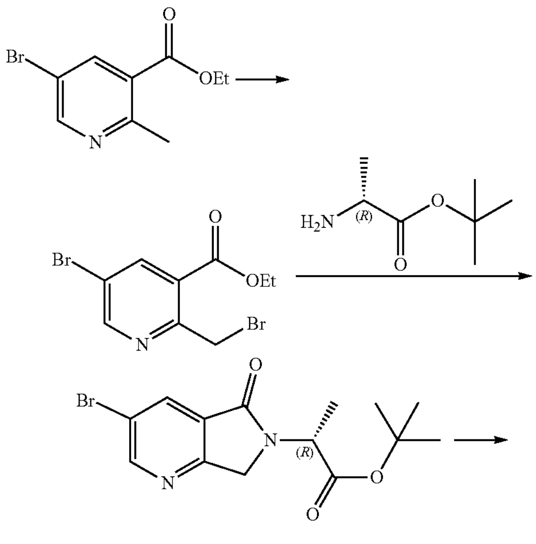

-continued

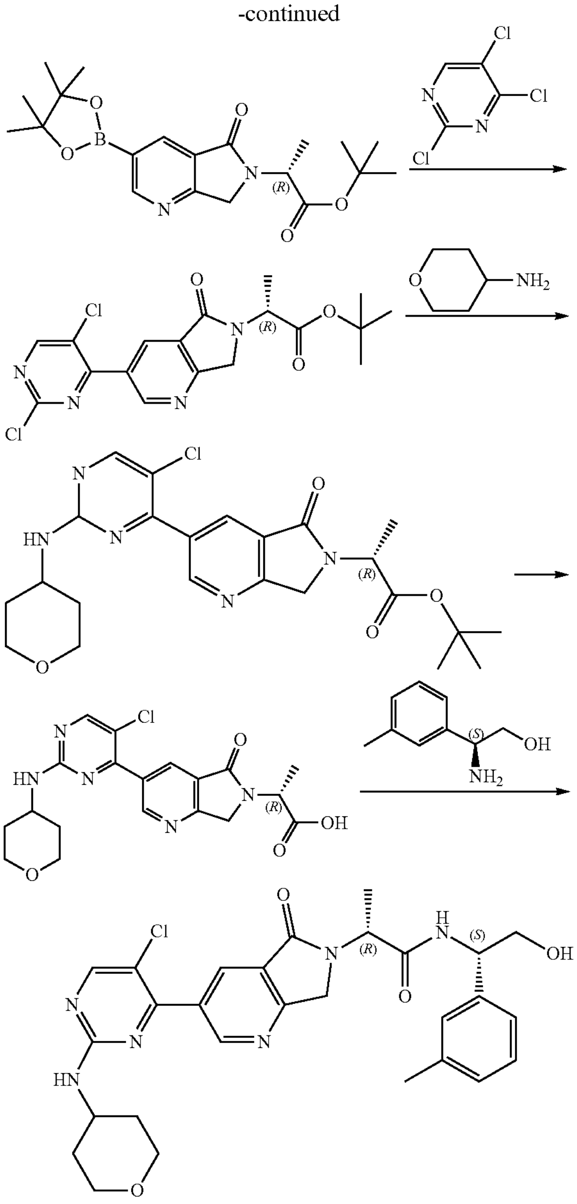

Step 1: Compound ethyl 5-bromo-2-methylnicotinate (5.0 g, 20.6 mmol) was dissolved in carbon tetrachloride ($CCl_4$) (70 mL). Under the protection of nitrogen, NBS (3.7 g, 20.6 mmol), AIBN (338 mg, 0.21 mmol) were added thereto, and the reaction solution was heated to 80° C. and reacted overnight. Then the mixture was cooled down, and subjected to column chromatography (PE/EA=20/1) to obtain ethyl 5-bromo-2-(bromomethyl)nicotinate as a red solid (3.9 g). LC-MS $[M+H]^+$: m/z 323.9.

Step 2: Compound ethyl 5-bromo-2-(bromomethyl)nicotinate (3.9 g, 11.5 mmol) was dissolved in MeOH (60 mL), then tert-butyl D-alaninate (6.3 g, 34.6 mmol), DIEA (11.4 mL, 69 mmol) were added thereto, and the reaction solution was reacted overnight at room temperature under the protection of nitrogen. The mixture was concentrated and subjected to column chromatography (PE/EA=4/1) to obtain compound tert-butyl (R)-2-(3-bromo-5-oxo-5,7-dihydro-6H-pyrrolo[3,4-b]pyridin-6-yl)propionate as a yellow solid (1.9 g). LC-MS $[M+H]^+$: m/z 341.0. $^1$H NMR (400 MHz, DMSO-$d_6$): δ 8.93 (s, 1H), 8.38 (s, 1H), 4.78-4.84 (m, 1H), 4.47-4.63 (m, 2H), 1.51 (d, J=7.2 Hz, 3H), 1.39 (s, 9H).

Step 3: Compound tert-butyl (R)-2-(3-bromo-5-oxo-5,7-dihydro-6H-pyrrolo[3,4-b]pyridin-6-yl)propionate (1.7 g, 5.0 mmol) was dissolved in dioxane (30 mL), then $B_2pin_2$ (1.5 g, 6.0 mmol), KOAc (1.47 g, 15.0 mmol) were added thereto. Under the protection of nitrogen, the third generation palladium catalyst (Pd—X-Phos-G3) (85 mg, 0.1 mmol) was added thereto and the reaction solution was reacted at 90° C. for 3 hours. The mixture was cooled, filtered, and the filter cake was washed with EA, then concentrated, and subjected to reverse-phase preparative separation to obtain compound tert-butyl (R)-2-(5-oxo-3-(4,4,5,5-tetramethyl-1,3,2-dioxaborolan-2-yl)-5,7-dihydro-6H-pyrrolo[3,4-b]pyridin-6-yl)propanoate as a yellow solid (428 mg). LC-MS[M+H]$^+$: m/z 307.4.

Step 4: Compound tert-butyl (R)-2-(5-oxo-3-(4,4,5,5-tetramethyl-1,3,2-dioxaborolan-2-yl)-5,7-dihydro-6H-pyrrolo[3,4-b]pyridin-6-yl)propanoate (428 mg, 1.4 mmol) was dissolved in dioxane/$H_2O$ (12/1.2 mL), then 2,4,5-trichloropyrimidine (770 mg, 4.2 mmol), $K_2CO_3$ (370 mg, 2.8 mmol) were added thereto under the protection of nitrogen, and $Pd(PPh_3)_4$ was added thereto. The reaction solution was reacted at 60° C. overnight, cooled down, diluted with EA, and dried over anhydrous magnesium sulfate. The mixture was filtered, concentrated, and subjected to column chromatography (PE/EA=3/1) to obtain compound tert-butyl (R)-2-(3-(2,5-dichloropyrimidin-4-yl)-5-oxo-5,7-dihydro-6H-pyrrolo[3,4-b]pyridin-6-yl)propionate as a pale yellow oil (196 mg). LC-MS [M+H]$^+$: m/z 353.0. $^1$H NMR (400 MHz, $CD_3OD$): δ9.25 (s, 1H), 8.89 (s, 1H), 8.68 (s, 1H), 4.95-5.01 (m, 1H), 4.74 (s, 2H), 1.63 (d, J=7.6 Hz, 3H), 1.47 (s, 9H).

Step 5: Compound tert-butyl (R)-2-(3-(2,5-dichloropyrimidin-4-yl)-5-oxo-5,7-dihydro-6H-pyrrolo[3,4-b]pyridin-6-yl)propionate (202 mg, 0.5 mmol) was dissolved in ethanol (EtOH) (6 mL), then 4-aminopyran (151 mg, 1.5 mmol), DIEA (258 mg, 2.0 mmol) were added thereto, and the reaction solution was reacted overnight at 90° C. under the protection of nitrogen. The mixture was concentrated, added with water, and the aqueous phase was extracted twice with ethyl acetate, and the organic phase was washed once with saturated sodium chloride solution. The mixture was dried over anhydrous sodium sulfate and concentrated to obtain compound tert-butyl (R)-2-(3-(5-chloro-2-((tetrahydro-2H-pyran-4-yl)amino)pyrimidin-4-yl)-5-oxo-5,7-dihydro-6H-pyrrolo[3,4-b]pyridin-6-yl)propanoate as a yellow solid (230 mg). LC-MS [M+H]$^+$: m/z 474.5

Step 6: Compound tert-butyl (R)-2-(3-(5-chloro-2-((tetrahydro-2H-pyran-4-yl)amino)pyrimidin-4-yl)-5-oxo-5,7-dihydro-6H-pyrrolo[3,4-b]pyridin-6-yl)propanoate (230 mg, 0.49 mmol) was dissolved in DCM (5 mL), and TFA (2 mL) was added thereto. Under the protection of nitrogen, the reaction solution was reacted at room temperature for 3 hours, and concentrated and dried to obtain compound (R)-2-(3-(5-chloro-2-((tetrahydro-2H-pyran-4-yl)amino)pyrimidin-4-yl)-5-oxo-5,7-dihydro-6H-pyrrolo[3,4-b]pyridin-6-yl)propanoic acid as a pale yellow oil (202 mg). LC-MS [M+H]$^+$: m/z 418.4.

Step 7: Compound (R)-2-(3-(5-chloro-2-((tetrahydro-2H-pyran-4-yl)amino)pyrimidin-4-yl)-5-oxo-5,7-dihydro-6H-pyrrolo[3,4-b]pyridin-6-yl)propanoic acid (202 mg of crude product, 0.49 mmol) was dissolved in DMF (5 mL), and tolylamino alcohol (110 mg, 0.73 mmol) was added thereto. Under the protection of nitrogen, HATU (369 mg, 0.97 mmol), DIEA (314 mg, 2.43 mmol) were added thereto. The reaction solution was reacted at room temperature for 1 hour, and prepared to obtain compound (R)-2-(3-(5-chloro-2-((tetrahydro-2H-pyran-4-yl)amino)pyrimidin-4-yl)-5-oxo-5,7-dihydro-6H-pyrrolo[3,4-b]pyridin-6-yl)-N—((S)-2-hydroxy-1-(m-tolyl)ethyl)propanamide as a yellow solid (203 mg). LC-MS [M+H]$^+$: m/z 551.2. $^1$H NMR (400 MHz, $CD_3OD$): δ9.18 (s, 1H), 8.61 (s, 1H), 8.41 (s, 1H), 7.07-7.24 (m, 4H), 5.10-5.15 (m, 1H), 4.91-4.96 (m, 1H), 4.87 (d, J=18.4 Hz, 1H), 4.73 (d, J=18.4 Hz, 1H), 3.96-4.08 (m, 3H), 3.70-3.79 (m, 2H), 3.48-3.55 (m, 2H), 2.34 (s, 3H), 1.97-2.01 (m, 2H), 1.58-1.67 (m, 5H).

Comparative Compound 4: (R)-2-(6-(5-Chloro-2-((tetrahydro-2H-pyran-4-yl)amino)pyrimidin-4-yl)-4-fluoro-1-oxoisoindolin-2-yl)-N—((S)-2-hydroxy-1-(m-tolyl)ethyl)propanamide

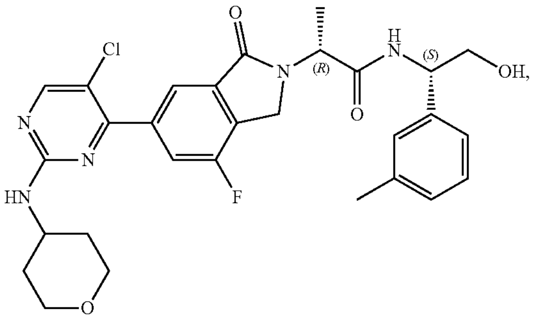

(R)-2-(6-(5-chloro-2-((tetrahydro-2H-pyran-4-yl)amino)pyrimidin-4-yl)-4-fluoro-1-oxoisoindolin-2-yl)-N—((S)-2-hydroxy-1-(m-tolyl)ethyl)propanamide as a yellow solid (161.2 mg) was obtained according to the operation of WO2017068412A1. LC-MS [M+H]$^+$: m/z 568.2. $^1$H NMR (400 MHz, $CD_3OD$): δ8.36 (s, 1H), 8.09 (s, 1H), 7.81 (dd, J=9.6, 1.2 Hz, 1H), 7.22 (t, J=7.6 Hz, 1H), 7.16-7.07 (m, 3H), 5.09-5.05 (m, 1H), 4.96-4.93 (m, 1H), 4.91 (d, J=18.0 Hz, 1H), 4.74 (d, J=18.0 Hz, 1H), 4.05-3.95 (m, 3H), 3.73-3.69 (m, 2H), 3.55-3.49 (m, 2H), 2.33 (s, 3H), 2.00-1.97 (m, 2H), 1.66-1.57 (m, 5H).

Comparative Compound 5: (R)-2-(6-(5-Chloro-2-((tetrahydro-2H-pyran-4-yl)amino)pyrimidin-4-yl)-1-oxoisoindolin-2-yl)-N—((S)-1-(3-fluoro-5-methoxyphenyl)-2-hydroxyethyl)propanamide

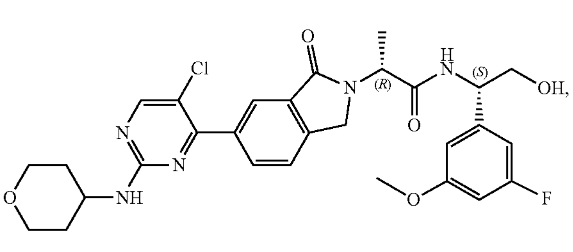

comparative compound 5 (white solid, 35 mg) was prepared according to the synthesis method of comparative compound 1. LC-MS [M+H]$^+$: m/z 584.2. $^1$H NMR (400 MHz, $CD_3OD$): d 8.43 (s, 1H), 8.25 (s, 1H), 8.09 (dd, J=7.6, 1.6 Hz, 1H), 7.74 (d, J=8.0 Hz, 1H), 6.74 (s, 1H), 6.68 (d, J=9.2 Hz, 1H), 6.57-6.61 (m, 1H), 5.06-5.11 (m, 1H), 4.91-4.94 (m, 1H), 4.84 (d, J=18.0 Hz, 1H), 4.70 (d, J=18.0 Hz, 1H), 4.03-4.10 (m, 1H), 3.95-4.00 (m, 2H), 3.80 (s, 3H), 3.70-3.77 (m, 2H), 3.49-3.55 (m, 2H), 1.98-2.01 (m, 2H), 1.58-1.69 (m, 5H).

Test Embodiment 1: Determination of ERK1/2 Kinase (Brand: Carna) Inhibitory Activity of the Compound of the Present Disclosure (1) Preparation of 1×Kinase buffer; (2) preparation of compound concentration gradient: the initial test concentration of the tested compound was 10 μM, which was 3-fold diluted to 10 concentrations, and a duplicate test was conducted, and then the tested compound was diluted in a 96 well plate to a 100-fold final concentration of 10 different concentrations of solution. Then, the compound of each concentration was further diluted into an intermediate dilution solution with a 5-fold final concentration by using 1×Kinase buffer; (3) 5 μL of the prepared compound solution was added to each compound well of a 384-well plate to test each concentration in a single well; 5 μL of 5% DMSO was added to negative and positive control wells, respectively; (4) the kinase solution with a 2.5-fold final concentration was prepared by using 1×Kinase buffer; (5) 10 μL of the kinase solution with the 2.5-fold final concentration was added to the compound and positive control wells, respectively; 10 μL of the 1×Kinase buffer was added to the negative control wells; (6) the plate was centrifuged at 1,000 rpm for 30 seconds, oscillated and mixed well, and incubated at room temperature for 10 minutes; (7) a mixed solution of ATP and Kinase substrate 22 with a 2.5-fold final concentration was prepared by using 1×Kinase buffer; (8) 10 μL of mixed solution of ATP and substrate with the 2.5-fold final concentration was added to start the reaction; (9) the 384-well plate was centrifuged at 1,000 rpm for 30 seconds, oscillated and mixed well, and incubated at 28° C. for the corresponding time; (10) 30 μL of stop detection solution was added to stop the kinase reaction, and the plate was centrifuged at 1,000 rpm for 30 seconds, oscillated and mixed well; (11) Caliper EZ Reader II was adopted for reading the conversion rate, with the log value of the concentration as the X axis and the percent inhibition as the Y axis. Log (inhibitor) vs. response—Variable slope of the analysis software GraphPad Prism 5 was used to fit the dose-effect curve to obtain the $IC_{50}$ value of each compound on the enzyme activity.

2. Results: The $IC_{50}$ values of the inhibitory activity on ERK1/2 in the embodiment compounds 1 to 50 provided by the present disclosure were all less than 500 nMV, and the $IC_{50}$ of the inhibitory activity in most embodiment compounds were less than 10 nM, even less than 2 nM. For example, embodiment compounds 2, 18, 20, 22, 23, 25, 31, 33, 36, 39, 40, 45 and 49 all showed extremely strong enzyme inhibitory activity. Specific activity results of the embodiment compounds are summarized in Table (I) below. (A<10 nM, 10 nM≤B<200 nM, C≥200 nM)

TABLE I

| ERK½ kinase inhibitory activity | | | | | |
|---|---|---|---|---|---|
| Embodiment number | ERK½ $IC_{50}$ (nM) | Embodiment number | ERK½ $IC_{50}$ (nM) | Embodiment number | ERK½ $IC_{50}$ (nM) |
| 1 | 146 | 2 | 2.4 | 3 | 19 |
| 4 | 105 | 5 | A | 6 | A |
| 7 | B | 8 | A | 9 | A |
| 10 | 13 | 11 | 8.3 | 12 | 12 |
| 13 | B | 14 | B | 15 | B |
| 16 | A | 17 | 5.2 | 18 | 0.8 |
| 19 | 4.8 | 20 | 1.8 | 21 | 5.3 |
| 22 | 1.3 | 23 | 1.7 | 24 | A |
| 25 | 0.7 | 26 | 1.5 | 27 | 1.3 |
| 28 | 3.7 | 29 | 3.6 | 30 | 6.9 |
| 31 | 0.9 | 32 | 1.4 | 33 | 0.9 |
| 34 | 0.8 | 35 | 6.9 | 36 | <1 |
| 37 | <1 | 38 | A | 39 | A |
| 40 | <1 | 41 | <1 | 42 | <1 |
| 43 | A | 44 | A | 45 | <1 |
| 46 | <1 | 47 | A | 48 | <1 |
| 49 | <1 | 50 | A | Comparative compound 1 | 0.6 |
| Comparative compound 2 | 6.7 | Comparative compound 3 | 1.1 | Comparative compound 4 | 0.7 |
| BVD523 | A | GDC0994 | A | LY3214996 | A |

Test Embodiment 2: Effect of the Compound of the Present Disclosure on the Proliferation Capability of Tumor Cell Colo-205

1. Test method: Colo-205 cells (ATCC) in logarithmic growth phase were inoculated into a 96-well culture plate at an appropriate density with 90 μL per well. After overnight culture, different concentrations of the compound were added and acted for 72 hours, and a solvent control group (negative control) was set. After the compound was acted on cells for 72 hours, the effect of the compound on cell proliferation was detected by the cell counting kit CCK-8 (Dojindo), and 10 μL of CCK-8 reagent was added to each well. After the plate was placed in a 37° C. incubator for 2 to 4 hours, a full-wavelength microplate reader SpectraMax 190 was adopted for obtaining the readings with a measured wavelength of 450 nm. The tumor cell growth inhibition rate (%) of the compound was calculated by using the following formula: inhibition rate (%)=(OD of negative control well—OD of administration well)/OD of negative control well×100%. The $IC_{50}$ value was obtained by four-parameter regression with the software attached to the microplate reader.

2. Results: The $IC_{50}$ values of the proliferation inhibitory activity on Colo-205 cells in most embodiment compounds 1 to 50 provided by the present disclosure were less than 1000 nM, and the $IC_{50}$ values of some embodiment compounds were even less than 100 nM. For example, embodiment compounds 2, 5, 8, 18, 22, 23, 31, 33, 34, 36, 37, 40, 42, 44, 45, 48, 49 and so on showed strong cell proliferation inhibitory activity. Specific data are shown in Table (II) below. (The $IC_{50}$ values for cell proliferation inhibitory activity range, expressed as A<100 nM, 100 nM≤B<1000 nM, C≥1000 nM).

TABLE II

| Cell proliferation inhibitory activity | | | | | |
|---|---|---|---|---|---|
| Embodiment number | Colo-205 $IC_{50}$ (nM) | Embodiment number | Colo-205 $IC_{50}$ (nM) | Embodiment number | Colo-205 $IC_{50}$ (nM) |
| 1 | C | 2 | 88.6 | 3 | C |
| 4 | C | 5 | A | 6 | A |
| 7 | B | 8 | A | 9 | B |
| 10 | B | 11 | B | 12 | B |
| 13 | B | 14 | B | 15 | B |
| 16 | A | 17 | B | 18 | 33.3 |
| 19 | 201.8 | 20 | 245.7 | 21 | 90.9 |
| 22 | 67.7 | 23 | A | 24 | B |
| 25 | A | 26 | A | 27 | A |
| 28 | B | 29 | B | 30 | B |
| 31 | 17.4 | 32 | 98.6 | 33 | 14.1 |
| 34 | 34.3 | 35 | B | 36 | A |
| 37 | 4.4 | 38 | B | 39 | B |
| 40 | 3.8 | 41 | A | 42 | A |
| 43 | A | 44 | 18.3 | 45 | A |
| 46 | 16.2 | 47 | B | 48 | 19.2 |
| 49 | 17.4 | 50 | A | Comparative compound 1 | 14 |
| Comparative compound 2 | 354 | Comparative compound 3 | 53.1 | Comparative compound 4 | 37.8 |
| BVD523 | 280 | GDC0994 | 165 | LY3214996 | 316 |

Test Embodiment 3: ADME Test of Embodiment Compounds (1) Metabolic stability test: The metabolic stability incubation was performed with a system containing 150 μL of liver microsomes (final concentration of 0.5 mg/mL), and the system contained NADPH (final concentration of 1 mM), 1 μM of the tested compound, and midazolam as a positive control or atenolol as a negative control. The reaction was stopped with tinidazole-containing acetonitrile at 0 min, 5 min, 10 min and 30 min, respectively. After vortexing for 10 min and centrifuging at 15,000 rmp for 10 min, 50 μL of the supernatant was injected into a 96-well plate. The metabolic stability of the compound was calculated by determining the relative reduction of the drug, calculated as half-life $T_1/2$. The half-life data for the embodiment compounds of the present disclosure in different species of microsomes are shown in the table below.

TABLE III

Liver microsomal stability of different species ($T_{1/2}$, min)

| Embodiment number | Rat | Dog | Human |
|---|---|---|---|
| 2 | 18 | 403 | 15 |
| 25 | 10 | 60 | 18 |
| Comparative compound 1 | 4 | 40 | 3 |

Results: Compared with the comparative compound 1, the stability of the embodiment compounds 2 and 25 in rat, dog and human liver microsomes was significantly improved, indicating that replacing the benzo five-membered lactam ring of the comparative compound 1 with a pyrido five-membered lactam ring or fluorine-substituted benzo five-membered lactam ring had an obvious and unexpected microsome metabolic stability advantage.

TABLE IV

Liver microsomal stability of different species ($T_{1/2}$, min)

| Embodiment number | Rat | Dog | Human |
|---|---|---|---|
| 2 | 18 | 403 | 15 |
| Comparative compound 3 | 6 | 201 | 6 |
| Comparative compound 1 | 4 | 40 | 3 |

Results: Compared with the comparative compounds 1 and 3, the stability of embodiment compound 2 was also significantly improved in rat, dog and human liver microsomes, and when the benzo five-membered lactam ring of comparative compound 1 was replaced with a pyrido five-membered lactam ring, the effect of the substitution position of the pyridine nitrogen atom on the stability of liver microsomes was unpredictable, and the stability of liver microsomes of embodiment 2 was obviously superior to that of comparative compounds 1 and 3.

TABLE V

Liver microsomal stability of different species ($T_{1/2}$, min)

| Embodiment number | Rat | Dog | Human |
|---|---|---|---|
| 25 | 15 | 70 | 18 |
| Comparative compound 1 | 4 | 40 | 3 |
| Comparative compound 4 | 3 | 60 | 3 |

Results: Compared with the comparative compounds 1 and 4, the stability of embodiment compound 25 was also significantly improved in rat and human liver microsomes, and when the benzo five-membered lactam ring of comparative compound 1 was replaced with a fluorine-substituted benzo five-membered lactam ring, the effect of the substitution position of the fluorine atom on the stability of liver microsomes was also unpredictable, and the stability of the embodiment 25 in rat and human liver microsomes was obviously superior to that of the comparative compounds 1 and 4.

TABLE VI

Liver microsomal stability of different species ($T_{1/2}$, min)

| Embodiment number | Mouse | Rat | Dog | Human |
|---|---|---|---|---|
| 18 | 32 | 16 | 32 | 12 |
| 33 | 10 | 17 | 51 | 18 |
| Comparative compound 5 | 15 | 3 | 41 | 3 |

Results: Compared with comparative compound 5, the stability of embodiment compounds 18 and 33 in mouse, rat, and human liver microsomes was significantly improved, especially in rat and human liver microsomes, and this effect was unpredictable.

TABLE VII

Liver microsomal stability of some embodiment compounds in different species ($T_{1/2}$, min)

| Embodiment number | Mouse | Rat | Dog | Human |
|---|---|---|---|---|
| 21 | 234 | 13 | 78 | 62 |
| 31 | 17 | 17 | 122 | 13 |
| 34 | 12 | 19 | 75 | 18 |
| 37 | 12 | 14 | 27 | 11 |
| 40 | 13 | 14 | 73 | 14 |

Some embodiment compounds (such as embodiment compounds 21, 31, 34, 37 and 40) of the present disclosure showed significant advantages in the stability of different kinds of liver microsomes than the comparative compounds. The compounds in other embodiments of the present disclosure also had good stability in liver microsomes of different species.

(2) Direct inhibition test (DI test): A system containing 100 μL of human liver microsomes (final concentration of 0.2 mg/mL) was subjected to a direct inhibition incubation, and the system contained NADPH (final concentration of 1 mM), 10 μM compound, positive inhibitor cocktail (10 μM ketoconazole, 10 μM quinidine, 100 μM sulfaphenazole, 10 μM α-naphthoflavone, 1,000 μM tranylcypromine), negative control (BPS of 0.1% DMSO), and mixed probe substrates (10 μM midazolam, 100 μM testosterone, 10 μM dextromethorphan, M diclofenac, 100 μM phenacetin, 100 μM mephenytoin). After 20 minutes of incubation, the reaction was stopped. The relative activity of the enzyme was calculated by measuring the relative production of metabolites.

Results: The inhibition $IC_{50}$ values of some embodiment compounds (such as embodiment compounds 18, 31, 33, 40, 42, 44, 46, 48 and 49) of the present disclosure were all greater than 10 μM on CYP1A2, 2C8, 2C19, 3A4 and 2D6, showing high druggability.

Test Embodiment 4: In-Vivo Pharmacokinetic Parameters Test of the Embodiment Compounds of the Present Disclosure in Rats or Mice Six male SPF grade SD rats or Balb-c mice (Shanghai Sipple-Bikai Laboratory Animal) were divided into two groups, and the tested compounds were prepared into appropriate solutions or suspensions; one group was administered intravenously (with a dose of 1 mg/kg), and the other group was administered orally (with a dose of 5 mg/kg). Blood samples were collected by jugular vein puncture, and each sample was collected with a volume of about 0.2 mL/time point, and heparin sodium was used for anticoagulation. The time points of blood collection were listed below: 5, 15 and 30 min before administration, 1, 2, 4, 6, 8 and 24 h after administration; the collected blood samples were placed on ice and centrifuged to separate plasma (centrifugation conditions: 8,000 rpm, 6 min, 2 to 8° C.), and the collected plasma was stored at −80° C. before analysis. Plasma samples were analyzed by LC-MS/MS.

The pharmacokinetic parameters such as AUC0-t, AUC0-∞, MRT0-∞, Cmax, Tmax, T1/2 and Vd of the tested compounds and their mean values and standard deviations were calculated by the pharmacokinetic calculation software WinNonlin5.2 non-compartmental model according to the plasma concentration data. In addition, the bioavailability (F) was calculated by the following formula.

$$F = \frac{AUC_{(0-t)(PO)} \times \text{Dose}_{IV}}{AUC_{(0-t)(IV)} \times \text{Dose}_{(PO)}} \times 100\%$$

For samples with concentrations below the lower limit of quantitation, while pharmacokinetic parameter calculations were performed, samples sampled before Cmax was reached should be calculated as a zero value and samples sampled after Cmax was reached should be calculated as below limit of quantitation (BLQ). Specific pharmacokinetic parameters of some embodiment compounds of the present disclosure are listed in Table VIII.

TABLE VIII

Pharmacokinetic parameters of the embodiment compounds on mice

| Embodiment 34 | PK Parameters (IV, 1 mg/kg) | | PK Parameters (PO, 5 mg/kg) | |
|---|---|---|---|---|
| | Cl (mL/min/kg) | 34 | $T_{max}$ (hr) | 0.3 |
| | $V_{ss}$ (L/kg) | 0.7 | $C_{max}$ (nM) | 791 |
| | $t_{1/2}$ (hr) | 0.8 | $t_{1/2}$ (hr) | 1.5 |
| | $MRT_{INF}$ (hr) | 0.3 | $AUC_{last}$ (hr*nM) | 797 |
| | $AUC_{last}$ (hr*nM) | 825 | $AUC_{INF}$ (hr*nM) | 806 |
| | $AUC_{INF}$ (hr*nM) | 830 | F (%) | 19 |
| Embodiment 25 | PK Parameters (IV, 1 mg/kg) | | PK Parameters (PO, 5 mg/kg) | |
| | Cl (mL/min/kg) | 80 | $T_{max}$ (hr) | 0.3 |
| | $V_{ss}$ (L/kg) | 1.6 | $C_{max}$ (nM) | 955 |
| | $t_{1/2}$ (hr) | 0.7 | $t_{1/2}$ (hr) | 1.7 |
| | $MRT_{INF}$ (hr) | 0.3 | $AUC_{last}$ (hr*nM) | 776 |
| | $AUC_{last}$ (hr*nM) | 364 | $AUC_{INF}$ (hr*nM) | 796 |
| | $AUC_{INF}$ (hr*nM) | 368 | F (%) | 43 |
| Embodiment 33 | PK Parameters (IV) | | PK Parameters (PO) | |
| | Cl (mL/min/kg) | 102 | $T_{max}$ (hr) | 0.3 |
| | $V_{ss}$ (L/kg) | 1.3 | $C_{max}$ (nM) | 441 |
| | $t_{1/2}$ (hr) | 0.4 | $t_{1/2}$ (hr) | 1.5 |
| | $MRT_{INF}$ (hr) | 0.2 | $AUC_{last}$ (hr*nM) | 322 |
| | $AUC_{last}$ (hr*nM) | 274 | $AUC_{INF}$ (hr*nM) | 338 |
| | $AUC_{INF}$ (hr*nM) | 276 | F (%) | 25 |
| Embodiment 18 | PK Parameters (IV, 1 mg/kg) | | PK Parameters (PO, 5 mg/kg) | |
| | Cl (mL/min/kg) | 144 | $T_{max}$ (hr) | 0.4 |
| | $V_{ss}$ (L/kg) | 3.9 | $C_{max}$ (nM) | 289 |
| | $t_{1/2}$ (hr) | 1.2 | $t_{1/2}$ (hr) | 0.7 |
| | $MRT_{INF}$ (hr) | 0.5 | $AUC_{last}$ (hr*nM) | 253 |
| | $AUC_{last}$ (hr*nM) | 198 | $AUC_{INF}$ (hr*nM) | 257 |
| | $AUC_{INF}$ (hr*nM) | 202 | F (%) | 25 |
| Embodiment 32 | PK Parameters (IV, 1 mg/kg) | | PK Parameters (PO, 5 mg/kg) | |
| | Cl (mL/min/kg) | 110 | $T_{max}$ (hr) | 0.5 |
| | $V_{ss}$ (L/kg) | 2.7 | $C_{max}$ (nM) | 357 |
| | $t_{1/2}$ (hr) | 1.0 | $t_{1/2}$ (hr) | 1.5 |
| | $MRT_{INF}$ (hr) | 0.4 | $AUC_{last}$ (hr*nM) | 338 |
| | $AUC_{last}$ (hr*nM) | 268 | $AUC_{INF}$ (hr*nM) | 347 |
| | $AUC_{INF}$ (hr*nM) | 272 | F (%) | 26 |

TABLE VIII-continued

| Pharmacokinetic parameters of the embodiment compounds on mice | | | | |
|---|---|---|---|---|
| Embodiment 31 | PK Parameters (IV, 1 mg/kg) | | PK Parameters (PO, 5 mg/kg) | |
| | Cl (mL/min/kg) | 75 | $T_{max}$ (hr) | 0.3 |
| | $V_{ss}$ (L/kg) | 2 | $C_{max}$ (nM) | 1170 |
| | $t_{1/2}$ (hr) | 1.4 | $t_{1/2}$ (hr) | 1.5 |
| | $MRT_{INF}$ (hr) | 0.5 | $AUC_{last}$ (hr*nM) | 1047 |
| | $AUC_{last}$ (hr*nM) | 397 | $AUC_{INF}$ (hr*nM) | 1065 |
| | $AUC_{INF}$ (hr*nM) | 407 | F (%) | 52 |
| Embodiment 37 | PK Parameters (IV, 1 mg/kg) | | PK Parameters (PO, 5 mg/kg) | |
| | Cl (mL/min/kg) | 50 | $T_{max}$ (hr) | 0.3 |
| | $V_{ss}$ (L/kg) | 0.9 | $C_{max}$ (nM) | 1684 |
| | $t_{1/2}$ (hr) | 0.8 | $t_{1/2}$ (hr) | 1.1 |
| | $MRT_{INF}$ (hr) | 0.3 | $AUC_{last}$ (hr*nM) | 1569 |
| | $AUC_{last}$ (hr*nM) | 583 | $AUC_{INF}$ (hr*nM) | 1579 |
| | $AUC_{INF}$ (hr*nM) | 586 | F (%) | 54 |
| Embodiment 40 | PK Parameters (IV, 1 mg/kg) | | PK Parameters (PO, 5 mg/kg) | |
| | Cl (mL/min/kg) | 78 | $T_{max}$ (hr) | 0.3 |
| | $V_{ss}$ (L/kg) | 1.0 | $C_{max}$ (nM) | 1195 |
| | $t_{1/2}$ (hr) | 0.6 | $t_{1/2}$ (hr) | 1.1 |
| | $MRT_{INF}$ (hr) | 0.2 | $AUC_{last}$ (hr*nM) | 1082 |
| | $AUC_{last}$ (hr*nM) | 365 | $AUC_{INF}$ (hr*nM) | 1088 |
| | $AUC_{INF}$ (hr*nM) | 368 | F (%) | 59 |

TABLE IX

| Pharmacokinetic parameters of the some embodiment compounds on SD rats | | |
|---|---|---|
| | Embodiment 37 | Embodiment 40 |
| PK Parameters (IV, 1 mpk) | | |
| Cl (mL/min/kg) | 54 | 94 |
| Vss (L/kg) | 0.8 | 0.9 |
| $t_{1/2}$ (hr) | 0.8 | 0.3 |
| MRTINF (hr) | 0.3 | 0.2 |
| AUClast (hr*nM) | 536 | 303 |
| AUCINF (hr*nM) | 538 | 304 |
| PK Parameters (PO, 5 mpk) | | |
| Tmax (hr) | 0.3 | 0.3 |
| Cmax (nM) | 396 | 476 |
| $t_{1/2}$ (hr) | 1.1 | 1.1 |
| AUClast (hr*nM) | 446 | 432 |
| AUCINF (hr*nM) | 452 | 436 |
| F (%) | 17 | 29 |

Test Embodiment 5: Growth Inhibition Test of the Embodiment Compounds on Nude Mice Colo-205 Transplanted Tumor The tumor tissue in the vigorous growth phase was cut into about 1.5 $mm^3$ and inoculated subcutaneously in the right axilla of nude mice under sterile conditions. The diameter of subcutaneous transplanted tumors in nude mice was measured with a vernier caliper, and the mice were randomly divided into groups when the average tumor volume reached about 130 $mm^3$. The embodiment compounds (injection water containing 1% Tween 80 were configured to a desired concentration for later use) were orally administered daily at a given dose for three consecutive weeks, and the solvent control group was administered with the same amount of solvent. During the whole test, the diameter of transplanted tumor was measured twice a week, and the mice were weighed at the same time. The calculation formula of tumor volume (TV) is expressed as $TV=1/2\times a\times b^2$, wherein a and b represent length and width, respectively. The relative tumor volume (RTV) was calculated according to the measurement results, and the calculation formula is RTV=Vt/V0, wherein V0 is the tumor volume measured when administered in separate cages (i.e., d0), and Vt is the tumor volume at the time of each measurement. The evaluation indicators of anti-tumor activity are: 1) relative tumor proliferation rate T/C (%), the calculation formula is as follows: T/C (%)=(TRTV/CRTV)×100%, wherein TRTV: RTV of the treatment group; CRTV: RTV of the negative control group; 2) tumor volume increase inhibition rate GI %, the calculation formula is as follows: GI %=[1−(TVt−TV0)/(CVt−CT0)]×100%, wherein TVt refers to the tumor volume of the treatment group measured each time; TV0 refers to the tumor volume of the treatment group obtained when being administered in separate cages; CVt refers to the tumor volume of the control group measured each time; CVO refers to the tumor volume of the control group obtained when being administered in separate cages; 3) tumor weight inhibition rate, the calculation formula is as follows: tumor weight inhibition rate (%)=(Wc−WT)/Wc×100%, wherein Wc: tumor weight of the control group, WT: tumor weight of the treatment group.

Some embodiment compounds of the present disclosure (such as embodiment compounds 31, 37 and 40) significantly inhibited the tumor growth of Colo-205 transplanted tumor nude mice at a dose of 50 mg/kg or 25 mg/kg, and had no significant effect on the tumor weight, and had much better tumor inhibition effect than BVD523. Specific data are shown in Table X.

TABLE X

Inhibition of some embodiment compounds on Colo-205 transplanted tumor nude mice

| Number | Mode of administration | Initial weight ($D_0$, g) | Terminal weight ($D_{21}$, g) | Initial tumor volume ($mm^3$ ± SD) | Terminal tumor volume ($mm^3$ ± SD) | T/C |
|---|---|---|---|---|---|---|
| Blank control group | 0.2 mL/20 g, qdx21, po | 19.8 | 19.5 | 97 ± 17 | 971 ± 325 | / |
| BVD523 | 50 mg/kg, qdx21, po | 19.8 | 19.0 | 97 ± 14 | 471 ± 198 | 48.5% |
| Embodiment 31 | 50 mg/kg, qdx21, po | 20.1 | 21.7 | 96 ± 21 | 271 ± 128 | 27.9% |
| Embodiment 37 | 50 mg/kg, qdx21, po | 23.3 | 24.5 | 95 ± 19 | 285 ± 137 | 28.3% |
| Embodiment 40 | 50 mg/kg, qdx21, po | 21.4 | 23.2 | 98 ± 22 | 238 ± 130 | 23.2% |
| Embodiment 40 | 25 mg/kg, bidx21, po | 19.5 | 21.0 | 97 ± 26 | 67 ± 14 | 7.2% |

All documents mentioned in the present disclosure are incorporated herein by reference as if each document is individually incorporated by reference. Moreover, it should be understood that those skilled in the art, upon reading the above contents of the present disclosure, can make various changes or modifications to the present disclosure, and that such equivalents are equally within the scope of the appended claims.

Although specific embodiments of the present disclosure have been described above, those skilled in the art shall understand that these embodiments are for illustration only and that various changes or modifications may be made thereto without departing from the principles and spirit of the present disclosure. The scope of the present disclosure is, therefore, defined by the appended claims.

The invention claimed is:

1. A compound represented by formula (I) or a pharmaceutically acceptable salt thereof, (I)

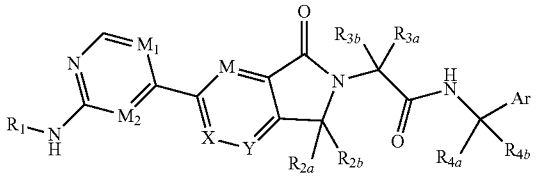

in the formula, $R_1$ is independently selected from substituted 3 to 8 membered cycloalkyl, unsubstituted 3- to 8-membered heterocycloalkyl and substituted 5-to 10-membered heteroaryl; the substituent is independently selected from halogen, hydroxyl or $C_1$-$C_8$ alkyl;

$R_{2a}$ and $R_{2b}$ are independently hydrogen;

$R_{3a}$ and $R_{3b}$ are independently selected from hydrogen and unsubstituted $C_1$-$C_6$ alkyl;

$R_{4a}$ and $R_{4b}$ are independently selected from hydrogen and substituted or unsubstituted $C_1$-$C_6$ alkyl; the substituent is independently selected from hydroxyl and amino;

Ar is selected from any one of the following substituted or unsubstituted groups: 5-to 10- membered aryl or 5-to 10-membered heteroaryl; the substituent is independently selected from one or more than one halogen, $C_1$-$C_6$ alkyl, deuterated $C_1$-$C_6$ alkoxy, $C_1$-$C_6$ alkoxy, $C_1$-$C_6$ alkylamino;

M is selected from N or $CR_5$; $R_5$ is halogen;

$M_1$ and $M_2$ are each independently selected from N and $CR_6$; $R_6$ is independently selected from hydrogen, halogen and $C_1$-$C_6$ alkyl;

X and Y are each CH;

wherein, the heteroaryl contains 1 to 3 heteroatoms selected from the following group: N and O, and the heterocycloalkyl contains 1 to 3 heteroatoms selected from following group: N and O, each ring system is independently saturated or unsaturated monocyclic ring.

2. The compound represented by formula (I) or a pharmaceutically acceptable salt thereof according to claim 1, wherein, the compound satisfies one or more of the following conditions:

(1) $R_{3a}$ is hydrogen; $R_{3b}$ is $C_1$-$C_6$ alkyl;

(2) $R_{4a}$ is hydrogen; $R_{4b}$ is hydrogen or substituted $C_1$-$C_6$ alkyl; the substituent is hydroxyl or amino.

3. The compound represented by formula (I) or a pharmaceutically acceptable salt thereof according to claim 1, wherein, the compound satisfies one or more of the following conditions:

(1) $R_1$ is 3-to 8-membered heterocycloalkyl;

(2) $R_{4a}$ is hydrogen; $R_{4b}$ is substituted $C_1$-$C_6$ alkyl; the substituent is hydroxyl;

(3) Ar is substituted 5-to 10-membered aryl; the substituent is halogen, $C_1$-$C_6$ alkyl, $C_1$-$C_6$ alkoxy, $C_1$-$C_6$ alkylamino or deuterated $C_1$-$C_6$ alkoxy;

(4) $M_1$ is $CR_6$, $R_6$ is halogen; $M_2$ is N.

4. The compound represented by formula (I) or a pharmaceutically acceptable salt thereof according to claim 1, wherein, the compound is any one of the following schemes:

scheme 1:

$R_1$ is 3-to 8-membered heterocycloalkyl, substituted 3 to 8 membered cycloalkyl or substituted 5-to 10-membered heteroaryl; the substituent is hydrogen, hydroxyl or $C_1$-$C_8$ alkyl;

$R_{2a}$ and $R_{2b}$ are hydrogen;

$R_{3a}$ is hydrogen; $R_{3b}$ is $C_1$-$C_6$ alkyl;

$R_{4a}$ is hydrogen; $R_{4b}$ is hydrogen or substituted $C_1$-$C_6$ alkyl; the substituent is hydroxyl or amino;

Ar is 5-to 10-membered aryl, 5-to 10-membered heteroaryl, substituted 5-to 10-membered aryl or substituted 5-to 10-membered heteroaryl; the substituent is halogen, $C_1$-$C_6$ alkyl, $C_1$-$C_6$ alkoxy, $C_1$-$C_6$ alkylamino or deuterated $C_1$-$C_6$ alkoxy;

M is selected from N or $CR_5$; $R_5$ is halogen;

$M_1$ and $M_2$ are independently N or $CR_6$; $R_6$ is independently selected from hydrogen, halogen or $C_1$-$C_6$ alkyl;

X and Y are each CH:

scheme 2:

$R_1$ is 3-to 8-membered heterocycloalkyl;

$R_{2a}$ and $R_{2b}$ are hydrogen;

$R_{3a}$ is hydrogen; $R_{3b}$ is $C_1$-$C_6$ alkyl;

$R_{4a}$ is hydrogen; $R_{4b}$ is substituted $C_1$-$C_6$ alkyl; the substituent is hydroxyl;

Ar is substituted 5-to 10-membered aryl; the substituent is halogen, $C_1$-$C_6$ alkyl, $C_1$-$C_6$ alkoxy, $C_1$-$C_6$ alkylamino or deuterated $C_1$-$C_6$ alkoxy;

M is selected from N or $CR_5$; $R_5$ is halogen;

$M_1$ is $CR_6$, $R_6$ is halogen; $M_2$ is N;

X and Y are each CH.

5. The compound represented by formula (I) or a pharmaceutically acceptable salt thereof according to claim 1, wherein, the compound satisfies one or more of the following conditions:

(1) the compound represented by formula (I) is a compound represented by formula 1

1

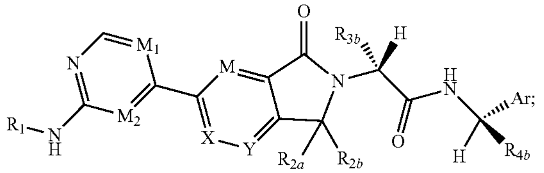

(2) in $R_1$, when the substituent is halogen, the halogen is fluorine, chlorine, bromine or iodine;

(3) in $R_1$, when the substituent is $C_1$-$C_8$ alkyl, the $C_1$-$C_8$ alkyl is methyl, ethyl, n-propyl, isopropyl, n-butyl, isobutyl, sec-butyl or tert-butyl;

(4) in $R_1$, the 3-to 8-membered heterocycloalkyl is 5-to 6-membered heterocycloalkyl;

(5) in $R_1$, the heteroatom of the 3-to 8-membered heterocycloalkyl is 1 to 2 of O atoms;

(6) in $R_6$, the $C_1$-$C_6$ alkyl is methyl, ethyl, n-propyl, isopropyl, n-butyl, isobutyl, sec-butyl or tert-butyl;

(7) in $R_1$, the 3-to 8-membered cycloalkyl is 4-to 6-membered cycloalkyl;

(8) in $R_1$, in the 3-to 8-membered cycloalkyl, each ring system is a saturated monocyclic ring;

(9) in $R_1$, in the 3-to 8-membered cycloalkyl, the 3-to 8-membered cycloalkyl is not oxidized;

(10) in $R_1$, the 5-to 10-membered heteroaryl is 5-to 6-membered heteroaryl;

(11) in $R_1$, the heteroatom of the 5-to 10-membered heteroaryl is 1 to 2 of N atoms;

(12) in $R_1$, in the 5-to 10-membered heteroaryl, each ring system is a monocyclic ring;

(13) in $R_1$, in the 5-to 10-membered heteroaryl, the nitrogen atom in the 5-to 10-membered heteroaryl is not oxidized;

(14) in $R_1$, in the 5-to 10-membered heteroaryl, the nitrogen atom in the 5-to 10-membered heteroaryl is not quaternized;

(15) in $R_{3b}$, the $C_1$-$C_6$ alkyl is methyl, ethyl, n-propyl, isopropyl, n-butyl, isobutyl, sec-butyl or tert-butyl;

(16) in $R_{4b}$, in the substituted $C_1$-$C_6$ alkyl, the $C_1$-$C_6$ alkyl is methyl, ethyl, n-propyl, isopropyl, n-butyl, isobutyl, sec-butyl or tert-butyl;

(17) in Ar, when the substituent is halogen, the halogen is fluorine, chlorine, bromine or iodine;

(18) in Ar, when the substituent is $C_1$-$C_6$ alkyl, the $C_1$-$C_6$ alkyl is methyl, ethyl, n-propyl, isopropyl, n-butyl, isobutyl, sec-butyl or tert-butyl;

(19) in Ar, when the substituent is $C_1$-$C_6$ alkoxy, the $C_1$-$C_6$ alkoxy is methoxy, ethoxy, n-propoxy, isopropoxy, n-butoxy, isobutoxy, sec-butoxy or tert-butoxy;

(20) in Ar, when the substituent is $C_1$-$C_6$ alkylamino, the $C_1$-$C_6$ alkylamino is dimethylamino;

(21) in Ar, the deuterated $C_1$-$C_6$ alkoxy is trideuterated methoxy;

(22) in Ar, in the 5-to 10-membered aryl, the 5-to 10-membered aryl is 6-to 10-membered aryl;

(23) in Ar, the 5-to 10-membered heteroaryl is 5-to 6-membered heteroaryl;

(24) in Ar, the heteroatom of the 5-to 10-membered heteroaryl is 1 to 2 of N atoms;

(25) in Ar, in the 5-to 10-membered heteroaryl, each ring system is a monocyclic ring;

(26) in Ar, in the 5-to 10-membered heteroaryl, the nitrogen atom in the 5-to 10-membered heteroaryl is not oxidized;

(27) in Ar, in the 5-to 10-membered heteroaryl, the nitrogen atom in the 5-to 10-membered heteroaryl is not quaternized;

(28) in $R_5$, the halogen is fluorine, chlorine, bromine or iodine;

(29) in $R_6$, the halogen is fluorine, chlorine, bromine or iodine.

6. The compound represented by formula (I) or a pharmaceutically acceptable salt thereof according to claim 5, wherein, the compound satisfies one or more of the following conditions:

(1) in $R_1$, the 3-to 8-membered heterocycloalkyl is

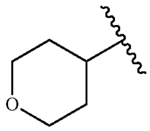 , 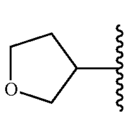 or 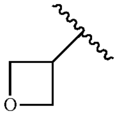 ;

(2) in $R_1$, the substituted 3-to 8-membered cycloalkyl is

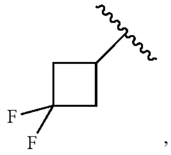 , 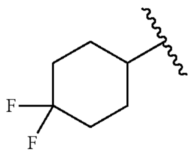 or

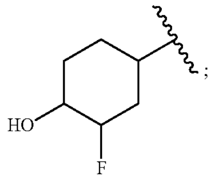 ;

(3) in $R_1$, the substituted 5-to 10-membered heteroaryl is

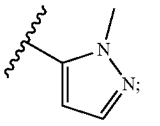 [SMILES: *c1ccnn1C]

(4) in Ar, the substituted 5-to 10-membered aryl is

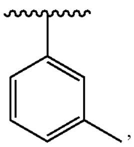,
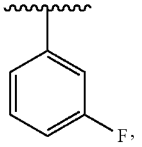,
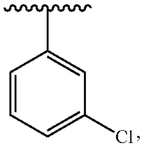,
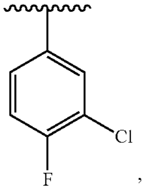,
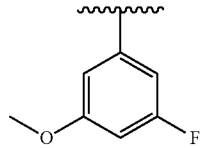 or
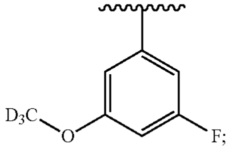

(5) in Ar, the substituted 5-to 10-membered heteroaryl is

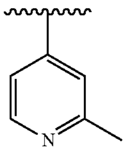 or 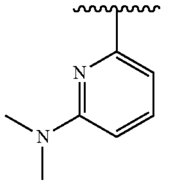;

(6) in R4b, the substituted $C_1$-$C_6$ alkyl is hydroxymethyl or aminomethyl.

7. The compound represented by formula (I) or a pharmaceutically acceptable salt thereof according to claim 1, wherein:

when $M_1$ is $CR_6$, $M_2$ is N;

or, when $M_1$ is N, $M_2$ is CH;

or, when $M_1$ is $CR_6$, $M_2$ is CH.

8. The compound represented by formula (I) or a pharmaceutically acceptable salt thereof according to claim 1, wherein:

when M is $CR_5$, $R_5$ is F.

9. The compound represented by formula (I) or a pharmaceutically acceptable salt thereof according to claim 1, wherein:

$R_1$ is substituted 3 to 8 membered cycloalkyl, unsubstituted 3-to 8-membered heterocycloalkyl or substituted 5-to 10-membered heteroaryl; the substituent is independently selected from halogen, hydroxyl, $C_1$-$C_8$ alkyl;

$R_{2a}$ or $R_{2b}$ is respectively hydrogen;

$R_{3a}$ or $R_{3b}$ is respectively hydrogen or methyl;

$R_{4a}$ is hydrogen or methyl;

$R_{4b}$ is hydrogen, methyl, hydroxymethylene or aminomethylene;

Ar is any one of the following substituted or unsubstituted groups: 5-to 6-membered aryl or 5-to 6-membered heteroaryl; the substituent is independently selected from one or more than one halogen, $C_1$-$C_6$ alkyl, $C_1$-$C_6$ alkoxy, $C_1$-$C_6$ monoalkylamino, $C_1$-$C_6$ dialkylamino.

10. The compound represented by formula (I) or a pharmaceutically acceptable salt thereof according to claim 1, wherein:

the compound represented by formula (I) is selected from the following general formula ((I) A):

((I)A)

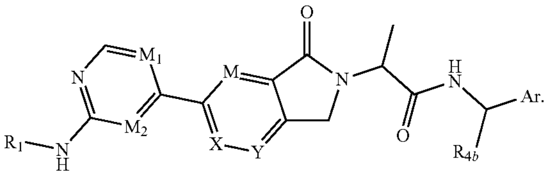

11. The compound represented by formula (I) or a pharmaceutically acceptable salt thereof according to claim 10, wherein:

the compound represented by formula (I) is selected from the following general formulas ((I) B), ((I) C):

((I)B)

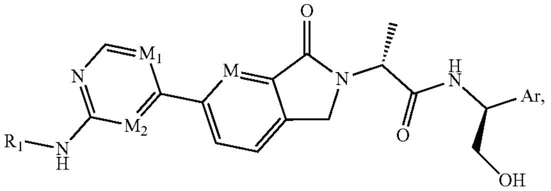

((I)C)

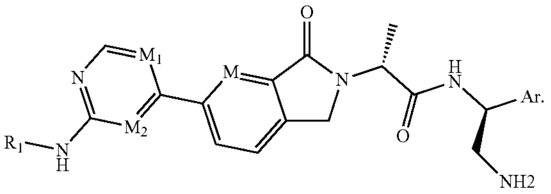

12. The compound represented by formula (I) or a pharmaceutically acceptable salt thereof according to claim 1, wherein, the compound represented by formula (I) is any one of the following compounds:

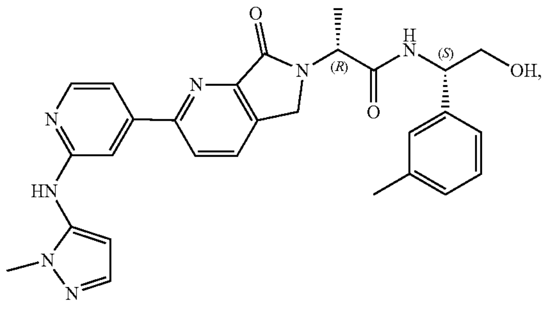

-continued
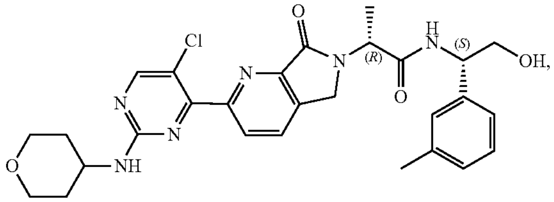
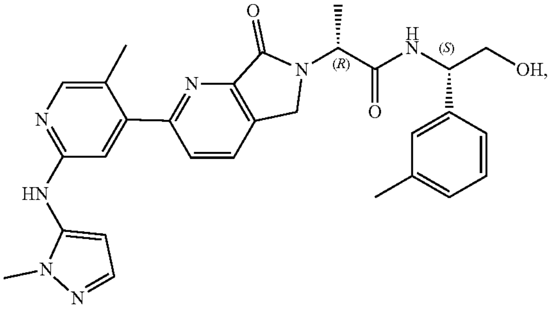
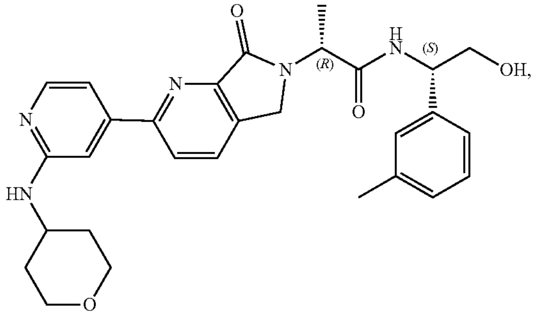
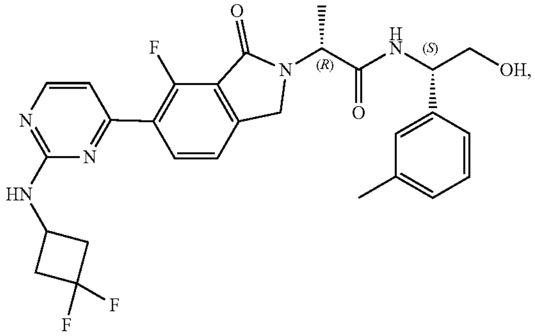
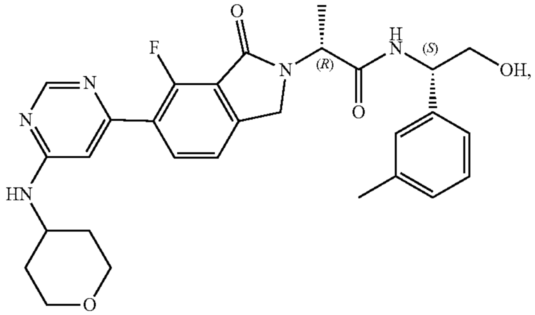
-continued
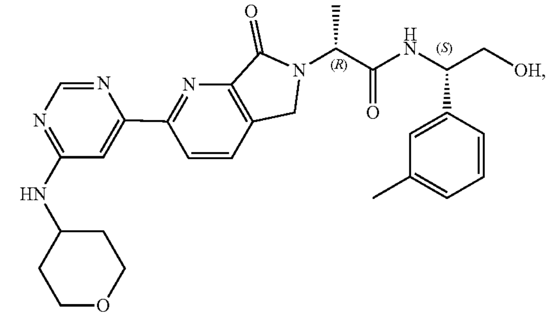
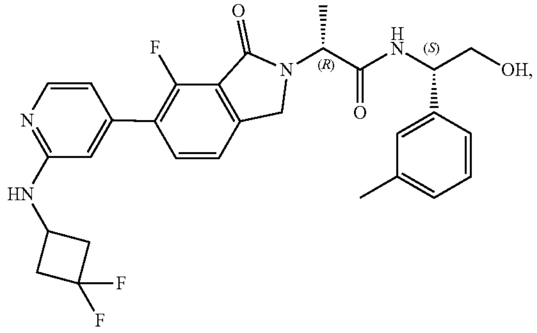
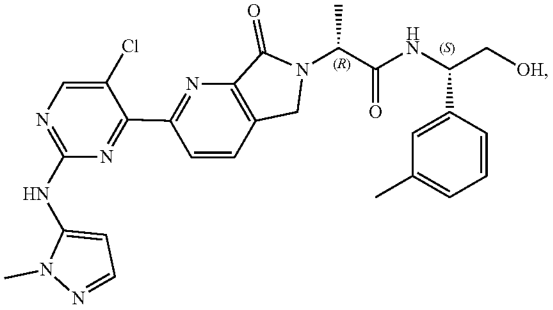
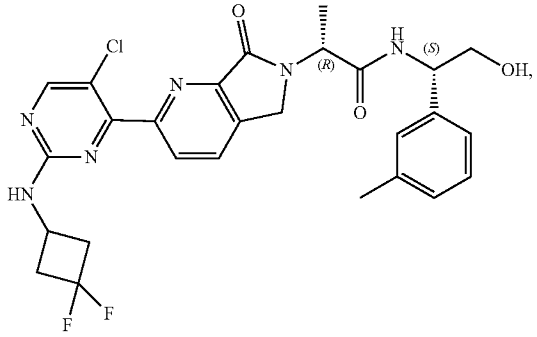
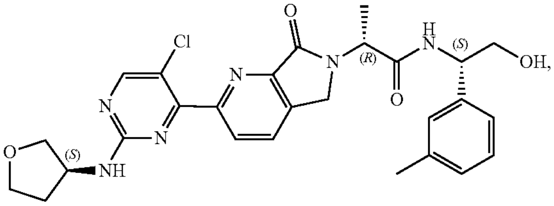

-continued
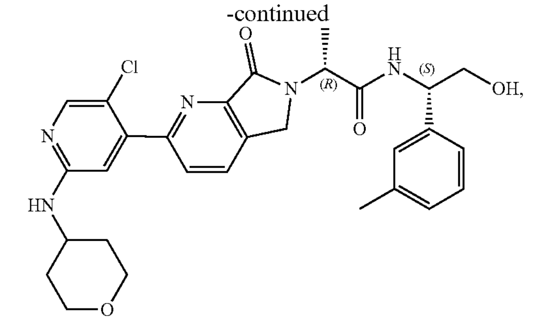
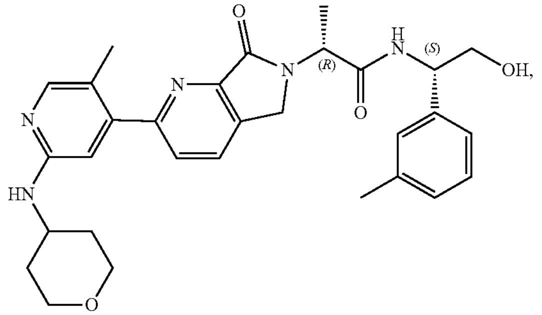
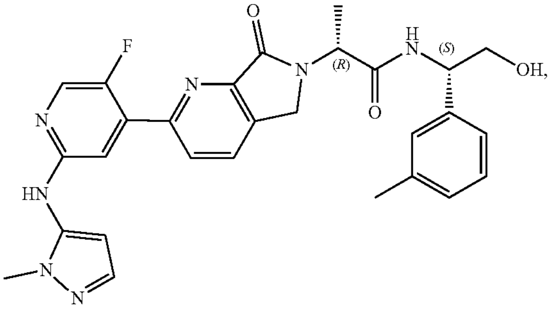
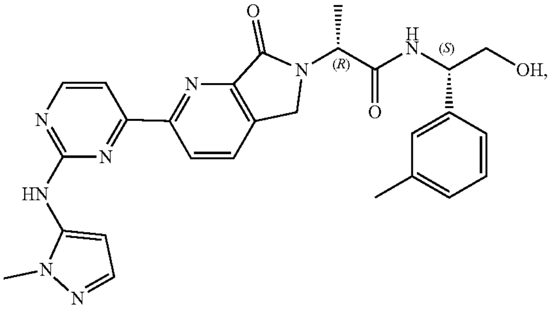
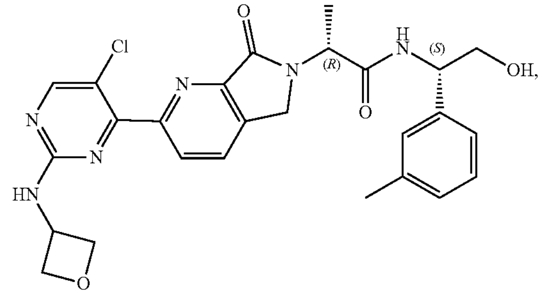
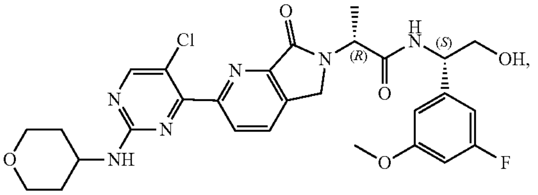
-continued
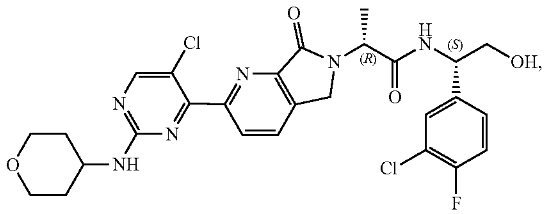
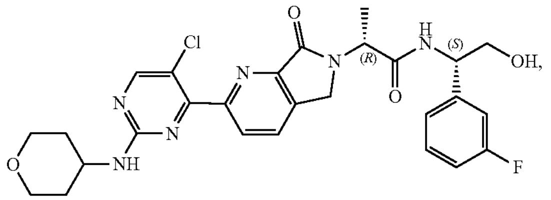
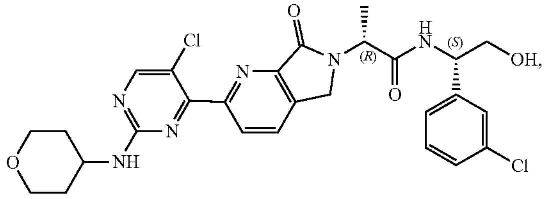
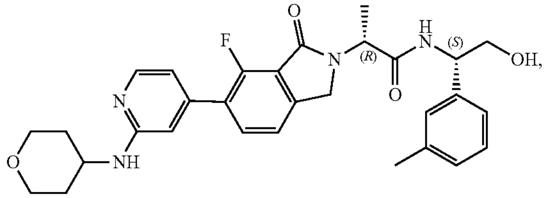
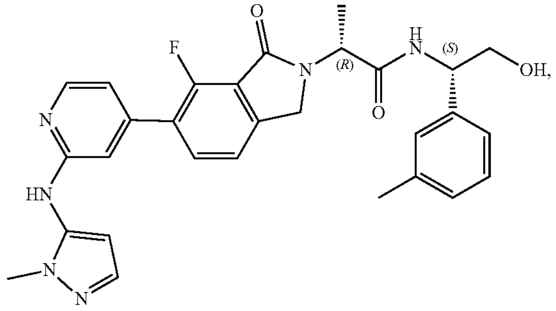
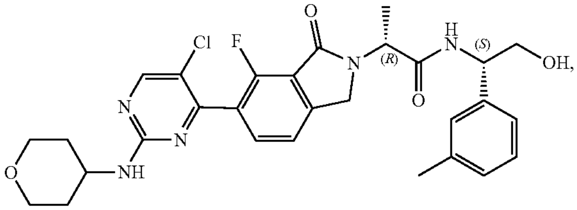
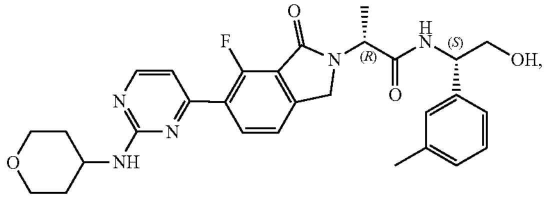

-continued
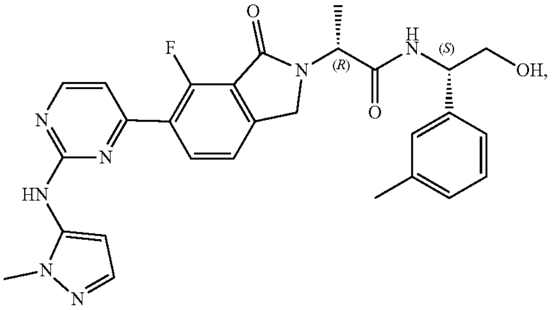
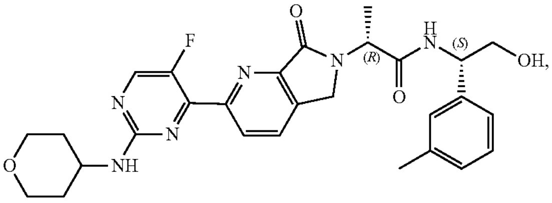
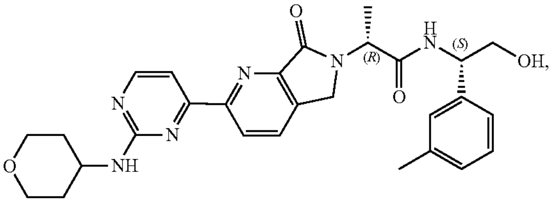
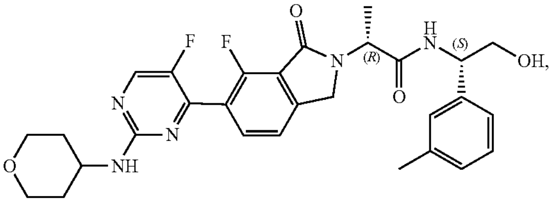
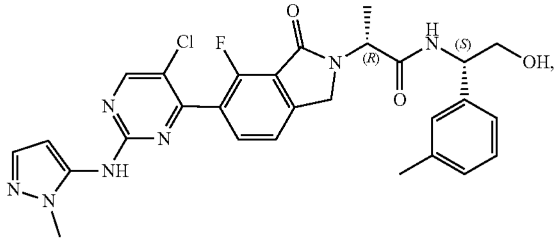
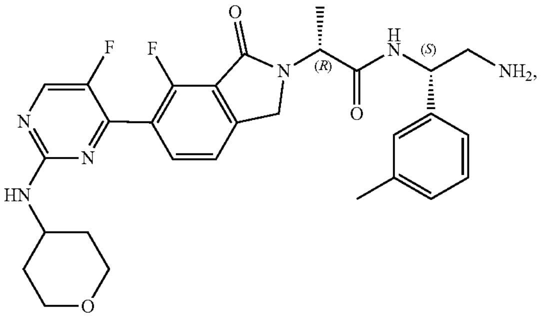
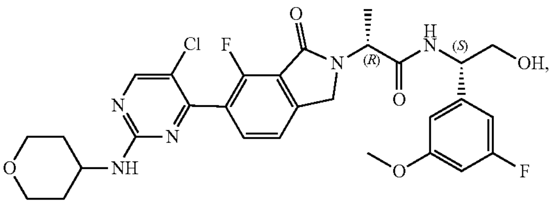
-continued
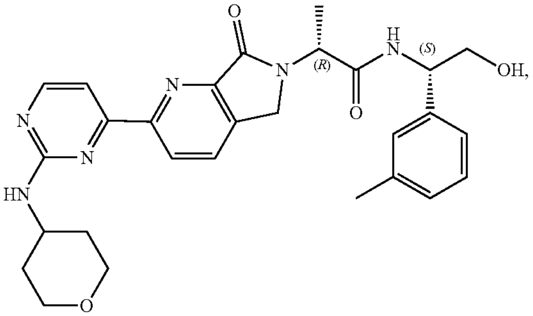
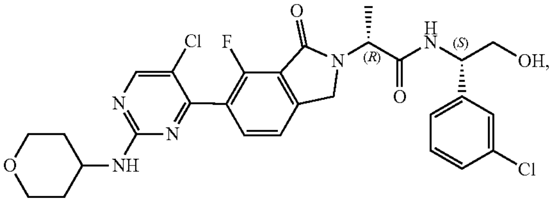
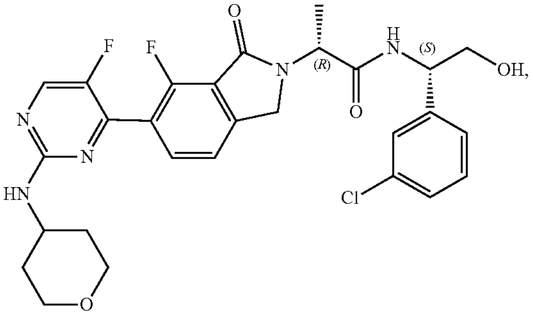
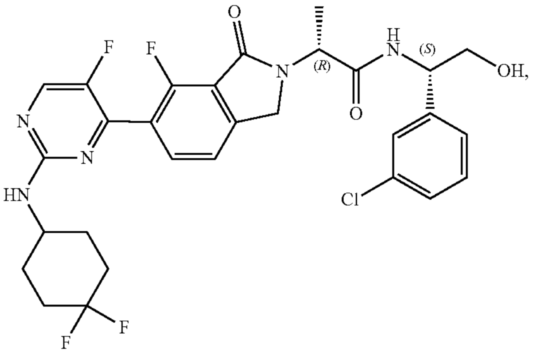
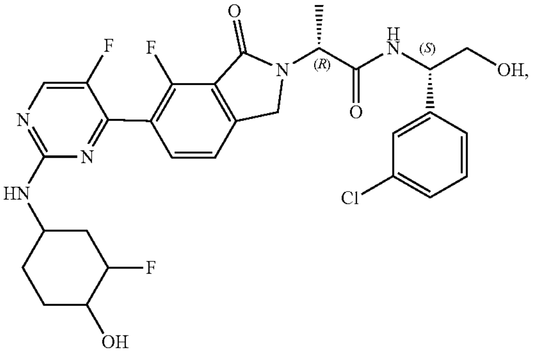

-continued
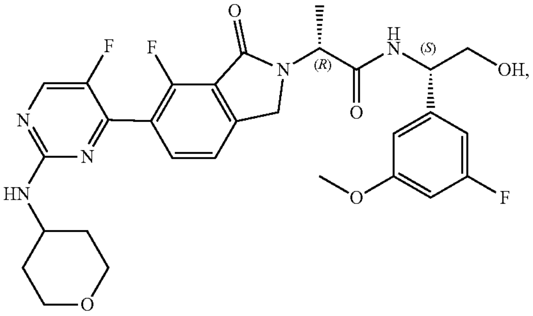
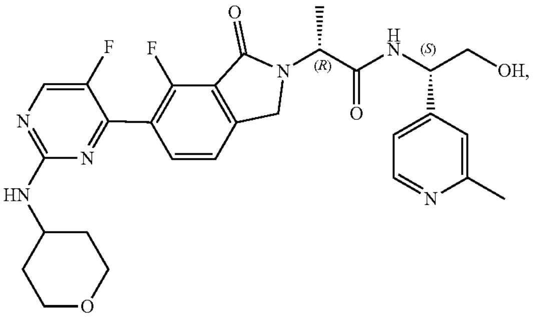
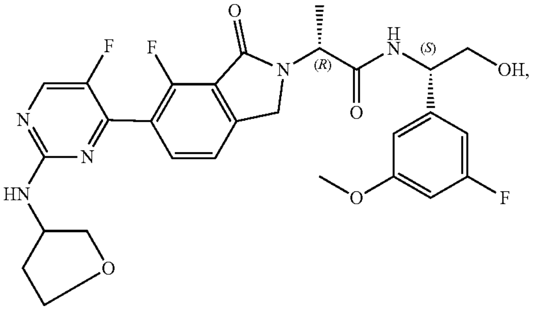
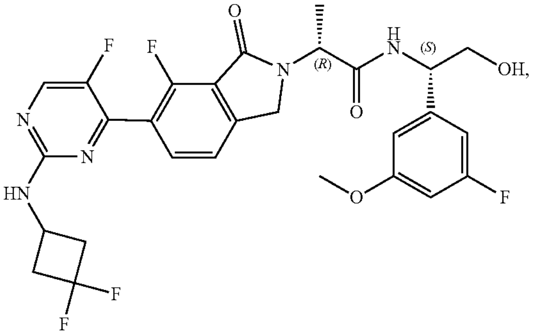
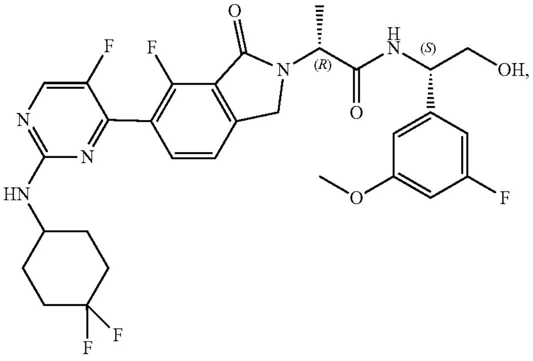
-continued
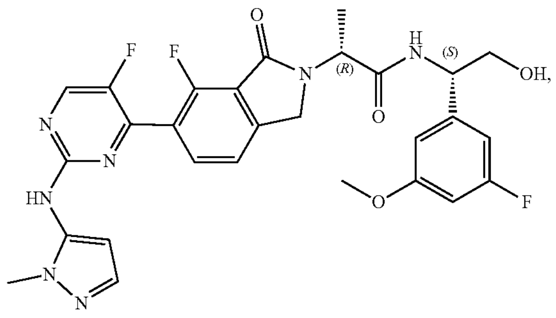
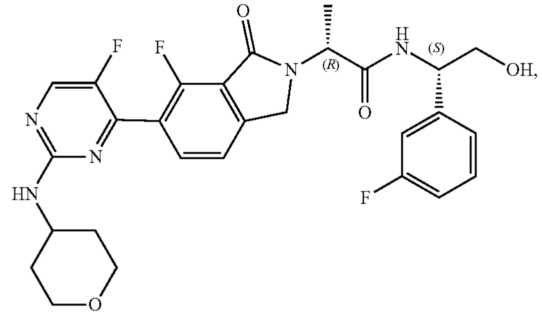
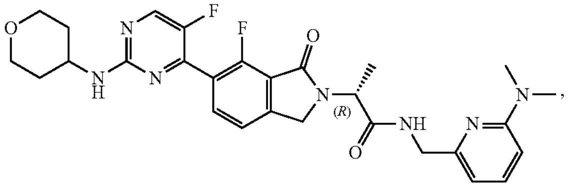
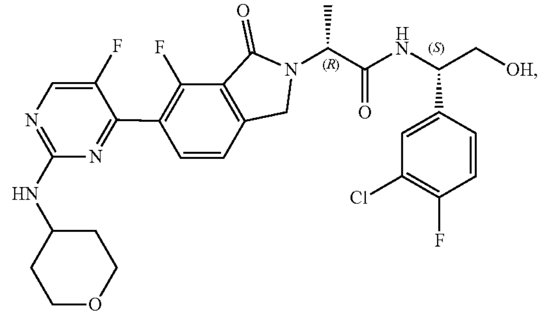
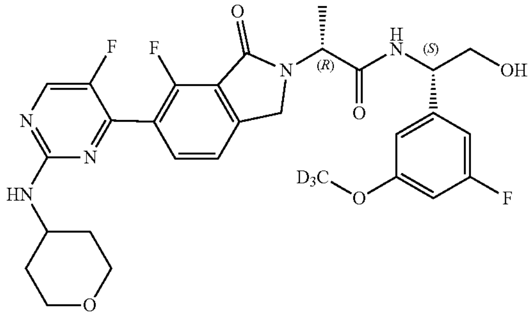
or -continued

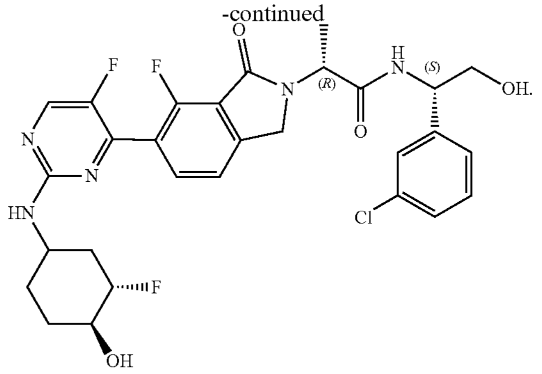

13. The compound represented by formula (I) or a pharmaceutically acceptable salt thereof according to claim 9, wherein:

$R_1$ is groups: unsubstituted 4-to 6-membered heterocycloalkyl, or substituted 5-to 6-membered heteroaryl;

or, Ar is any one of the following substituted or unsubstituted groups: phenyl, pyridyl.

14. The compound represented by formula (I) or a pharmaceutically acceptable salt thereof according to claim 13, wherein:

$R_1$ is oxetanyl, oxolanyl, pyridyl or pyrazolyl.

15. The compound represented by formula (I) or a pharmaceutically acceptable salt thereof according to claim 1, wherein, $R_1$ is unsubstituted 3-to 8-membered heterocycloalkyl;

$R_{4a}$ and $R_{4b}$ are independently selected from hydrogen and substituted $C_1$-$C_6$ alkyl; the substituent is hydroxyl;

Ar is substituted or unsubstituted 5-to 10-membered aryl; the substituent is independently selected from one or more than one halogen, $C_1$-$C_6$ alkyl, $C_1$-$C_6$ alkoxy;

M is N;

$M_1$ is $CR_6$; $R_6$ is halogen;

$M_2$ is N;

X and Y are each CH.

16. A pharmaceutical composition, wherein, the pharmaceutical composition comprises (i) the compound represented by formula (I) or a pharmaceutically acceptable salt thereof according to claim 1, and (ii) a pharmaceutically acceptable carrier.

17. A method for inhibiting an ERK kinase, the method comprises administering a therapeutically effective amount of a substance X to an individual in need thereof, wherein the substance X is the compound represented by formula (I) or a pharmaceutically acceptable salt thereof according to claim 1.

* * * * *